United States Patent
Glezer et al.

(10) Patent No.: US 8,012,745 B2
(45) Date of Patent: Sep. 6, 2011

(54) ASSAY CARTRIDGES AND METHODS OF USING THE SAME

(75) Inventors: Eli N. Glezer, Chevy Chase, MD (US);
Jonathan K. Leland, Silver Spring, MD (US); Mark A. Billadeau, Knoxville, MD (US); Joseph M. Leginus, Silver Spring, MD (US); Bandele Jeffrey-Coker, Darnestown, MD (US); Jeff D. Debad, Gaithersburg, MD (US); Koustubh A. Phalnikar, Gaithersburg, MD (US); Sriram Jambunathan, Jersey City, NJ (US)

(73) Assignee: Meso Scale Technologies, LLC, Gaithersburg, MD (US)

( * ) Notice: Subject to any disclaimer, the term of this patent is extended or adjusted under 35 U.S.C. 154(b) by 206 days.

(21) Appl. No.: 12/244,133

(22) Filed: Oct. 2, 2008

(65) Prior Publication Data
US 2009/0066339 A1   Mar. 12, 2009

Related U.S. Application Data

(62) Division of application No. 10/744,726, filed on Dec. 23, 2003, now Pat. No. 7,497,997.

(60) Provisional application No. 60/436,569, filed on Dec. 26, 2002.

(51) Int. Cl.
*C12M 1/34* (2006.01)
*C12M 3/00* (2006.01)

(52) U.S. Cl. ............... 435/288.7; 435/283.1; 435/287.1; 435/287.2; 436/518; 436/524; 436/525

(58) Field of Classification Search ............... 435/283.1, 435/287.1, 287.2, 288.7; 436/518, 524, 525, 436/164, 172
See application file for complete search history.

(56) References Cited

U.S. PATENT DOCUMENTS

| | | | |
|---|---|---|---|
| 3,918,435 A | 11/1975 | Beall et al. | |
| 4,586,604 A | 5/1986 | Alter | |
| 4,803,998 A | 2/1989 | Kezes et al. | |
| 4,813,432 A | 3/1989 | Saint-Amand | |
| 4,978,504 A | 12/1990 | Nason | |
| 5,266,266 A | 11/1993 | Nason | |
| 5,425,921 A | 6/1995 | Coakley et al. | |
| 5,437,999 A * | 8/1995 | Diebold et al. | 204/403.11 |
| 6,689,258 B1 * | 2/2004 | Lansford et al. | 204/224 M |
| 6,801,041 B2 * | 10/2004 | Karinka et al. | 324/444 |
| 7,419,821 B2 * | 9/2008 | Davis et al. | 435/288.5 |

FOREIGN PATENT DOCUMENTS

| | | |
|---|---|---|
| DE | G8500471.5 | 5/1985 |
| EP | 0420450 A1 | 4/1991 |

OTHER PUBLICATIONS

Supplemental European Search Report dated Jun. 15, 2011, received in a corresponding European Patent Application.

* cited by examiner

*Primary Examiner* — Melanie J Yu
(74) *Attorney, Agent, or Firm* — Scully, Scott, Murphy & Presser, P.C.

(57) ABSTRACT

Assay modules, preferably assay cartridges, are described as are reader apparatuses which may be used to control aspects of module operation. The modules preferably comprise a detection chamber with integrated electrodes that may be used for carrying out electrode induced luminescence measurements. Methods are described for immobilizing assay reagents in a controlled fashion on these electrodes and other surfaces. Assay modules and cartridges are also described that have a detection chamber, preferably having integrated electrodes, and other fluidic components which may include sample chambers, waste chambers, conduits, vents, bubble traps, reagent chambers, dry reagent pill zones and the like. In certain preferred embodiments, these modules are adapted to receive and analyze a sample collected on an applicator stick.

17 Claims, 44 Drawing Sheets

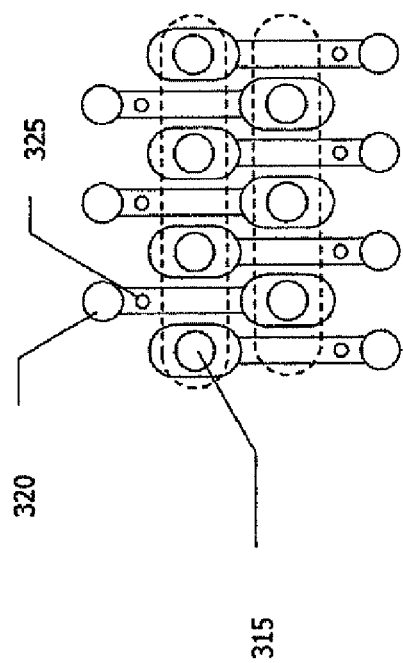
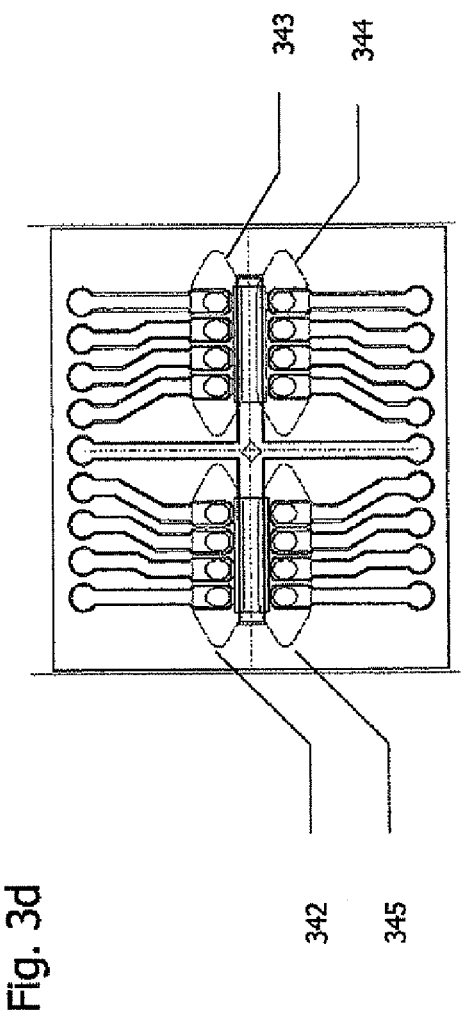
Fig. 3d
Fig. 3e

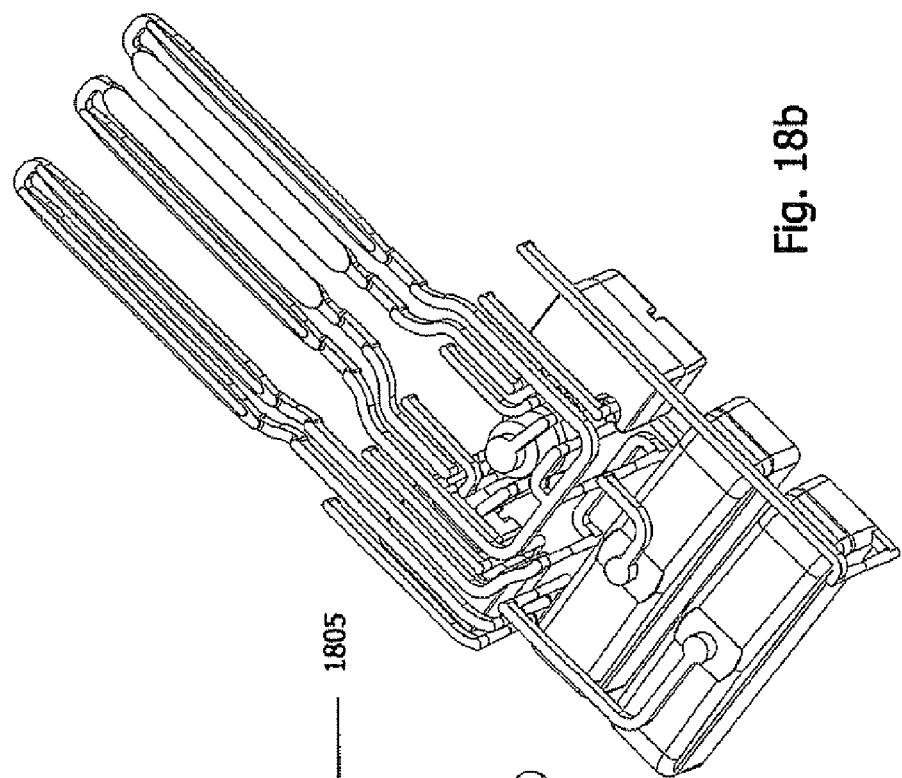
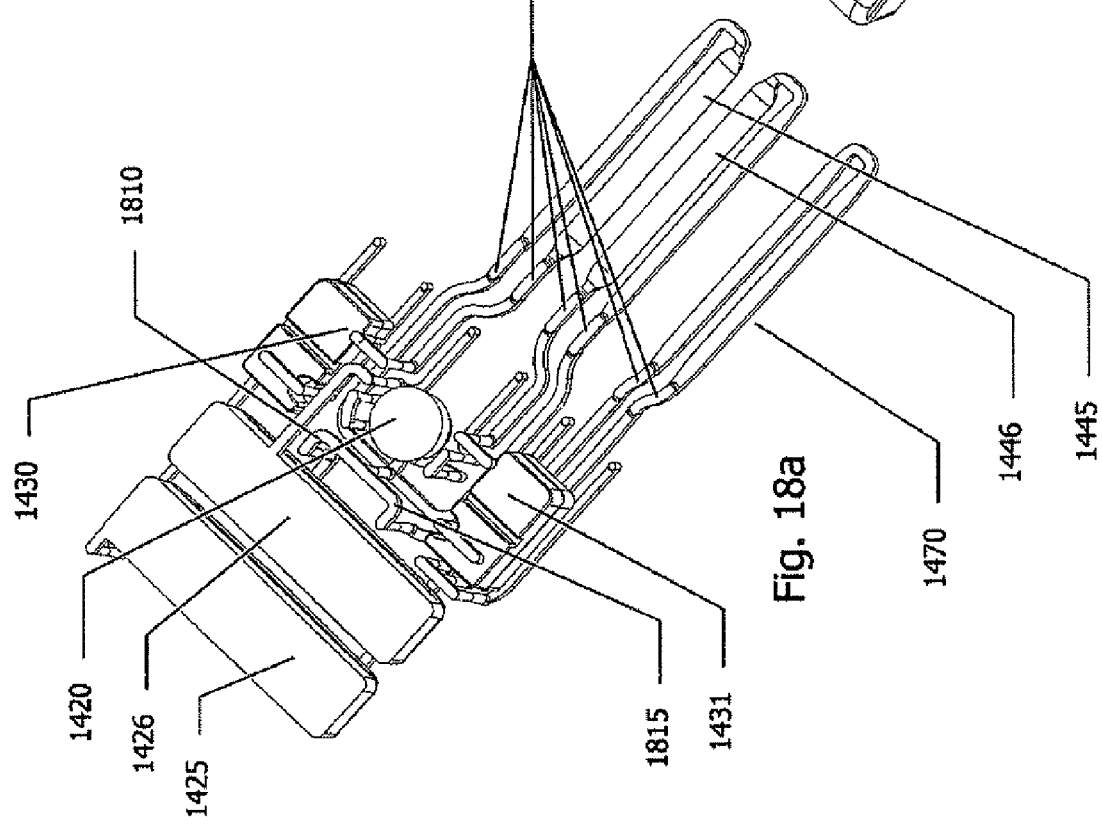

ASSAY CARTRIDGES AND METHODS OF USING THE SAME

CROSS-REFERENCE TO RELATED APPLICATION

This is a divisional of U.S. patent application Ser. No. 10/744,726, filed Dec. 23, 2002, now U.S. Pat. No. 7,497,997 which claims priority of U.S. Provisional Application No. 60/436,569, filed Dec. 26, 2002, which is incorporated herein by reference.

FIELD OF THE INVENTION

This application relates to apparatuses, systems, kits and methods for conducting chemical, biochemical and/or biological assays on a sample. These apparatuses include assay cartridges and cartridge readers for conducting these assays. The application also describes electrode arrays for use in assays, methods of preparing and using these electrode arrays and diagnostic devices comprising the arrays. These electrode arrays may be incorporated into the cartridges and apparatuses of the invention.

BACKGROUND OF THE INVENTION

Clinical measurements have been traditionally carried out in central clinical labs using large clinical analyzers that can handle large numbers of samples in batch mode. These laboratories are staffed by trained personnel that are capable of maintaining and running these complex analyzers. There is a growing desire to move clinical measurements from the central lab to the "point of care", e.g., the emergency room, hospital bedside, physicians office, home, etc. Point of care measurements allow a care provider or patient to quickly make decisions based on diagnostic information, as opposed to having to wait hours or days to receive laboratory results from a clinical lab. The difficulty in developing point of care diagnostic systems has been making them small enough and easy enough to use so that they can be used by unskilled operators in decentralized clinical settings, but at the same time maintaining the low cost, diverse assay menu, and/or high performance of tests carried out on traditional clinical analyzers in central laboratories.

SUMMARY OF THE INVENTION

The invention relates in part to assay modules, preferably assay cartridges. An assay module of the invention incorporates one or more fluidic components such as compartments, wells, chambers, fluidic conduits, fluid ports/vents, valves, and the like and/or one or more detection components such as electrodes, electrode contacts, sensors (e.g. electrochemical sensors, fluid sensors, mass sensors, optical sensors, capacitive sensors, impedance sensors, optical waveguides, etc.), detection windows (e.g. windows configured to allow optical measurements on samples in the cartridge such as measurements of absorbance, light scattering, light refraction, light reflection, fluorescence, phosphorescence, chemiluminescence, electrochemiluminescence, etc.), and the like. A module may also comprise reagents for carrying out an assay such as binding reagents, detectable labels, sample processing reagents, wash solutions, buffers, etc. The reagents may be present in liquid form, solid form and/or immobilized on the surface of solid phase supports present in the cartridge. In certain embodiments of the invention, the modules include all the components necessary for carrying out an assay. In other embodiments, the invention also includes a module reader adapted to receive the module and carry out certain operations on the module such as controlling fluid movement, supplying power, conducting physical measurements on the cartridge, and the like.

The invention also relates, in part, to a method of performing a plurality of assays wherein an assay dependent signal is measured using a plurality of electrodes. Preferably, at least one of the electrodes is used as a working electrode for measuring an assay dependent signal and, subsequently, as a counter electrode for measuring a different assay dependent signal at a different electrode. In one preferred embodiment, at least two of the electrodes are used as a working electrode and, subsequently, as a counter electrode. Most preferably, the method uses at least a dedicated counter electrode, a dedicated working electrode and two or more additional electrodes, each of which is used as a working electrode for measuring an assay dependent signal and, subsequently, as a counter electrode for measuring a different assay dependent signal at a different electrode.

In another preferred embodiment, a method of performing a plurality of biochemical assays using a plurality of electrodes is disclosed. The method comprises the steps of applying electrical energy between first and second electrodes, measuring an assay dependent signal at the second electrode, applying electrical energy between the second electrode and a third electrode and measuring an assay dependent signal at the third electrode. The measured assay dependent signal is, preferably, selected from electrical current, electrical potential and/or electrode-induced luminescence. The second and third electrodes can each have an assay reagent immobilized thereon. Furthermore, each electrode can have a different assay reagent immobilized thereon where each assay reagent can be specific for a different analyte of interest.

In one embodiment, the plurality of electrodes can be arranged within a flow cell. In a preferred embodiment, the flow cell can have a flow cell path along which the electrodes may be arranged. The electrodes can be arranged along the path, sequentially. Moreover, the electrodes can be arranged such that the first electrode is adjacent the second electrode and the second electrode is adjacent the third electrode. The electrodes can be arranged within a single detection chamber. Additionally, the electrodes may comprise printed carbon ink. Further, the assay reagents may be immobilized on the electrode surface within an assay domain defined by a dielectric layer on the electrodes.

In yet another embodiment, the electrodes may have electrical leads for supplying electrical energy to the electrodes. The electrical leads may comprise exposed surfaces that at least partially define an inlet conduit in fluid communication with the flow cell. The method may then include the further step of applying an inlet conduit interrogation potential between the exposed surfaces of the electrical leads to determine the presence or composition of fluid in the inlet conduit. Preferably the interrogation potential would be of insufficient magnitude to induce electrochemiluminescence.

According to another aspect of the invention, an apparatus for performing a plurality of biochemical assays is disclosed. The apparatus may comprise a plurality of electrodes comprising at least one dedicated working electrode, at least one dual-role electrode and at least one dedicated counter electrode. The dedicated working and dual-role electrodes preferably have deposited thereon an assay reagent. The dual-role electrode is advantageously configured to operate first as the working electrode and then as the counter electrode. The assay reagent is preferably a binding reagent that is specific for an analyte of interest and may also be different for each of the dedicated working and dual-role electrodes.

Still further, the plurality of electrodes may be arranged within a flow cell, along the flow cell path. Preferably, the dedicated counter electrode is adjacent the dual-role electrode and the dual-role electrode is adjacent the dedicated working electrode. In addition, the plurality of electrodes are preferably arranged within a single detection chamber. The plurality of electrodes may comprise printed carbon ink. The dedicated working and dual-role electrodes may have assay reagents immobilized thereon within an assay domain defined by a dielectric layer.

The dedicated working, dual-role and dedicated counter electrodes preferably have corresponding electrical leads for supplying electrical energy to the electrodes. Preferably, at least two non-adjacent electrical leads would have an exposed surface located thereon. These exposed surfaces of the electrical leads preferably at least partially define an inlet conduit in fluid communication with a flow cell so that fluid present within the inlet conduit is in electrical contact with the exposed surfaces. In such a preferred embodiment, the exposed surfaces may be configured to apply an inlet conduit interrogation potential between exposed surfaces to determine the presence or composition of fluid in the inlet conduit. Additionally, the apparatus is preferably configured such that the applied interrogation potential between exposed surfaces is of insufficient magnitude to induce electrochemiluminescence at the corresponding electrodes.

In yet another embodiment, the apparatus can be configured with an optical detector for detecting luminescence generated at the dedicated working and dual-role electrodes. Alternatively, the apparatus may comprise a voltmeter for measuring potentials at the dedicated working and dual-role electrodes. In yet another alternative embodiment, the apparatus may comprise an ammeter for measuring electrical current at said dedicated working and dual-role electrodes. Preferably, the electrodes are housed in a disposable assay cartridge and the optical detector(s), voltmeter(s), and/or ammeter(s) are housed in a separate re-usable cartridge reader.

In accordance with another aspect of the invention, a cartridge for conducting a plurality of assays may comprise a flow cell having an inlet, outlet and a detection chamber. The detection chamber preferably comprises a plurality of electrodes arranged in a one dimensional array wherein at least a first electrode has a first assay reagent immobilized thereon. According to certain preferred embodiments, the electrodes may comprise carbon ink. The electrodes preferably have a plurality of electrical leads that supply electrical energy to the electrodes. In addition, the cartridge may comprise a second electrode arranged adjacent to the first electrode, the second electrode preferably having a second assay reagent immobilized thereon.

According to one embodiment, the cartridge preferably has a detection chamber with at least one detection chamber surface. Preferably, at least a portion of the detection chamber surface would be transparent. Still further, the cartridge may comprise an optical detector adapted and arranged to detect luminescence from the detection chamber. Preferably, the optical detector is provided in a separate cartridge reader.

In accordance with another aspect of the invention, a method is disclosed for conducting an electrochemiluminescence measurement wherein impedance is measured between two electrodes and wherein electrochemiluminescence is induced at one of the two electrodes. The impedance is measured between the two electrodes in a measurement chamber to detect the presence of air bubbles. The impedance measurement step is preferably conducted using electrical energy that is insufficient for generating electrochemiluminescence at the electrodes. Additionally, the impedance measurement may be conducted using either a DC impedance measurement or, more preferably, an AC impedance measurement.

According to yet another aspect of the invention, a method of depositing assay reagents on an electrode surface, preferably comprising carbon ink, to form an assay domain is disclosed. The method comprises the steps of dispensing a predetermined volume of the assay reagents on the electrode surface using impact-driven fluid spreading to coat a predefined region having a predefined assay reagent area on the electrode surface. The predetermined volume of said assay reagents is preferably dispensed at a velocity greater than 200 centimeter per second (cm/s). Preferably the predefined assay reagent area is larger than the steady-state spreading area of the predetermined volume of the assay reagents on the electrode surface. More preferably the predefined assay reagent area is at least twice the steady-state spreading area of the predetermined volume of the assay reagents on the electrode surface. The method would preferably use a fluid dispenser utilizing using a fluid micro-dispenser such as a micro-pipette, micro-syringe, solenoid valve dispenser, piezo-driven dispenser, ink-jet printer, bubble jet printer, etc. Also, the assay reagents are preferably substantially free from surfactants.

According to one embodiment, the electrode surface preferably comprises a material having advancing and retreating contact angles for the assay reagents (preferably, aqueous solutions having contact angles that approximate that of water) that differ. More preferably, this difference is at least 10 degrees. The electrode surface need not be plasma treated. Additionally, the predefined region is preferably defined by a dielectric material having dielectric advancing and retreating contact angles for the assay reagents. The dielectric retreating contact angle is preferably greater than the electrode surface retreating contact angle. More preferably, the dielectric advancing and retreating contact angles are about equal to each other but greater (preferably, by more than 10 degrees) than the electrode surface retreating contact angle. Most preferably, the dielectric advancing and retreating contact angles are within about 20 degrees of each other. Also, the predetermined volume may preferably be selected such that any assay reagents that spread onto the dielectric material retreat to an interface between the dielectric material and the electrode surface that defines the predefined region.

A further aspect of the invention relates to a method of adsorbing assay reagents on a carbon ink electrode. The method may include the steps of washing the electrode and then treating the electrode with solution containing the assay reagents. The washing step preferably employs a washing solution comprising a surfactant; e.g., a non-ionic surfactant selected from the surfactants known by the trade names of Brij, Triton, Tween, Thesit, Lubrol, Genapol, Pluronic (e.g., F108), Tetronic, Tergitol, and Span, most preferably Triton X100. Additionally, after the washing step and prior to the treating step, the electrode may be rinsed with a surfactant free solution. Preferably, the electrode is soaked in the surfactant free solution for about one hour.

In accordance with a still further aspect of the invention, a method of forming an assay domain comprising an assay reagent is disclosed. Preferably, in accordance with such method, a predefined region of a surface is treated with an avidin solution so as to form an adsorbed avidin layer within the predefined region of the surface. Next, the adsorbed avidin layer is preferably treated with a solution comprising the assay reagent, the assay reagent being linked to biotin. More preferably, the avidin solution is dried on the surface prior to treatment with the assay reagent solution. The method may also employ the step of washing the adsorbed avidin layer prior to treatment with the assay reagent solution. The surface may be a carbon ink electrode. The predefined region is preferably defined by a boundary adapted to confine the avidin and/or assay reagent solutions to the predefined region (most preferably both solutions are confined to the pre-defined region). The boundary can be defined by a dielectric layer.

According to another aspect of the invention, a method of forming a plurality of assay domains is disclosed wherein one of a plurality of predefined regions of a surface are treated with an avidin solution so as to form an adsorbed avidin layer within the predefined region of the surface. The adsorbed avidin layer is then preferably treated with a solution comprising an assay reagent linked to biotin. These steps may then be repeated for each of the plurality of assay domains. More preferably, the avidin solution is dried on the surface prior to treatment with the assay reagent solution. The method may also employ the step of washing the adsorbed avidin layer prior to treatment with the assay reagent solution. The surface may be a carbon ink electrode. The predefined region is preferably defined by a boundary adapted to confine the avidin and/or assay reagent solutions to the predefined region (most preferably both solutions are confined to the pre-defined region). The boundary can be defined by a dielectric layer.

The assay reagent in each domain may be the same or may be different. Assay reagents that may be used include, but are not limited to, antibodies, fragments of antibodies, proteins, enzymes, enzyme substrates, inhibitors, cofactors, antigens, haptens, lipoproteins, liposaccharides, cells, sub-cellular components, cell receptors, membrane fragments, viruses, nucleic acids, antigens, lipids, glycoproteins, carbohydrates, peptides, amino acids, hormones, protein-binding ligands, pharmacological agents, membrane vesicles, lipsomes, organelles, bacteria or combinations thereof. Preferably, the assay reagents are binding reagents capable of specifically binding to an analyte of interest or, alternatively, of competing with an analyte of interest for binding to a binding partner of the analyte of interest. Especially preferred assay reagents are antibodies and nucleic acids.

According to one embodiment, the avidin solution for forming one, or a plurality, of assay domains may comprise a polymeric form of avidin. The polymeric form of avidin may be formed by forming a solution of avidin and a cross-linking molecule, the cross-linking molecule preferably having a plurality of biotin groups. The ratio of the cross-linking molecule to avidin is preferably between 0.01 and 0.25. The method of forming an assay domain can preferably include the step of washing the assay domain or plurality of assay domains. More preferably, the wash solution comprises blocking agent, wherein the blocking agent can be a protein or biotin.

The invention also relates to assay cartridges employing the electrode arrays and/or binding domains employing these electrode described above (and adapted for carrying out the methods described above for using these arrays and domains) and assay cartridge readers for operating and analyzing these cartridges. The invention also relates to assay systems comprising these cartridges and cartridge readers. The cartridges and readers, preferably, comprise the necessary fluidics and control systems for moving sample and reagent fluids, collecting waste fluids, removing and/or introducing bubbles from liquid reagents and/or samples, conducing physical measurements on the samples and/or extracting samples.

The invention also relates to assays cartridges comprising a sample chamber preferably having a sealable closure, an optional waste chamber and a detection chamber (preferably, a detection chamber having one or more binding domains having immobilized binding reagents, more preferably, one or more binding domains on one or more electrodes, most preferably an electrode array of the invention as described above). The detection chamber is connected to the sample chamber via a sample conduit and, if present, to the waste chamber via a waste conduit. The assay cartridge may also include a sample chamber vent port connected the sample chamber and/or a waste chamber vent port connected to the waste chamber. The sample can include a capillary break, preferably a z-transition. The z-transition preferably includes a fluid conduit segment that connects two planar fluidic networks of the cartridge. The capillary break may alternatively comprise a double z-transition.

In another embodiment of an assay cartridge that includes: a vented sample chamber with an introduction port and a sealable closure; a vented waste chamber; and a detection chamber (preferably, a detection chamber having one or more binding domains having immobilized binding reagents, more preferably, one or more binding domains on one or more electrodes, most preferably an electrode array of the invention as described above) connected to the sample and waste chambers via sample and waste conduits, respectively, one or more fluidic networks may be defined within the cartridge's body by one or more cover layers mated to a side of the cartridge body. A second cover layer, or set of cover layers, may be mated to a second side of the cartridge body to form one or more additional second side fluidic networks therebetween, the first and second side fluidic networks being in fluidic communication by at least one though-hole within the cartridge body. The fluidic networks may be defined, at least in part, by recesses in the cartridge body and/or cover layers. In addition, at least one of the fluidic networks may be defined, at least in part, by apertures within a gasket layer disposed between the cartridge body and at least one cover layer.

Additionally, embodiments including a z-transition capillary break, the z-transition may comprise, in series, first, second, third, fourth and fifth sample conduit segments, each of the segments being connected at an angle to the adjacent segments and the segments being oriented so that the first and fifth segments are in the first fluidic networks, the third segment is in the second fluidic network and the second and fourth segments are cartridge body through-holes.

Still further, the assay cartridge may comprise a dry reagent in the sample conduit. The dry reagent may comprise, e.g., a labeled binding reagent, a blocking agent, an ECL coreactant and/or an extraction buffer neutralization reagent. In yet another embodiment, the assay cartridge may comprise an air vent port connected to the sample conduit. In still yet another embodiment, the assay cartridge may comprise a vented reagent chamber and a reagent chamber conduit connecting the reagent chamber with the sample conduit. The reagent chamber may comprise a liquid reagent which may optionally be contained within a reagent ampoule in the reagent chamber. The reagent chamber conduit may also be connected to an air vent port.

The reagent conduit may include a dry reagent; the dry reagent may comprise, e.g., a labeled binding reagent, a blocking agent, an ECL coreactant and/or an extraction buffer neutralization reagent. The liquid reagent may be, e.g., a wash buffer, an extraction buffer, an assay diluent and/or an ECL read buffer. The extraction buffer is, preferably, nitrous acid or a nitrate salt.

In another embodiment the assay cartridge may further comprise a second reagent chamber holding a second liquid reagent, a second reagent chamber vent port connected to the second reagent chamber and a second reagent chamber conduit connecting the second reagent chamber with the sample conduit.

The detection chambers in the cartridges of the invention preferably include an array of binding reagents as described above. Still further, the detection chamber may comprise one or more electrodes having binding reagents immobilized thereon as described above.

In other embodiments the assay cartridge may further comprise a second waste chamber, a second waste chamber vent port connected to the second waste chamber and a second detection chamber connected to the sample chamber or the first sample conduit by a second sample conduit and to the second waste chamber by a second waste conduit. In addition, at least a portion of one wall of the detection chamber may be substantially transparent to allow optical monitoring of materials in the detection chamber. The assay cartridge may also comprise a second detection chamber connected to the sample chamber or the first sample conduit by a second sample conduit and to the first waste chamber by a second waste conduit. Similarly, at least a portion of one of the cover layers may be substantially transparent to allow the monitoring of fluid flow within said cartridge.

In other embodiments, the cover layers may have a first region comprising a patterned array of immobilized binding reagents defining a surface of the detection chamber and a second region having a dry reagent thereon defining a surface of the sample conduit. The cartridge may also have two second side cover layers defining two second side fluidic networks and a first side bridge cover layer that connects the two second side fluidic networks. In certain embodiments, the dry reagents may be on the first side bridge cover layer.

In yet a still further embodiment, an assay cartridge for analyzing a sample collected with an applicator stick comprising a shaft and a sample collection head, may comprise a sample chamber having an elongated cavity that has a first elongated region and a second elongated region, the regions being oriented at an angle with respect to each other to bend the shaft upon insertion of the applicator stick into the sample chamber and promote fracture of the shaft. The angle is preferably between 30 and 70 degrees. Also, in some embodiments the cross-sectional area of the cavity is less than 2 times the width of the applicator stick head. The fracture preferably produces a shortened stick fragment that includes the sample collection head where the length of the fragment is less than the length of the cavity. The cartridge also may include a sealable closure for sealing the sample compartment with the shortened stick fragment in the cavity.

Other embodiments for an assay cartridge may comprise an extraction reagent chamber for holding an extraction reagent, a sample chamber having sample introduction port with a sealable closure wherein the sample chamber is adapted to receive an applicator stick and a first detection chamber (preferably, a detection chamber having one or more binding domains having immobilized binding reagents, more preferably, one or more binding domains on one or more electrodes, most preferably an electrode array of the invention as described above) connected to the sample chamber by a first sample conduit. The sample chamber is connected to the extraction reagent chamber by an extraction reagent chamber conduit. A filter may optionally be included between the sample chamber and the sample conduit. The sample and extraction reagent conduits may be connected to and arranged along the length of the cavity. The extraction reagent, preferably, comprises nitrous acid or a nitrate salt.

Yet another embodiment of an assay cartridge comprises a wash reagent chamber for holding a wash reagent and a detection chamber (preferably, a detection chamber having one or more binding domains having immobilized binding reagents, more preferably, one or more binding domains on one or more electrodes, most preferably an electrode array of the invention as described above), wherein the wash reagent chamber and the waste chamber are connected to the detection chamber via a wash conduit and a waste conduit, respectively. Alternatively, the waste chamber may be connected to the detection chamber via a waste conduit and the wash reagent chamber connected to the sample conduit via a wash conduit.

In accordance with another aspect of the invention, a method of performing a cartridge based assay is disclosed. The method generally comprises moving the sample from the sample chamber into the first sample conduit branch. The dry reagent is reconstituted in the sample and a sample slug having a predetermined volume is moved into the detection chamber and then into the waste chamber. Reagent is then moved into the detection chamber and a signal is measured.

The step of moving the sample into the sample conduit may involve opening the sample vent port and applying a vacuum to the first waste chamber vent port. The sample slug may be moved into the detection chamber by opening the air vent port and applying a vacuum to the first waste chamber vent port. Moving the reagent may be accomplished by opening the reagent vent port and applying vacuum to the first waste chamber vent port. Optionally, moving the reagent may also comprise opening the air vent port to segment the reagent.

The assay may be a binding assay where the detection chamber comprises one or more immobilized binding reagents and the first dry reagent comprises one or more labeled binding reagents. The signal may be an electrochemiluminescent signal wherein the detection chamber further comprises electrodes, the one or more labeled binding reagents can comprise one or more electrochemiluminescent labels and the first reagent may comprise an electrochemiluminescence coreactant.

In certain embodiments the dry reagent may be reconstituted by moving the sample back and forth over the dry reagent. In addition, the slug of sample may be moved back and forth in the detection chamber. Moving fluids back and forth can be accomplished by opening the air or sample chamber vent port and alternating between applying positive and negative pressure at the waste chamber vent port.

Selective control of fluid movement may be attained by moving sample and/or reagent for predetermined periods of time. Alternatively, some embodiments may move sample and/or reagent until the sample and/or reagent reach predetermined locations. In addition, certain embodiments may use fluid sensors to determine when the sample and/or reagent reach the predetermined locations. The slug of sample may be mixed in the detection chamber by moving the slug back and forth within the detection chamber. In certain embodiments the sample conduit and/or reagent conduit may comprise a z-transition that act as a capillary break.

The method may also comprise adding the sample to the sample chamber through a sample introduction port and sealing the sample introduction port. The invention includes embodiments where the sample is a liquid sample and/or the sample contains a solid matrix. The method may also be utilized where the sample chamber is connected to the sample chamber vent through an extraction chamber containing an extraction reagent.

In yet another embodiment, the cartridge based assay method may be carried out on a cartridge having a second vented waste chamber and a second detection chamber connected to the sample chamber by a second sample conduit branch containing a second dry reagent and to the second waste chamber by a second waste conduit. The method would further comprise moving the sample from the sample chamber into the second sample conduit branch, reconstituting the second dry reagent in the sample, moving a second slug of sample having a predetermined volume into the second detection chamber, moving the second slug in the second detection chamber into the second waste chamber, moving reagent into the second detection chamber and measuring a signal from the second detection chamber. The reagent conduit may also comprise a third dry reagent. Other embodiments may employ a second reagent chamber containing a second reagent, wherein the second reagent chamber is connected to the sample conduit or the first reagent conduit through a second reagent conduit and the second reagent is moved into the detection chamber.

Still other embodiments of a method for performing a cartridge based assay may comprise the steps of moving the sample from the sample chamber into the first sample conduit, reconstituting the first dry reagent in the sample, moving a slug of the sample into the first detection chamber, moving the sample in the first detection chamber into the waste chamber, moving the reagent into the detection chamber and measuring a signal from the detection chamber. Such a method may utilize a cartridge having a detection chamber that has an elongated dimension where the sample and reagent conduits connect to the detection chamber at substantially opposite ends of the detection along the elongated dimension. Additionally, the method may be performed such that the sample slug moves through the detection chamber along a path in a forward direction and the reagent moves through the detection chamber along the path in the reverse direction.

In still further embodiments, the method may be performed on a cartridge having second waste and detection chambers where the second detection chamber is connected to the first detection chamber conduit by a second reagent chamber conduit and to the second waste chamber by a second waste conduit. The method may include the step of moving the reagent into the second detection chamber and measuring a signal from the second detection chamber.

In accordance with another aspect of the invention, a method for preparing a sample for analysis may include the steps of inserting an applicator stick, which has a shaft and a sample collection head, used to collect a sample into a cartridge having a sample chamber, breaking the shaft of the applicator stick into a shaft segment and a head segment and sealing the head segment in the sample chamber. The inserting step may occur concurrently with the breaking step or may occur prior to the breaking step. The breaking step may be carried out by applying a force perpendicular to the shaft. Optionally, the sample chamber may include force focusing elements.

In yet other embodiments, the assay cartridge used in the method for preparing a sample for analysis may have a sample chamber that has an elongated cavity, the elongated cavity comprising a first elongated region and a second elongated region wherein the two regions are oriented at an angle with respect to each other. The inserting step of a method using such an assay cartridge may comprise pushing the sample collection head through the first region and into the second region causing the shaft to bend and break. In certain embodiments, the applicator stick breaks at a predefined weak point located on shaft. Preferably, the weak point is located between the first and second regions when the applicator stick is fully inserted.

In a still further embodiment, the method of preparing a sample for analysis may comprise passing an extraction reagent through the sample chamber having the head segment to form a sample liquid and then introducing the sample liquid into the detection chamber. In addition, the sample conduit connected to the sample chamber may comprise a filter. Still further, the cartridge may have a bubble trap chamber connected to the sample chamber and the method may further include the step of introducing the sample liquid into the bubble trap and removing bubbles from the sample liquid prior to introducing the sample liquid into the detection chamber.

In certain embodiments the bubble trap chamber may connect to the sample chamber via a bubble trap conduit that is connected to the sample conduit wherein the bubble trap conduit is connected to the bubble trap chamber at or near the bottom of the bubble trap chamber. In such an embodiment, the step of removing bubbles may comprise maintaining the sample liquid in the bubble trap for a sufficient amount of time to allow any bubbles that might be present in the sample liquid to rise to the top of the sample liquid allowing a reduced bubble portion of the sample liquid to then be removed from the bubble trap chamber through the bubble trap chamber conduit. Alternatively, the bubble trap chamber may be interposed between the sample conduit and the detection chamber and may have an inlet connected to the sample conduit and an outlet connected to the detection chamber wherein the outlet is arranged at or near the bottom of the bubble trap chamber. In such an alternative embodiment, the step of removing bubbles may comprise maintaining the sample liquid in the bubble trap for a sufficient amount of time to allow any bubbles that might be present in the sample liquid to rise to the top of the sample liquid allowing a reduced bubble portion of the sample liquid to be removed from the bubble trap chamber through the bubble trap chamber conduit.

In accordance with yet another aspect invention, an assay system may comprise an assay cartridge in accordance with any of the embodiments of the present invention and a cartridge reader adapted to carry out an assay using the cartridge.

Additionally, a kit is disclosed that may comprise an assay cartridge in accordance with any of the embodiments of the present invention and an applicator stick. The applicator stick of such a kit may have a predefined weak point.

The invention also relates to cartridge readers adapted to control and carryout measurements using the above described cartridges, systems comprising the above described cartridges and a cartridge reader and kits including the cartridge and one or more reagents and/or applicator sticks used in assays carried out employing the cartridges.

BRIEF DESCRIPTION OF THE DRAWINGS

FIGS. 3a-3e illustrate various configurations of an electrodes array for use with a pair-wise firing schemes.

FIG. 7b is a cross-sectional view of the localized washing apparatus depicted in FIG. 7a.

FIG. 11a illustrates the fluidic networks formed on one side of the cartridge, FIG. 11b illustrates the fluidic network formed on the other side of the cartridge and FIG. 11c provides an isometric view with phantom lines to illustrate the entire cartridge fluidic network as seen within the cartridge body.

FIG. 13b is a detail drawing of the gasket and electrode array cover layer depicted in FIG. 13a.

FIG. 14b is an exploded assembly drawing illustrating the laminar assemblage for the two-piece assay cartridge depicted in FIG. 14a.

FIGS. 18a and 18b are top and bottom isometric views, respectively, depicting the fluidic network in accordance with the schematic representation of FIG. 14a.

FIG. 24 illustrates one preferred valve configuration for the assay cartridge depicted in FIG. 14a.

DETAILED DESCRIPTION

Figure 1A:
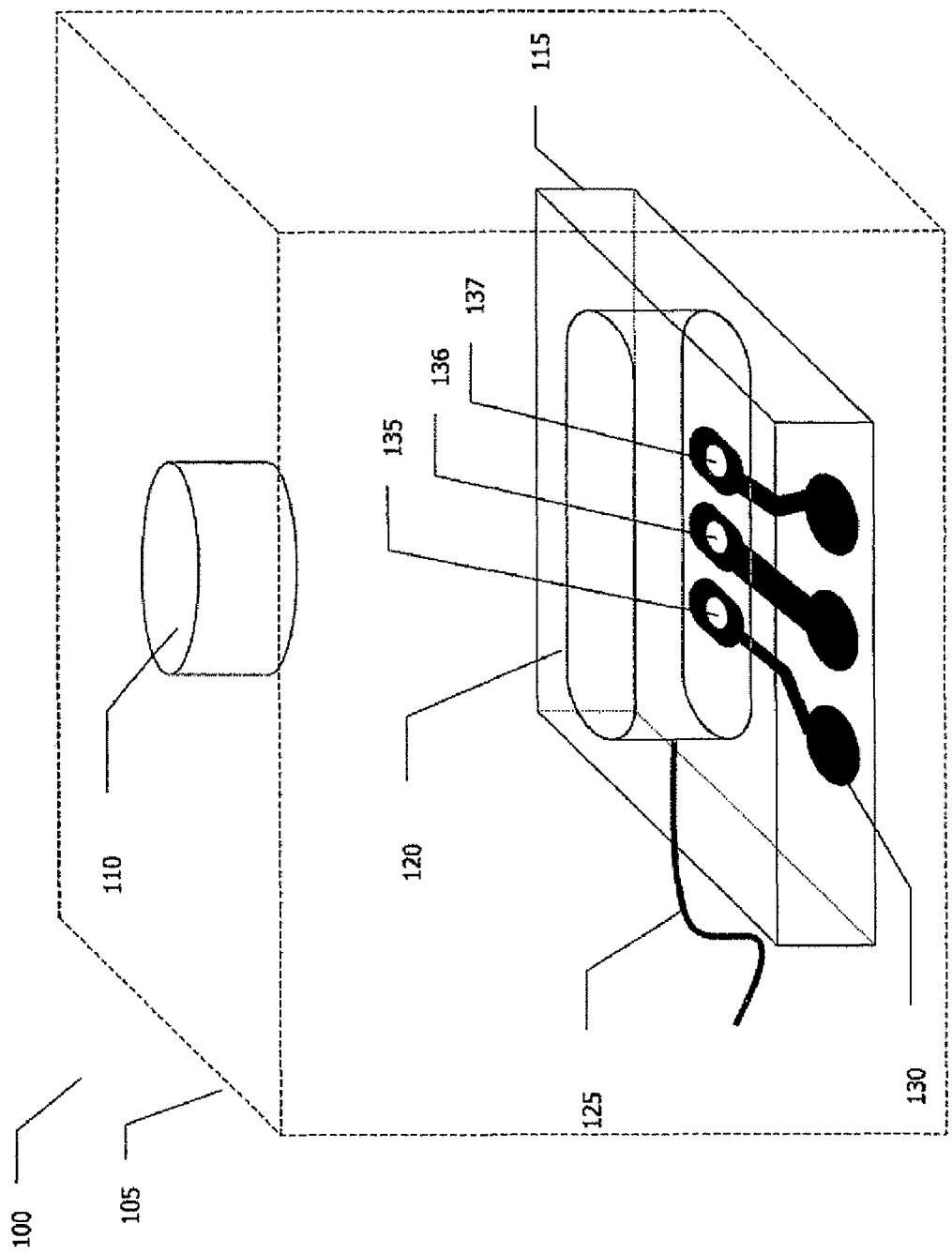
FIG. 1a depicts a simplified pictorial representation of a cartridge-based assay module.

The invention, as well as additional objects, features and advantages thereof, will be understood more fully from the following detailed description of certain preferred embodiments. Where the terms "measure" or "measurement" are used herein, they are understood to encompass quantitative and qualitative measurement, and encompasses measurements carried out for a variety of purposes including, but not limited to, detecting the presence of a thing or property, measuring the amount of a thing or property, and/or identifying a thing or property in a sample The present invention includes apparatuses, electrodes, electrode arrays, systems, system components, kits, reagents and methods for performing one or more assays on a sample. The invention includes assay modules (e.g., assay cartridges, assay plates, etc.) having one or more assay cells (e.g., wells, compartments, chambers, conduits, flow cells, etc.) that may comprise one or more assay domains (e.g., discrete locations on a assay cell surface where an assay reaction occurs and/or where an assay dependent signal, such as an electrochemical or preferably an electrode induced luminescence signal is induced) for carrying out a plurality of assay measurements.

In certain preferred embodiments, assay domains are supported on assay electrodes (preferably, an array of assay electrodes, most preferably a one dimensional array of assay electrodes) so as to permit the conduct of assays based on electrochemical or electrode induced luminescence measurements. The assay domains are, optionally, defined by a dielectric layer deposited on the electrodes. The assay modules, preferably, have one or more attributes that make them suitable for use in "point of care" clinical measurements, e.g., small size, low cost, disposability, multiplexed detection, ease of use, etc. The methods and apparatuses of the invention, allow these benefits to be achieved while maintaining the performance of traditional batch processing instruments of the type typically used in the central clinical lab.

The assay module may comprise the necessary electronic components and/or active mechanical components for carrying out an assay measurement, e.g., one or more sources of electrical energy, ammeters, potentiometers, light detectors, temperature monitors or controllers, pumps, valves, etc. Preferably, some or all of the electronic and/or active mechanical components are arranged within a separate assay module reader. The reader would also have the appropriate electrical, fluidic and/or optical connections to the assay module for carrying out an assay on the assay module. Using such an arrangement, the assay module can be designed to be low cost and disposable while the reader (which holds the more expensive and complex components) is reusable. A preferred assay procedure using an assay module and assay reader would comprise inserting the cartridge in the reader, making the appropriate electrical, fluidic and/or optical connections to the cartridge (making use of electrical, fluidic and/or optical connectors on the cartridge and reader), and conducting an assay in the cartridge. The sample is preferably introduced into the cartridge prior to inserting the cartridge in the reader. The assay may also involve adding one or more assay reagents to the cartridge; preferably, one or more assay reagents are stored in the cartridge in a dry and/or wet form.

The invention also includes methods of preparing the assay modules including methods for preparing electrode arrays and forming assay domains on these electrode arrays. The invention also includes methods for washing assay domains to remove unbound reagents without allowing these reagents to interact with other surfaces in the assay module.

One preferred embodiment of the invention comprises an assay cartridge comprising one or more assay flow cells. The assay flow cell comprises a chamber having a fluid inlet and fluid outlet and a flow path between the inlet and outlet. An array of electrodes is patterned on an internal surface of the chamber. When used in electrode induced luminescence assays, the internal chamber surface opposing the electrode array is, preferably, light-transmissive so as to allow for the detection of light generated at the electrodes. One or more of the electrodes comprise assay reagents immobilized on the electrode. These assay domains are used to carry out assay reactions which are detected by using the electrode to induce an assay dependent signal such as an electrochemical or, more preferably, an electrode induced luminescence signal and detecting the signal. Preferably, these assay reagents are arranged in one or more assay domains defined by apertures in a dielectric layer deposited on the electrode. Optionally, the fluid inlet comprises a fluid inlet line that has sensors for detecting the presence of fluid in the fluid inlet line.

Preferably, the electrodes in the assay cartridge are patterned in a one dimensional array along the fluid path. The array and or fluid path are, preferably, in a linear arrangement, although other shapes (e.g., arcs, curves, zig-zags, etc. may also be used). In such a configuration, it is advantageous for the active area of the electrodes and aspect ratio of the flow path be selected to ensure that assay domains on the electrode efficiently sample analytes in fluids passing through the flow cell. Most preferably, the length of the flow path along the direction of flow is greater than the width perpendicular to the direction of flow, the active area of the electrode takes up a significant portion of the width of the flow path (preferably greater than 60%, more preferably greater than 80%), and/or the height of the flow path above the electrodes is small compared to the width of the flow path. Surprisingly, it has been found that the surface area of dedicated counter electrodes in the flow cell can be reduced significantly without affecting assay performance by reusing electrodes used as working electrodes (e.g., working electrodes having binding domains used for electrode induced luminescence assays), these electrodes being reused as counter electrodes for measuring an assay dependent signal from another, preferably adjacent, working electrode. In an especially preferred embodiment, the electrodes are activated in a pair-wise fashion along the path of the flow cell, the interior electrodes in the one-dimensional electrode array being used as working electrodes for inducing an assay dependent signal and subsequently as counter electrodes for inducing an assay dependent signal at an adjacent electrode.

The assay cartridges of the invention may comprise a plurality of flow cells or detection chambers. In certain preferred embodiments the flow cell may comprise the same assay domains or, at least, have at least some assay domains that share specificity for the same analytes of interest. In these embodiments, the plurality of flow cells may be used to analyze a plurality of different samples or to compare samples that have been pre-treated in different ways. Alternatively, one of the flow cells may be a control flow cell used to analyze a control sample and another of the flow cells may be a test flow cell used to analyze a test sample. The control sample may be a completely pre-defined control sample or may be a mixture comprising the test sample but spiked with added analytes of interest so as to allow for calibration of the assays by the method of standard addition. In an alternative embodiment, the assay cartridge has at least two flow cells that have assay domains for two different assay panels. Advantageously, such a cartridge may be used to separately perform assay reactions that are incompatible with each other.

FIG. 1a depicts a simplified schematic of a cartridge-based biochemical detection system 100 in accordance with one embodiment of the invention. Preferably a system housing, e.g., cartridge reader 105, would include an optical detector 110 and would be adapted and configured to receive and position cartridge 115 and/or optical detector 110 for processing. The system would preferably contain support subsystems (not shown) that may include one or more of the following: storage subsystem for storing assay reagents/consumables and/or waste; sample acquisition/preprocessing/storage subsystem for sample handling; fluidic handling subsystem for handling the reagents, sample, waste, etc. and for providing fluids to the detection chamber 120 via a fluid inlet line 125; electrical subsystem for electrically contacting the cartridge's electrical contacts 130 and supplying electrical energy to the electrodes 135,136,137; and a control subsystem for controlling and coordinating operation of the system and subsystems and for acquiring, processing and storing the optical detection signal.

Figure 1B:
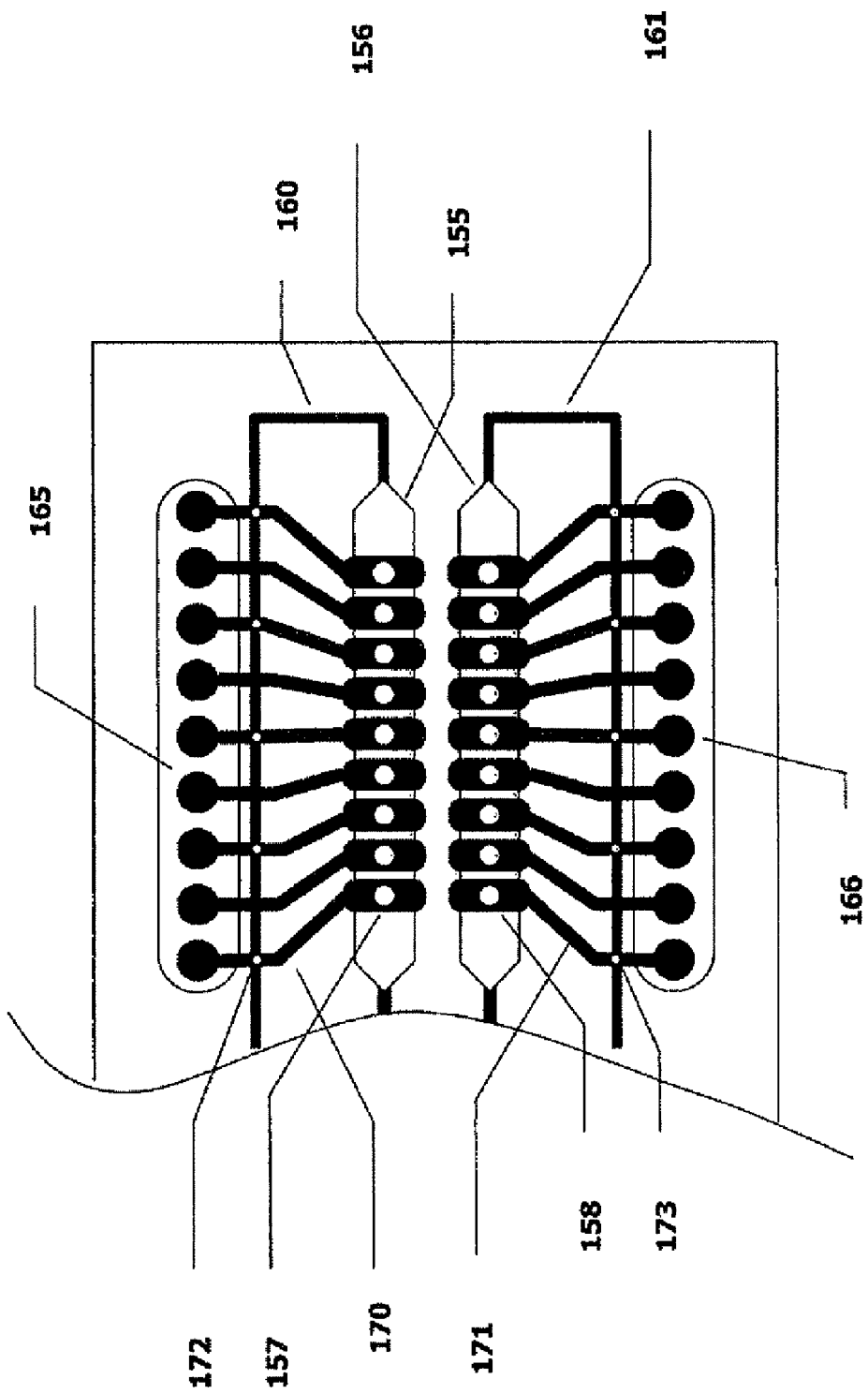
FIG. 1b depicts one embodiment of an assay cartridge having two detection chambers and two banks of individually addressable electrodes.

As illustrated, one preferred embodiment would use an electrode array that preferably has at least one dedicated counter electrode 135, one dual-role electrode 136 and one dedicated working electrode 137. Such a preferred configuration would use a pair-wise firing scheme (discussed in detail below) wherein the dual-role electrode can be reused. FIG. 1b depicts in greater detail one possible embodiment for the detection portion of a cartridge-based device 150. As depicted, two detection chambers 155,156 each contain a bank of nine individually addressable electrodes 157,158. There are two fluid input lines depicted 160,161 for introducing sample, reagents and/or wash solutions into the detection chambers and two banks of electrical contacts 165,166 with corresponding electrical leads 170,171 to the electrodes 157, 158. Also depicted in this preferred embodiment are two banks of impedance sensors 172,173 that may be used fluid detection (e.g., sample, reagents, wash, buffer, etc.) and/or fluid discrimination (e.g., discriminating between sample, reagents, wash, buffer, etc. and/or sample type such as whole blood, plasma, mucous, etc.).

Figure 1C:
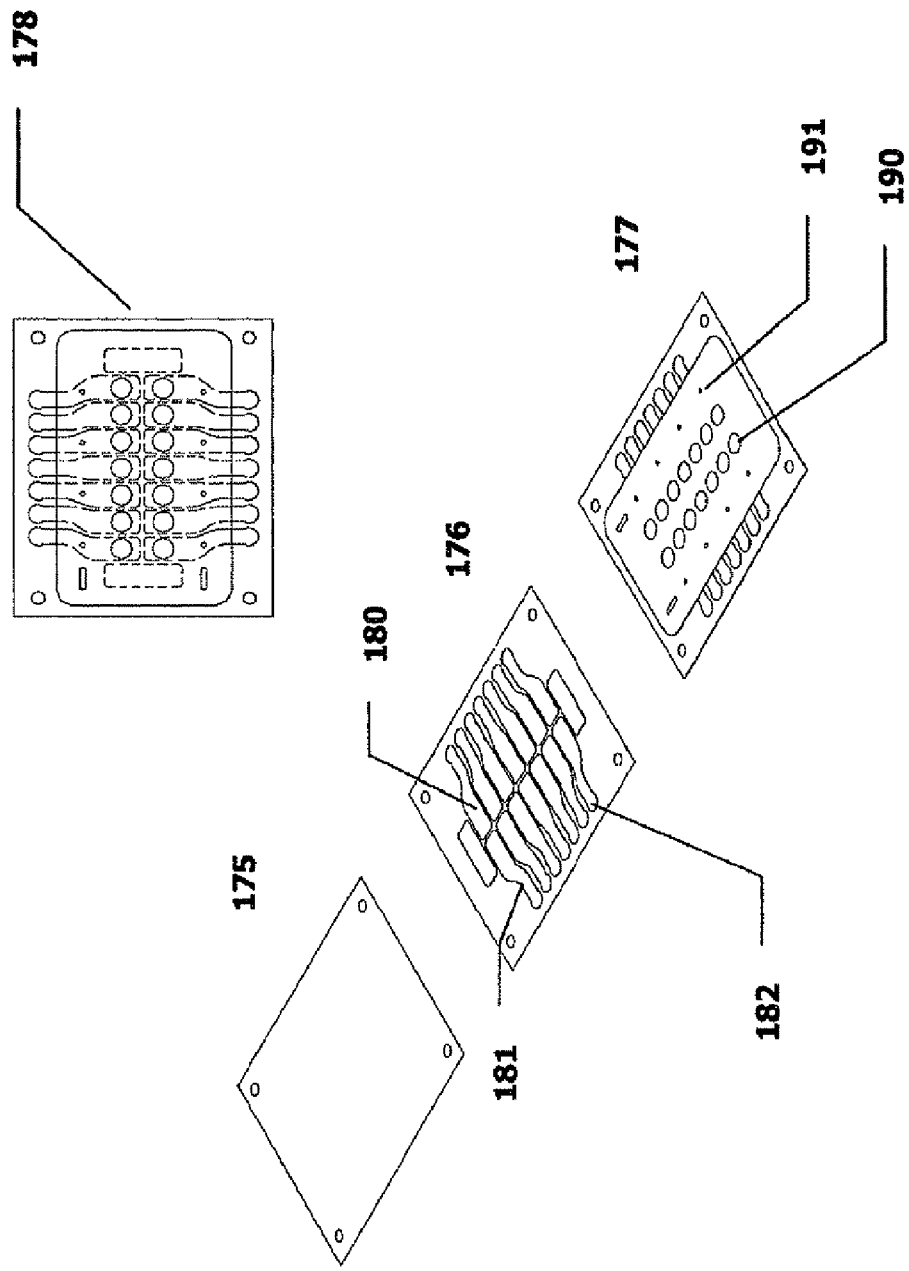
FIG. 1c illustrates an exploded assembly of one embodiment of an electrode array.

FIG. 1c is an assembly schematic for one preferred embodiment illustrating the assembly of cartridge component 178 comprising an electrode array 176. According to one embodiment, electrode array 176 (preferably, comprised of carbon ink) is applied to the substrate layer 175 forming the electrode 180, electrical lead 181 and electrical contact 182 portions. A dielectric layer 177 is preferably applied over the electrode layer to define the assay domains 190 and the impedance sensors 191. Alternately, electrical contacts 182 could be printed on the opposing side of the substrate and connected to electrodes 180 or electrical leads 181 via conductive through-holes through the substrate. Methods for applying the carbon and dielectric layers as well as various alternative materials are discussed below in greater detail.

Cartridge component 178 is, preferably, mated with a second cartridge component. The second cartridge component has channels or apertures arranged on the mating surface so that when mated to cartridge component 178 it acts to form detection chambers over the electrode arrays (e.g., as illustrated by detection chambers 155 and 156 in FIG. 1b and detection chamber 120 in FIG. 1a). Preferably, the second cartridge component has channels on the mating surface that form flow cells over the electrodes when mated to component 178 (the flow cells having one surface defined by component 178 and an opposing surface and wells defined by the second component. The channels may also be used to form other fluidic paths such as fluidic inlet and outlet lines to the flow cell. These channels may, e.g., be molded or cut into the second component. Alternatively, the walls of the flow cell or other fluidic paths may be defined by a gasket material preferably, double sided adhesive tape) applied between component 178 and the second cartridge component. Alternatively, the second component has apertures in the mating surface that form wells when mated to component 178.

In a preferred embodiment of the invention, an assay cartridge has minimal or no active mechanical or electronic components. When carrying out an assay, such an assay cartridge may be introduced into a cartridge reader which provides these functions. For example, a reader may have electronic circuitry for applying electrical energy to the assay electrodes and for measuring the resulting potentials or currents at assay electrodes. The reader may have one or more light detectors for measuring luminescence generated at assay electrodes. Light detectors that may be used include, but are not limited to photomultiplier tubes, avalanche photodiodes, photodiodes, photodiode arrays, CCD chips, CMOS chips, film. The light detector may be comprised within an optical detection system that also comprise lenses, filters, shutters, apertures, fiber optics, light guides, etc. The reader may also have pumps, valves, heaters, sensors, etc. for providing fluids to the cartridge, verifying the presence of fluids and/or maintaining the fluids at an appropriate controlled temperature. The reader may be used to store and provide assay reagents, either onboard the reader itself or from separate assay reagent bottles or an assay reagent storage device. The reader may also have cartridge handling systems such as motion controllers for moving the cartridge in and out of the reader. The reader may have a microprocessor for controlling the mechanical and/or electronic subsystems, analyzing the acquired data and/or providing a graphical user interface (GUI). The cartridge reader may also comprise electrical, mechanical and/or optical connectors for connecting to the cartridge.

One aspect of the invention relates to the assay modules employing electrodes, the immobilization of assay reagents on these electrodes, and their use in assays, preferably electrode-induced luminescence assays. Co-pending U.S. patent application Ser. No. 10/185,274, filed Jun. 28, 2002, hereby incorporated by reference, provides a number of examples of electrode and dielectric materials, electrode patterns and patterning techniques and immobilization techniques that are adapted for use in electrode-induced luminescence assays and suitable for use with the assay modules of the invention. Electrodes in the present invention are preferably comprised of a conductive material. The electrode may comprise a metal such as gold, silver, platinum, nickel, steel, iridium, copper, aluminum, a conductive alloy, or the like. They may also comprise oxide coated metals (e.g. aluminum oxide coated aluminum). Electrodes may comprise non-metallic conductors such as conductive forms of molecular carbon. Electrodes may also be comprised of semiconducting materials (e.g. silicon, germanium) or semi-conducting films such as indium tin oxide (ITO), antimony tin oxide (ATO) and the like. Electrodes may also be comprised of mixtures of materials containing conductive composites, inks, pastes, polymer blends, metal/non-metal composites and the like. Such mixtures may include conductive or semi-conductive materials mixed with non-conductive materials. Preferably, electrode materials are substantially free of silicone-based materials.

Electrodes (in particular working electrodes) used in assay modules of the invention are advantageously able to induce luminescence from luminescent species. Preferable materials for working electrodes are materials able to induce electrochemiluminescence from ruthenium-tris-bipyridine in the presence of tertiary alkyl amines (such as tripropyl amine). Examples of such preferred materials include platinum, gold, ITO, carbon, carbon-polymer composites, and conductive polymers.

Preferably, electrodes are comprised of carbon-based materials such as carbon, carbon black, graphitic carbon, carbon nanotubes, carbon fibrils, graphite, carbon fibers and mixtures thereof. Advantageously, they may be comprised of conductive carbon-polymer composites, conductive particles dispersed in a matrix (e.g. carbon inks, carbon pastes, metal inks), and/or conductive polymers. One preferred embodiment of the invention is an assay module, preferably an assay cartridge, having electrodes (e.g., working and/or counter electrodes) that comprise carbon, preferably carbon layers, more preferably screen-printed layers of carbon inks. Some useful carbon inks include materials produced by Acheson Colloids Co. (e.g., Acheson 440B, 423ss, PF407A, PF407C, PM-003A, 30D071, 435A, Electrodag 505SS, and Aquadag™), E. I. Du Pont de Nemours and Co. (e.g., Dupont 7105, 7101, 7102, 7103, 7144, 7082, 7861D, E100735 62B and CB050), Advanced Conductive Materials (e.g., PTF 20), Gwen Electronics Materials (e.g., C2000802D2) and Conductive Compounds Inc (e.g., C-100), and Ercon Inc. (e.g., G-451, G-449 and 150401).

In another preferred embodiment, the electrodes of the invention comprise carbon fibrils. The terms "carbon fibrils", "carbon nanotubes", single wall nanotubes (SWNT), multi-wall nanotubes (MWNT), "graphitic nanotubes", "graphitic fibrils", "carbon tubules", "fibrils" and "buckeytubes", all of which terms may be used to describe a broad class of carbon materials (see Dresselhaus, M. S.; Dresselhaus, G.; Eklund, P. C.; "Science of Fullerenes and Carbon Nanotubes", Academic Press, San Diego, Calif., 1996, and references cited therein). The terms "fibrils" and "carbon fibrils" are used throughout this application to include this broad class of carbon-based materials. Individual carbon fibrils as disclosed in U.S. Pat. Nos. 4,663,230; 5,165,909; and 5,171,560 are particularly advantageous. They may have diameters that range from about 3.5 nm to 70 nm, and length greater than $10^2$ times the diameter, an outer region of multiple, essentially continuous, layers of ordered carbon atoms and a distinct inner core region. Simply for illustrative purposes, a typical diameter for a carbon fibril may be approximately between about 7 and 25 nm, and a typical range of lengths may be 1000 nm to 10,000 nm. Carbon fibrils may also have a single layer of carbon atoms and diameters in the range of 1 nm-2 nm. Electrodes of the invention may comprise one or more carbon fibrils, e.g., in the form of a fibril mat, a fibril aggregate, a fibril ink, a fibril composite (e.g., a conductive composite comprising fibrils dispersed in an oil, paste, ceramic, polymer, etc.).

Electrodes may be formed into patterns by a molding process (i.e., during fabrication of the electrodes), by patterned deposition, by patterned printing, by selective etching, through a cutting process such as die cutting or laser drilling, and/or by techniques known in the art of electronics microfabrication. Electrodes may be self supporting or may be supported on another material, e.g. on films, plastic sheets, adhesive films, paper, backings, meshes, felts, fibrous materials, gels, solids (e.g. metals, ceramics, glasses), elastomers, liquids, tapes, adhesives, other electrodes, dielectric materials and the like. The support, or substrate, may be rigid or flexible, flat or deformed, transparent, translucent, opaque or reflective. Preferably, the support comprises a flat sheet of plastic such as acetate or polystyrene. Electrode materials may be applied to a support by a variety of coating and deposition processes known in the art such as painting, spray-coating, screen-printing, ink-jet printing, laser printing, spin-coating, evaporative coating, chemical vapor deposition, etc. Supported electrodes may be patterned using photolithographic techniques (e.g., established techniques in the microfabrication of electronics), by selective etching, and/or by selective deposition (e.g., by evaporative or CVD processes carried out through a mask). In a preferred embodiment, electrodes are comprised of extruded films of conducting carbon/polymer composites. In another preferred embodiment, electrodes are comprised of a screen printed conducting ink deposited on a substrate. Electrodes may be supported by another conducting material. In some applications, screen printed carbon ink electrodes are printed over a conducting metal ink (e.g., silver ink) layer so as to improve the conductivity of the electrodes. Preferably, in assay cartridges, a miniaturized design allows the use of electrodes having short printed electrode leads (preferably less than 1.5 cm, more preferably less than 1.0 cm) that are relatively similar in length. By keeping the leads short, it is possible to use screen printed carbon electrodes without an underlying conductive metal layer such as a silver layer.

According to one preferred embodiment of the invention, the electrode surface (preferably a working electrode surface of an assay module or assay plate) is bounded by a dielectric surface, the dielectric surface being raised or lowered preferably, raised) and/or of different hydrophobicity (preferably, more hydrophobic) than the electrode surface. Preferably, the dielectric boundary is higher, relative to the electrode surface, by 0.5-100 micrometers, or more preferably by 2-30 micrometers, or most preferably by 8-12 micrometers. Even more preferably, the dielectric boundary has a sharply defined edge (i.e., providing a steep boundary wall and/or a sharp angle at the interface between the electrode and the dielectric boundary).

Preferably, the first electrode surface has an advancing contact angle for water 10 degrees less than the dielectric surface, preferably 15 degrees less, more preferably 20 degrees less, more preferably 30 degrees less, even more preferably 40 degrees less, and most preferred 50 degrees less. One advantage of having a dielectric surface that is raised and/or more hydrophobic than the electrode surface is in the reagent deposition process where the dielectric boundary may be used to confine a reagent within the boundary of the electrode surface. In particular, having a sharply defined edge with a steep boundary wall and/or a sharp angle at the interface between the electrode and dielectric boundary is especially useful for "pinning" drops of solution and confining them to the electrode surface. In an especially preferred embodiment of the invention, the dielectric boundary is formed by printing a patterned dielectric ink on and/or around the electrode, the pattern designed so as to expose one or more assay domains on the electrode.

Electrodes may be modified by chemical or mechanical treatment to improve the immobilization of reagents. The surface may be treated to introduce functional groups for immobilization of reagents or to enhance its adsorptive properties. Surface treatment may also be used to influence properties of the electrode surface, e.g., the spreading of water on the surface or the kinetics of electrochemical processes at the surface of the electrode. Techniques that may be used include exposure to electromagnetic radiation, ionizing radiation, plasmas or chemical reagents such as oxidizing agents, electrophiles, nucleophiles, reducing agents, strong acids, strong bases and/or combinations thereof. Treatments that etch one or more components of the electrodes may be particularly beneficial by increasing the roughness and therefore the surface area of the electrodes. In the case of composite electrodes having conductive particles or fibers (e.g., carbon particles or fibrils) in a polymeric matrix or binder, selective etching of the polymer may be used to expose the conductive particles or fibers.

One particularly useful embodiment is the modification of the electrode, and more broadly a material incorporated into the present invention by treatment with a plasma, specifically a low temperature plasma, also termed glow-discharge. The treatment is carried out in order to alter the surface characteristics of the electrode, which come in contact with the plasma during treatment. Plasma treatment may change, for example, the physical properties, chemical composition, or surface-chemical properties of the electrode. These changes may, for example, aid in the immobilization of reagents, reduce contaminants, improve adhesion to other materials, alter the wettability of the surface, facilitate deposition of materials, create patterns, and/or improve uniformity. Examples of useful plasmas include oxygen, nitrogen, argon, ammonia, hydrogen, fluorocarbons, water and combinations thereof. Oxygen plasmas are especially preferred for exposing carbon particles in carbon-polymer composite materials. Oxygen plasmas may also be used to introduce carboxylic acids or other oxidized carbon functionality into carbon or organic materials (these may be activated, e.g., as active esters or acyl chlorides) so as to allow for the coupling of reagents. Similarly, ammonia-containing plasmas may be used to introduce amino groups for use in coupling to assay reagents.

Treatment of electrode surfaces may be advantageous so as to improve or facilitate immobilization, change the wetting properties of the electrode, increase surface area, increase the binding capacity for the immobilization of reagents (e.g., lipid, protein or lipid/protein layers) or the binding of analytes, and/or alter the kinetics of electrochemical reactions at the electrode. In some applications, however, it may be preferable to use untreated electrodes. For example, we have found that it is advantageous to etch carbon ink electrodes prior to immobilization when the application calls for a large dynamic range and therefore a high binding capacity per area of electrode. We have discovered that oxidative etching (e.g., by oxygen plasma) has additional advantages in that the potential for oxidation of tripropyl amine (TPA) and the contact angle for water are both reduced relative to the unetched ink. The low contact angle for water allows reagents to be adsorbed on the electrode by application of the reagents in a small volume of aqueous buffer and allowing the small volume to spread evenly over the electrode surface. Surprisingly, we have found that excellent assays may also be carried out on unetched carbon ink electrodes despite the presence of polymeric binders in the ink. In fact, in some applications requiring high sensitivity or low-non specific binding it is preferred to use unetched carbon ink electrodes so as to minimize the surface area of exposed carbon and therefore minimize background signals and loss of reagents from non-specific binding of reagents to the exposed carbon. Depending on the ink used and the process used to apply the ink, the electrode surface may not be easily wettable by aqueous solutions. We have found that we can compensate for the low wettability of the electrodes during the adsorption of reagents by adding low concentrations of non-ionic detergents to the reagent solutions so as to facilitate the spreading of the solutions over the electrode surface. Even spreading is especially important during the localized immobilization of a reagent from a small volume of solution. For example, we have found that the addition of 0.005-0.04% Triton X-100® allows for the spreading of protein solutions over unetched carbon ink surfaces without affecting the adsorption of the protein to the electrode and without disrupting the ability of a dielectric film applied on or adjacent to the electrode (preferably, a printed dielectric film with a thickness of 0.5-100 micrometers, or more preferably 2-30 micrometers, or most preferably 8-12 micrometers and having a sharply defined edge) to confine fluids to the electrode surface. Preferably, when non-ionic detergents such as Triton X-100® are used to facilitate spreading of reagents (e.g., capture reagents) onto unetched screen-printed electrodes (i.e., so as to allow the immobilization of the reagents), the solutions containing the reagents are allowed to dry onto the electrode surface. It has been found that this drying step greatly improves the efficiency and reproducibility of the immobilization process.

The efficiency of the immobilization of reagents on carbon ink electrodes, especially unetched carbon ink electrodes, may exhibit some variability due to different levels of contamination of the electrodes surface. This effect is particularly pronounced when certain dielectric inks are used to form assay domains on the electrodes. We have found that we can improve the immobilization efficiencies and lower the variability by pre-washing the electrode surfaces, preferably with a surfactant solution.

The contamination of carbon ink electrodes by certain dielectric inks was observed by quantitatively assessing the surface wetting properties of the electrodes by measuring the contact diameter, where the larger the contact diameter, the better the wetting. A comparison of three alternative carbon surfaces with different dielectric layers is depicted in Table 1. As shown by the data in Table 1, washing the electrode surfaces can significantly increase the wetting properties (contact diameter) of carbon surfaces contacting the 451 dielectric (presumably by removing contamination of the electrode surface associated with the printing of the 451 dielectric, e.g., by migration of components of the dielectric ink on to the electrode surface).

TABLE 1

Comparison of Contact Diameters on Carbon Electrode Surfaces for Three Different Dielectric Materials (Mean 50 nL water drop diameter at 400 µs open time)

| Surface | Contact Diameter, inches * |
|---|---|
| No pre-treatment: | |
| Carbon with 451 dielectric | 0.0366 |
| Carbon with Nazdar dielectric | 0.0461 |
| Carbon with PD039A dielectric | 0.0457 |
| Pre-treated: | |
| Carbon with 451 dielectric | 0.0438 |
| Carbon with Nazdar dielectric | 0.0463 |
| Carbon with PD039A dielectric | 0.0448 |

In one embodiment, a method of decontaminating the carbon electrode surfaces may be employed wherein the electrode surfaces are soaked in an aqueous 0.5% Triton X-100 solution for several hours, subsequently rinsed with deionized water, then soaked in deionized water for approximately one hour and finally dried. The Triton solution preferably removes the contaminants from the surface and the deionized water removes the adsorbed surfactant. This method of decontamination is an effective cleaning procedure that enhances the differences between the retreating contact angles on the carbon and the dielectric inks.

Figure 6A:
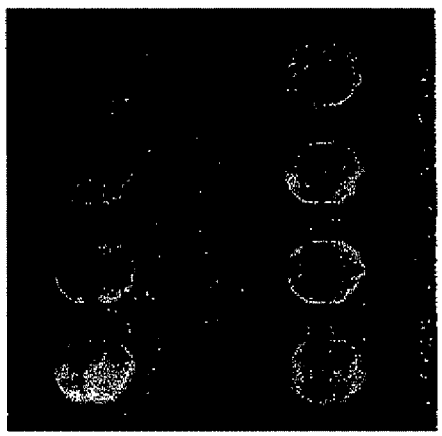
FIGS. 6a and 6b are images of electrochemiluminescence from electrode arrays that are untreated (FIG. 6a) or that have been pre-washed with a surfactant (FIG. 6b).
Figure 6B:
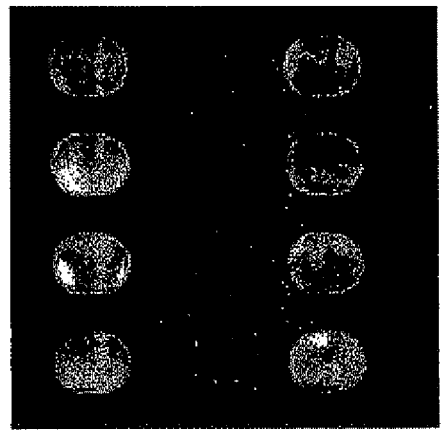

FIG. 6 demonstrates the results of the decontamination procedure. Specifically, FIG. 6 depicts images of ECL from an ECL label over carbon ink electrodes, the exposed areas of the electrode being defined by a dielectric film. FIG. 6a is the ECL image without decontamination and FIG. 6b is the ECL image after decontamination with Triton X-100 in accordance with the present embodiment. These ECL images show that the treatment process greatly reduces the variation in ECL intensity over the surface of the electrode, the patchiness of ECL on the untreated electrode presumably being caused by patches of contamination on the surface.

Electrodes can be derivatized with chemical functional groups that can be used to attach other materials to them. Materials may be attached covalently to these functional groups, or they may be adsorbed non-covalently to derivatized or underivatized electrodes. Electrodes may be prepared with chemical functional groups attached covalently to their surface. These chemical functional groups include but are not limited to COOH, OH, $NH_2$, activated carboxyls (e.g., N-hydroxy succinimide (NHS)-esters), poly-(ethylene glycols), thiols, alkyl (($CH_2)_n$) groups, and/or combinations thereof). Certain chemical functional groups (e.g., COOH, OH, $NH_2$, SH, activated carboxyls) may be used to couple reagents to electrodes. For further reference to useful immobilization and bioconjugation techniques see G. Hermanson, A. Mallia and P. Smith, *Immobilized Affinity Ligand Techniques* (Academic Press, San Diego, 1992) and G. Hermanson, *Bioconjugate Techniques* (Academic Press, San Diego, 1996).

In preferred embodiments, NHS-ester groups are used to attach other molecules or materials bearing a nucleophilic chemical functional group (e.g., an amine). In a preferred embodiment, the nucleophilic chemical functional group is present on and/or in a biomolecule, either naturally and/or by chemical derivatization. Examples of suitable biomolecules include, but are not limited to, amino acids, proteins and functional fragments thereof, antibodies, binding fragments of antibodies, enzymes, nucleic acids, and combinations thereof. This is one of many such possible techniques and is generally applicable to the examples given here and many other analogous materials and/or biomolecules. In a preferred embodiment, reagents that may be used for ECL may be attached to the electrode via NHS-ester groups.

It may be desirable to control the extent of non-specific binding of materials to electrodes. Simply by way of non-limiting examples, it may be desirable to reduce or prevent the non-specific adsorption of proteins, antibodies, fragments of antibodies, cells, subcellular particles, viruses, serum and/or one or more of its components, ECL labels (e.g., $Ru^{II}(bpy)_3$ and $R^{III}(bpy)_3$ derivatives), oxalates, trialkylamines, antigens, analytes, and/or combinations thereof). In another example, it may be desirable to enhance the binding of biomolecules.

One or more chemical moieties that reduce or prevent non-specific binding (also known as blocking groups) may be present in, on, or in proximity to an electrode. Such moieties, e.g., PEG moieties and/or charged residues (e.g., phosphates, ammonium ions), may be attached to or coated on the electrode. Examples of useful blocking reagents include proteins (e.g., serum albumins and immunoglobins), nucleic acids, polyethylene oxides, polypropylene oxides, block copolymers of polyethylene oxide and polypropylene oxide, polyethylene imines and detergents or surfactants (e.g., classes of non-ionic detergents/surfactants known by the trade names of Brij, Triton, Tween, Thesit, Lubrol, Genapol, Pluronic (e.g., F108), Tetronic, Tergitol, and Span).

Materials used in electrodes may be treated with surfactants to reduce non-specific binding. For example, electrodes may be treated with surfactants and/or detergents that are well known to one of ordinary skill in the art (for example, the Tween, Triton, Pluronics (e.g., F108), Span, and Brij series of detergents). Solutions of PEGs and/or molecules which behave in similar fashion to PEG (e.g., oligo- or polysaccharides, other hydrophilic oligomers or polymers) ("Polyethylene glycol chemistry: Biotechnical and Biomedical Applications", Harris, J. M. Editor, 1992, Plenum Press) may be used instead of and/or in conjunction with surfactants and/or detergents. Undesirable non-specific adsorption of certain entities such as those listed above may be blocked by competitive non-specific adsorption of a blocking agent, e.g., by a protein such as bovine serum albumin (BSA), casein or immunoglobulin G (IgG). One may adsorb or covalently attach an assay reagent on an electrode and subsequently treat the electrode with a blocking agent so as to block remaining unoccupied sites on the surface.

In preferred embodiments, it may be desirable to immobilize (by either covalent or non-covalent means) biomolecules or other assay reagents to carbon-containing materials, e.g., carbon inks, carbon black, fibrils, and/or carbon dispersed in another material. One may attach antibodies, fragments of antibodies, proteins, enzymes, enzyme substrates, inhibitors, cofactors, antigens, haptens, lipoproteins, liposaccharides, cells, sub-cellular components, cell receptors, viruses, nucleic acids, antigens, lipids, glycoproteins, carbohydrates, peptides, amino acids, hormones, protein-binding ligands, pharmacological agents, and/or combinations thereof. It may also be desirable to attach non-biological entities such as, but not limited to polymers, elastomers, gels, coatings, ECL tags, redox active species (e.g., tripropylamine, oxalates), inorganic materials, chelating agents, linkers, etc. A plurality of species may be co-adsorbed to form a mixed layer on the surface of an electrode. Most preferably, biological materials (e.g., proteins) are immobilized on carbon-containing electrodes by passive adsorption. Surprisingly, biological membranes (e.g., cells, cell membranes, membrane fragments, membrane vesicles, lipsomes, organelles, viruses, bacteria, etc.) may be directly adsorbed on carbon without destroying the activity of membrane components or their accessibility to binding reagents (see, e.g., copending U.S. patent application Ser. No. 10/208,526 (entitled "Assay Electrodes Having Immobilized Lipid/Protein Layers, Methods Of Making The Same And Methods Of Using The Same For Luminescence Test Measurements"), filed on Jul. 29, 2002, hereby incorporated by reference.

Electrodes used in the assay modules are, preferably, non-porous, however, in some applications it is advantageous to use porous electrodes (e.g., mats of carbon fibers or fibrils, sintered metals, and metals films deposited on filtration membranes, papers or other porous substrates. These applications include those that employ filtration of solutions through the electrode so as to: i) increase mass transport to the electrode surface (e.g., to increase the kinetics of binding of molecules in solution to molecules on the electrode surface); ii) capture particles on the electrode surface; and/or iii) remove liquid from the well.

Preferred assay modules may use dielectric inks, films or other electrically insulating materials (hereinafter referred to as dielectrics). Dielectrics in the present invention may be used to prevent electrical connectivity between electrodes, to define patterned regions, to adhere materials together (i.e., as adhesives), to support materials, to define assay domains, as masks, as indicia and/or to contain assay reagents and other fluids. Dielectrics are non-conducting and advantageously non-porous (i.e., do not permit transmission of materials) and resistant to dissolving or degrading in the presence of media encountered in an electrode induced luminescence measurement. The dielectrics in the present invention may be liquids, gels, solids or materials dispersed in a matrix. They may be deposited in uncured form and cured to become solid. They may be inks, solid films, tapes or sheets. Materials used for dielectrics include polymers, photoresists, plastics, adhesives, gels, glasses, non-conducting inks, non-conducting pastes, ceramics, papers, elastomers, silicones, thermoplastics. Preferably, dielectric materials of the invention are substantially free of silicones. Examples of non-conducting inks include UV curable dielectrics such as materials produced by Acheson Colloids Co. (e.g., Acheson 451SS, 452SS, PF-455, PD039A, PF-021, ML25251, ML25240, ML25265, and Electrodag 38DJB136 clear), Nazdar (e.g., Nazdar GS2081 3400SPL) and E. I. du Pont de Nemours and Co. (e.g., Dupont: 5018, 3571, and 5017).

Dielectrics, in accordance with certain preferred embodiments, may be applied by a variety of means, for example, printing, spraying, laminating, or may be affixed with adhesives, glues, solvents or by use of mechanical fasteners. Patterns and/or holes in dielectric layers may be formed by molding processes (i.e., during fabrication of the layer), by selective etching and/or by a cutting process such as die cutting or laser drilling. Dielectrics may be deposited and/or etched in patterns through the use of established photolithographic techniques (e.g., techniques used in the semiconductor electronics industry) and/or by patterned deposition using an evaporative or CVD process (e.g., by deposition through a mask). In a preferred embodiment, a dielectric ink is deposited on a substrate by printing (e.g., ink jet printing, laser printing or, more preferably, screen printing) and, optionally, UV cured. Preferably, the screen printed dielectric is UV curable allowing for improved edge definition than solvent based dielectrics. In another preferred embodiment, a non-conducting polymeric film is affixed to a support using an adhesive.

When using a dielectric ink printed on, or adjacent to, an electrode to confine fluids to regions of the electrode surface, the dielectric film preferably has a thickness of 0.5-100 micrometers, or more preferably 2-30 micrometers, or most preferably 8-12 micrometers and also, preferably, has a sharply defined edge with steep walls.

Miniaturization of various components and processes required to support ECL-based assays can also benefit from novel approaches to induce ECL. When inducing ECL, the working electrode and a counter electrode are, preferably, spaced relatively close to one another to minimize the effect of voltage drops in solution on the intensity and spatial distribution of ECL signals. When multiple ECL measurements are to be made in the same solution volume, each measurement, preferably, uses a closely spaced working electrode (where electrochemiluminescence is induced) and a counter electrode (to complete the electrochemical circuit). One possible configuration is for each measurement to have its own pair of electrodes; however, this configuration would require the largest volume, space, and number of electrical contacts on the device. An alternative configuration is for each measurement to share a common counter electrode that is reused. FIGS. 3f and 3g illustrate possible alternative approaches for using common counter electrodes. As can be seen, the detection chambers (e.g., detection chamber 341) for such configurations would still require a large space in order to accommodate both the working electrodes (e.g., working electrode 315) and the single, common counter electrode 311. Moreover, the relative size and spacing of each working electrode-counter electrode pair will affect the relative performance of each pair. Therefore, as depicted in FIGS. 3f and 3g configurations employing a single, common counter electrode would preferably ensure that the relative size and spacing of each working-counter electrode pair is approximately equal. Preferably, the working electrodes are arranged in a one dimensional array, the array being preferably arranged along the flow path of a flow cell. The common counter electrode is also, preferably aligned with the flow path to one side of the array so as to maintain approximate equal spacing to each of the working electrodes. Preferably, no working electrode is located in the shortest path between the counter electrode and a different working electrode; application of a large potential between the counter electrode and a first working electrode can under some conditions generate high enough potentials in the intervening solution to trigger an undesired emission of ECL at a second working electrode located in the shortest path between the first working electrode and the counter electrode. Optionally, the electrode surface area in contact with the detection chamber is defined by an aperture in a dielectric film deposited on the electrode layer (shown as circles on the electrode layer).

In one preferred embodiment, an electrode pair-wise firing scheme can be employed in order to miniaturize the cartridge to the largest extent practicable, and therefore greatly reduce the volume and space required. This preferred pair-wise firing scheme, or electrode-pairing scheme, would preferably employ a sacrificial, or dedicated counter electrode for the first measurement and thereafter allow the reuse of a previously fired (where fired describes the state of the surface after the application of a working electrode potential, e.g., a potential sufficient to generate electrochemiluminescence at a working electrode) working electrode as the next counter electrode for the next measurement. Surprisingly, as discussed below, it was observed that neither having a protein coating on the electrode being used as the counter electrode nor the fact that the electrode was already fired once as a working electrode affected the performance of that electrode for use as a counter electrode, thus allowing the use of electrodes in a dual-role as both working and counter electrodes.

Figures 3A, 3B:
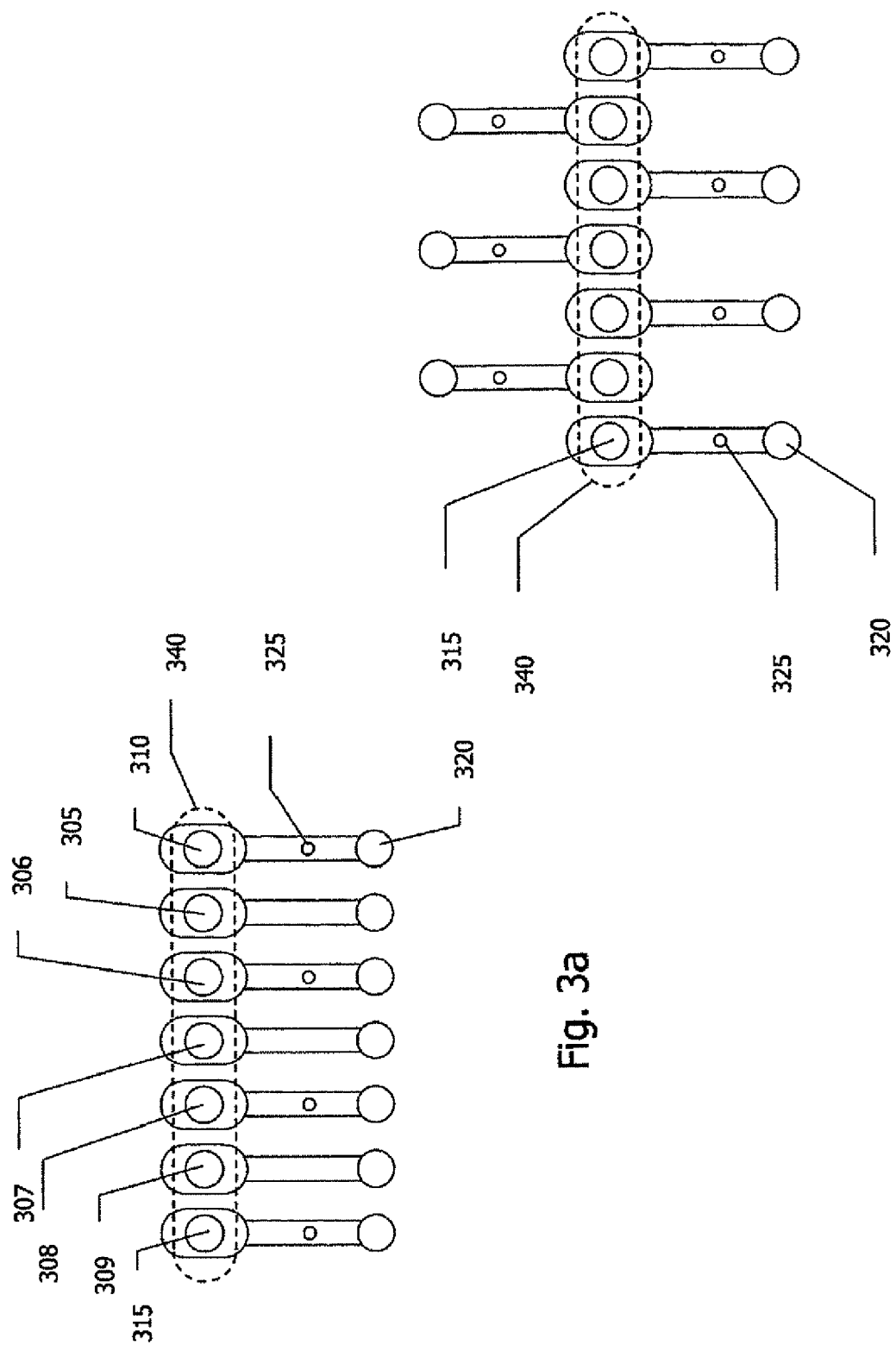

FIGS. 3a-3e depict possible alternative configurations for electrode arrays employing the pair-wise firing scheme. FIG. 3a illustrates a single bank of electrodes that can be used in one or more detection chambers (a single detection chamber 340 is indicated here by the dotted line). The electrodes are preferably arranged in a one dimensional array. Optionally, the electrode surface area in contact with the detection chamber is defined by an aperture in a dielectric film deposited on the electrode layer (shown as circles on the electrode layer). In one embodiment, electrode 310 may be configured as the dedicated counter electrode, electrodes 305-309 may be configured as the dual-role electrodes and electrode 315 may be configured as the dedicated working electrode. The electrode bank has impedance sensors 325 on leads to the electrodes which can be arranged to contact fluid in input or outlet lines to the detection chamber. Preferably, the impedance sensors are defined by apertures in a dielectric layer deposited on the electrode layer. The electrode array of FIG. 3a utilizes a configuration wherein the electrical contacts and leads are located to one side of the electrodes allowing for simplified mating with the control unit. FIG. 3b depicts an alternative configuration wherein the electrical contacts and leads are alternately placed on either side of the electrodes. Such an alternating configuration can allow for the impedance sensors to be placed on each of the electrical leads so as to allow interrogation of the fluids during both ingress and egress from the detection chamber (e.g., by arranging the fluid inlet line and fluid outlet line so that they, respectively, contact impedance sensors on alternate sides of the electrodes).

Figure 3C:
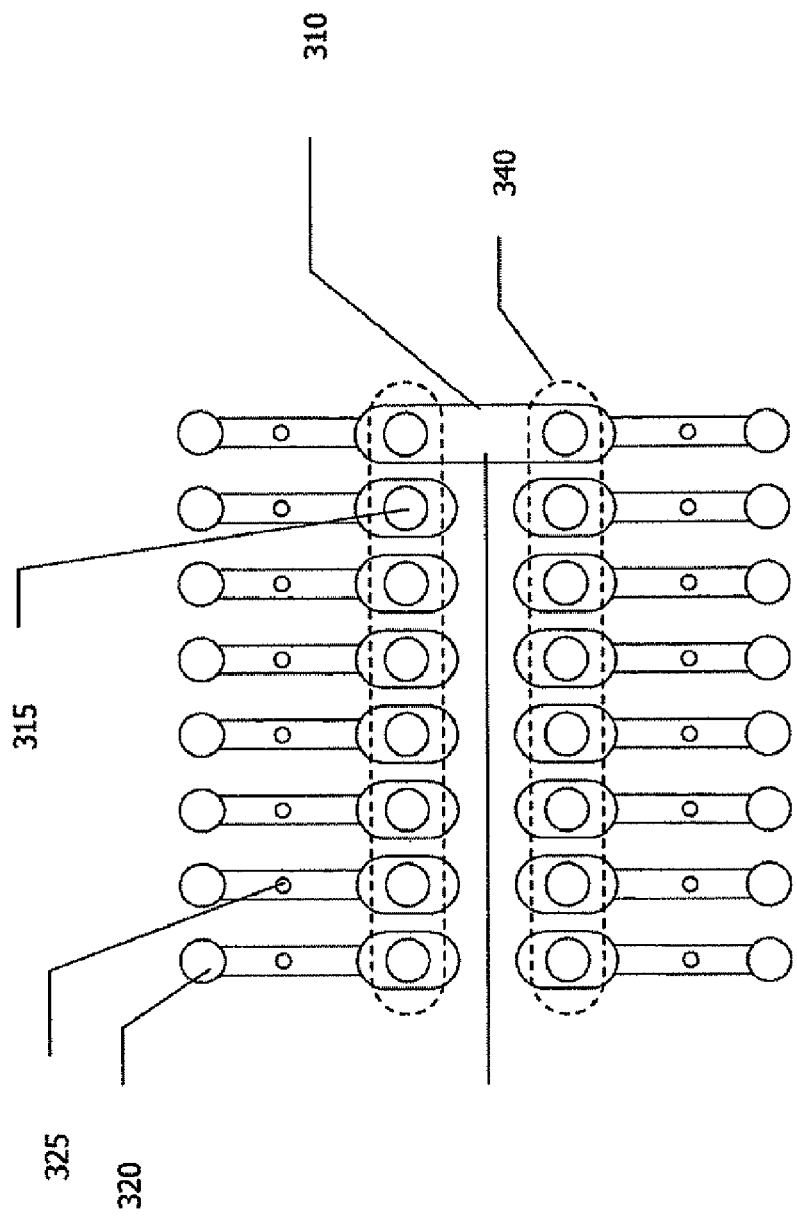
Figure 3F:
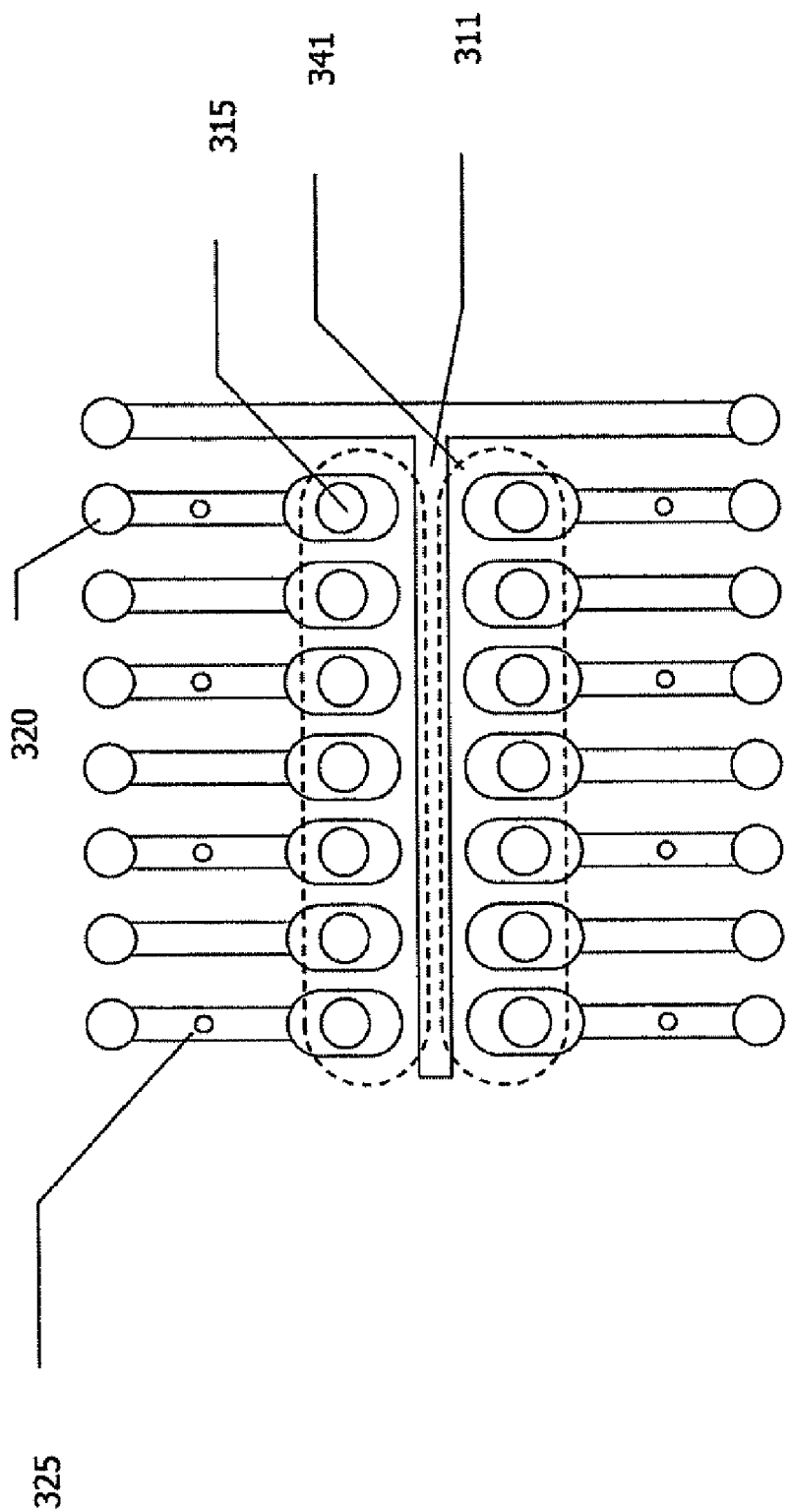
FIGS. 3f-3g illustrate two possible configurations of an electrode array employing a single, common counter electrode.
Figure 3G:
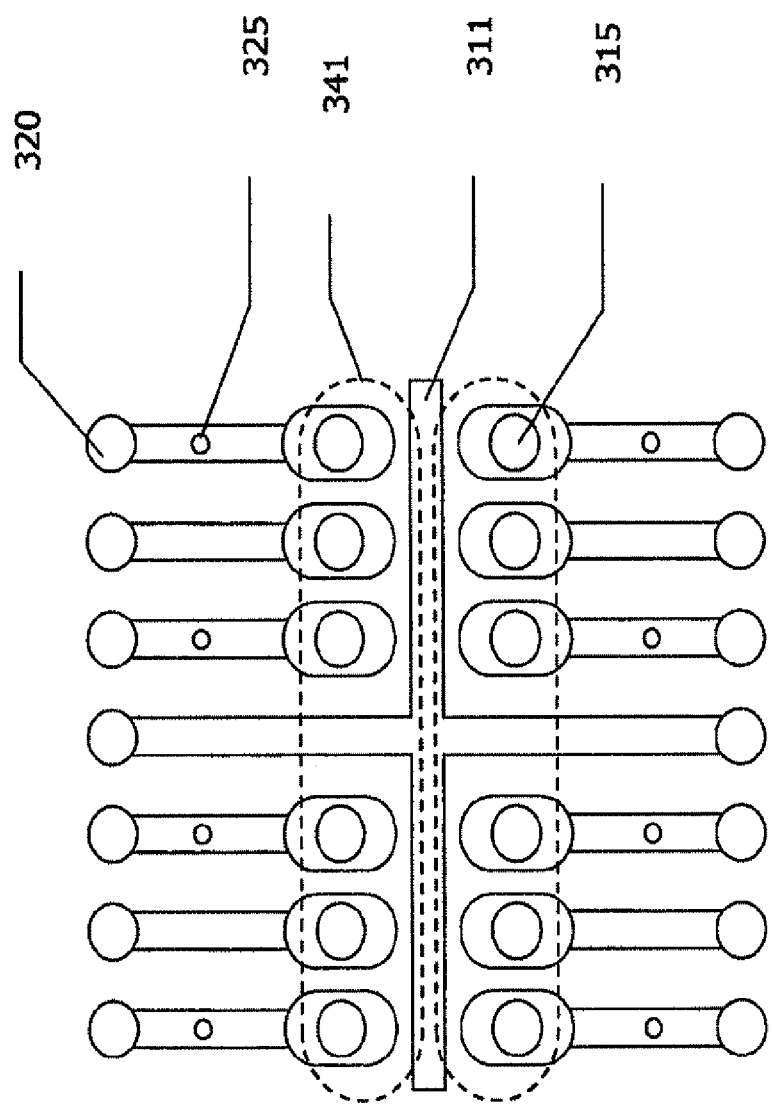

FIGS. 3c-3e illustrate configurations employing multiple detection chambers. In particular, FIGS. 3c and 3d depict two detection chambers employing two banks of electrodes. FIG. 3d illustrates a configuration wherein the electrodes for one set of contacts/leads are within the oppositely placed detection chamber. Such a configuration may provide added benefits such as a more densely packed electrode array and the ability to place impedance sensors on each lead. Impedance sensors may be placed on each lead since each detection chamber can be alternately processed; i.e., fluid is first directed to on detection chamber and all assays are performed and then fluid is directed to the other detection chamber for processing of the remaining assays.

FIG. 3e depicts an embodiment utilizing four detection chambers. It should be noted that while FIG. 3e depicts an electrode array employing a single, common counter electrode in each detection chamber, such a configuration can also be employed using the pair-wise firing scheme discussed above.

Preferably, the electrode arrays depicted in FIGS. 3a-3g are supported on a support such as a plastic film or sheet. The detection chambers are, preferably, formed by mating the support to a second cartridge component having channels or apertures defined thereon (optionally, these features being at least partially defined by a gasket between the electrode support and the second cartridge component); see the discussion of FIG. 1c.

Since it was believed that using the electrode-pairing scheme might result in the assay on a previously used working electrode affecting its function as the counter electrode for the next working electrode, an experiment was devised wherein three different protein coatings were used to determine their effect. The effects of three protein coatings were measured: avidin, CK-MB capture antibody, and Bovine IgG. The ECL of a 10 nM ruthenium-tris-bipyridine solution in a tripropyl amine-containing buffer was measured on non-coated electrodes with various counter electrodes (coated, non-coated, fired, and virgin); these results are listed in Table 2. In this table $ECL_{fired\ CE}$ denotes the ECL from the working electrode when paired with a counter electrode that has been previously fired as a working electrode and $ECL_{virgin\ CE}$ is for ECL from the working electrode when paired with a counter electrode that has not been previously fired as a working electrode. The observed ECL signals were all within experimental error of one another demonstrating the unexpected result that neither the presence of protein on the surface nor the prior use as a working electrode had any affect on the performance of that surface as a counter electrode.

TABLE 2

Effects of Protein Coating and Application of Oxidative Potentials to Electrodes Previously Used as a Counter Electrode in Free TAG ECL Generation

| Protein on C.E. | $ECL_{fired\ CE}$ | $ECL_{virgin\ CE}$ |
|---|---|---|
| anti-CK-MB | 199 | 207 |
| Blank | 199 | 197 |
| Avidin | 181 | 205 |
| IgG | 203 | 214 |

Figure 4:
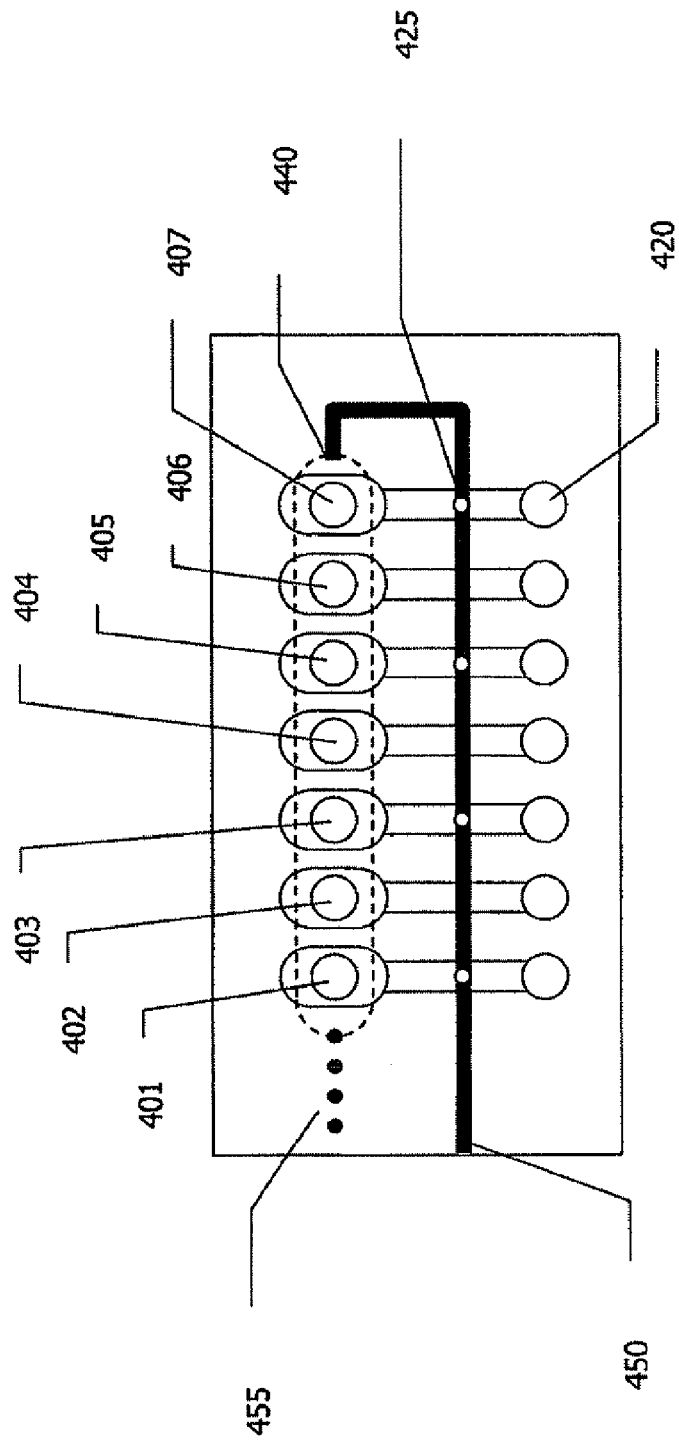
FIG. 4 depicts the electrode array of FIG. 3a in one embodiment of an assay cartridge.

With reference to FIG. 4, and by way of example only, operation of a simplified electrode array employing the pair-wise firing scheme within a single detection chamber will be described. For purposes of this operational example, introduction of sample, assay reagent(s), wash solution(s) and/or buffer(s) through the fluid input line 450 will not be discussed; it is to be understood that each of the necessary constituents for performing the assay are present in the detection chamber for this example. At least one of the electrodes will operate as a dedicated counter electrode, e.g., 401, and will therefore not have any assay reagents immobilized thereon. Electrodes 402-407 will have assay reagents immobilized thereon; electrodes 402-406 are to be used as dual-role electrodes and electrode 407 is to be used as a dedicated working electrode. As pictured in the figure, the electrodes are preferably arranged in one dimensional arrays (most preferably, linear arrays) along the fluid path in the detection chamber. The dedicated counter electrode 401 will be used first in conjunction with the adjacent dual-role electrode 402, wherein the dual-role electrode will be operated as a working electrode to perform the desired assay at dual-role electrode 402. Thereafter, dual-role electrode 402 will be operated as a counter electrode and will be pair-wise fired with dual-role electrode 403, wherein dual-role electrode 403 will be operated as a working electrode to perform the desired assay at dual-role electrode 403. This pair-wise firing is continued for the remaining electrodes until electrode pair 406 and 407. This last remaining pair will operate dual-role electrode 406 as a counter electrode and dedicated working electrode 407 as a working electrode to perform the desired assay at dedicated working electrode 407. Preferably, the electrode pairs used in a specific firing are adjacent each other (i.e., there are no other electrodes located between them) to avoid the undesired emission of ECL from an electrode located in the intervening space.

The use of patterned electrodes in cartridges may impose certain unique design and/or performance constraints. In particular, the use of patterned electrode leads may lead to problems associated with voltage drops along the leads, especially in applications like electrochemiluminescence that often require relatively high currents. The problems are often greatest when using electrodes comprising thin layers of only moderately conductive materials such as carbon inks. The problem may be partially mitigated by use of multi-layer patterned electrodes (where the conductivity of an exposed moderately conductive material such as a carbon ink is increased by printing it over a more conductive material such as a silver ink) although this approach introduces additional manufacturing steps. Alternatively, the problem may be partially mitigated in systems having multiple assay electrodes by keeping the leads short (preferably, so that the resistance between the electrode and the electrical contact is less than 500 ohms, more preferably less than 300 ohms, most preferably less than 100 ohms) to minimize the voltage drop and by keeping the leads about the same length to make the voltage drop consistent from electrode to electrode.

In an assay module comprising multiple working electrodes, the variability from electrode to electrode in the voltage drop across the electrode leads is preferably smaller than the potential applied during the course of an assay measurement so that this variability has minimal effect on the variability of the measurements. In especially preferred embodiments, the variability in voltage drop across the leads is less than 20% of the potential applied during the course of an assay measurement, more preferably less than 10% or most preferably less than 2%. Alternatively, the uniformity in leads can be described in terms of the variation in resistance across the leads which is preferably less than 50 ohms, more preferably less than 10 ohms, most preferably less than 1 ohm.

Where the arrangement of the electrodes and/or contacts makes it difficult to keep the leads a uniform length, the matching of lead resistances can be accomplished by geometrically matching the length-to-width ratio of each electrode lead (assuming consistent print thickness). This length-to-width ratio is referred to hereinafter as the "number of squares". Typically, for a preferred cartridge-based configuration using screen printed carbon inks, the electrode leads are on the order of 4 to 5 squares. Commercially available inks typically have ink resistances that are specified in resistance per square per thickness (e.g., ohms/square/mil) and can vary widely depending on the ink selected. In a particularly preferred embodiment, a carbon ink is used that possesses an ink resistance that measures approximately 15 ohms/square/mil. The total resistance measured from end-to-end across a lead for one preferred embodiment is typically on the order of 450 ohms for a configuration utilizing a 5 squares lead.

Figure 2:
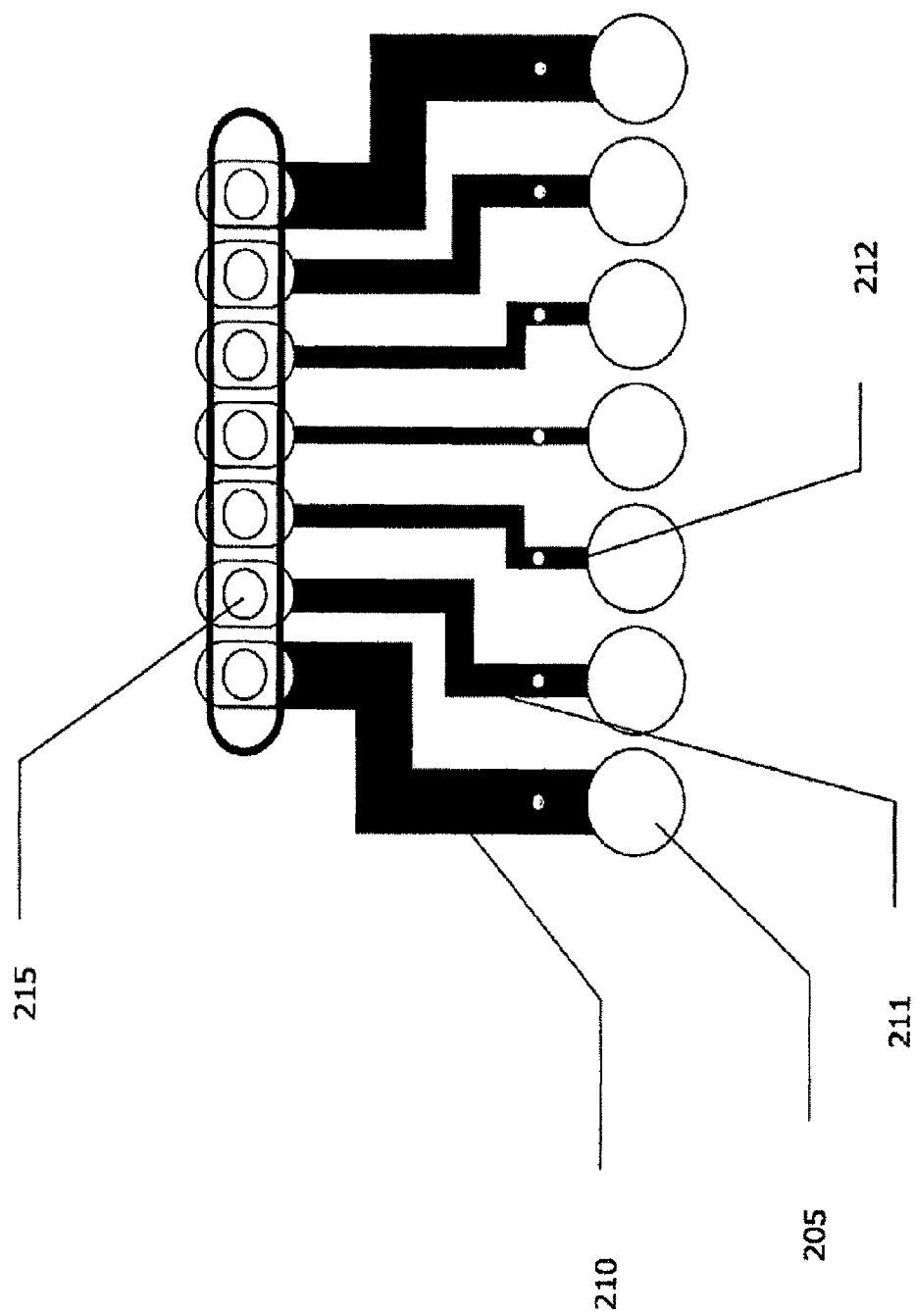
FIG. 2 is a pictorial representation of an electrode array having matched electrical lead resistances.

FIG. 2 depicts one preferred embodiment of an addressable electrode array for generating ECL that can be incorporated into a cartridge-based form factor having the requisite provisioning for sample/reagent mixing/delivery. As illustrated, contacts 205 and leads 210 are used to allow electrodes 215 in the addressable electrode array to be controlled by a control unit (not shown) adapted to contact, or mate, with the cartridge. Since the resistance across leads 210 represents a large fraction of the total cell resistance during an assay measurement, it is preferable to match the resistance across each lead as closely as possible. As shown in the figure, the length of the leads varies according to the positioning of the electrodes and contacts, however, the width is varied so that the length to width ratio of the leads is kept constant so as to provide a uniform lead resistance (the widths in the figure are not to scale and have been exaggerated for emphasis).

Utilization of the electrode array for multiple purposes contributes to a miniaturized cartridge-based device since the need for additional components is obviated. According to another aspect of the present invention, the electrode array may advantageously also be used for detecting the presence of fluid, for the detection of trapped air and/or for the identification of sample type. Preferably, an impedance measurement may be used to monitor the state of the cell during the cartridge routine. The measurement may assess whether there is trapped air on or above an electrode during incubation and after the wash step. Additionally, the impedance measurement may also allow usage of the electrode array to distinguish different sample types drawn into the cartridge, e.g., differentiate between samples of urine, saliva, serum, plasma, or whole blood, and make any necessary adjustments that may be needed.

The advantages associated with utilizing the electrode array to monitor cartridge operations by performing impedance measurements can be many fold. In particular, use of the electrode array in this manner affords a non-destructive measurement to be made since application of low voltage DC or, preferably, AC waveforms can be carried out with no effect on the subsequent ECL measurement. Also, the impedance measurement performed by the electrode array is relatively fast compared to other cartridge operations. Still further, the impedance measurement performed by the electrode array is very precise and can preferably be used in conjunction with other sensors; e.g., pressure, optical, etc.

At low voltages, the electrodes located in the region where detection is to be made, i.e., the read chamber, behave like a series RC circuit. This has proven to be a suitable model for the development of a fail safe mechanism to ascertain the presence of fluid, the presence of an unwanted bubble or to discriminate between sample specimen in types in the read chamber. In practice, it has been observed that trapped air may reside either on the electrode surface or in the solution bulk. According to the present invention, the location of the air with respect to the electrodes is important. According to one embodiment, a resistance measurement can be utilized to provide an indicator that is sensitive to air trapped in the bulk solution and at the electrode/solution interface. According to another embodiment, a capacitance measurement can be employed to provide an indicator that is primarily sensitive to air trapped at the interface. In yet another alternative embodiment, the electrochemical current during an ECL measurement (e.g., the TPA oxidation current during ECL) may be used to detect trapped air during the ECL measurement, however, this measurement would not provide information related to trapped air during the sample entry and incubation phases and would not allow corrective steps to be taken before the ECL measurement.

With respect to using a capacitance measurement, the pertinent capacitance is the double layer capacitance. Since the parallel plate capacitance is insignificant at frequencies below about 1 MHz, it is preferably ignored. Each electrode has a double layer capacitance. It is noted that the double layer capacitance is not a true capacitor, as it does exhibit a small frequency dependence. Advantageously the capacitance is primarily affected by changes at the interface (e.g., changes in the effective area of an electrode due to the trapping of an air bubble on the electrode surface), and not by the bulk; the capacitance is therefore preferably used to detect air bubbles at the electrode/solution interfaces. Preferably, the capacitance measurement uses an AC voltage input with a frequency between 10-40,000 Hz, more preferably between 20-2000 Hz, more preferably between 50-400 Hz, most preferably around 200 Hz. Other factors besides trapped air, e.g., errors in the printing of the electrodes, may change the effective area of an electrode and thus the measured capacitance. The measurement of capacitance can be used to check for these factors as well as for bubbles and can be used to trigger error flags if the capacitance values fall out of an acceptable range or, alternatively, to allow for normalization of the reported ECL signal to compensate for the actual electrode area.

With respect to using a resistance measurement, the pertinent resistances are the solution and lead resistances. It has been observed that the solution resistance will have a small frequency dependence. The resistance is affected by changes in the bulk solution (e.g., by bubbles interfering with the flow of current through bulk solution) and changes at the electrode/solution interface (e.g., trapped air at the interface has the affect of reducing the effective electrode area and therefore increasing the resistance). The solution resistance can also be expected to be very sensitive to the nature of the solution in contact with the electrodes and can also be used to identify the sample.

The resistive (in-phase) and capacitive (out-of phase) components of the impedance may be measured simultaneously using conventional impedance analyzing circuitry, preferably using a voltage waveform having a frequency at which both components have a significant effect on the impedance and/or a voltage waveform having a plurality of frequencies comprising at least one frequency where the resistance is a significant component of the impedance and at least one frequency where the capacitance is a significant component of the impedance. Alternatively, the resistive and capacitive components may be measured separately, preferably at frequencies that maximize the effect of the component being measured. For example, at high frequencies the effect of surface capacitance is minimized and the impedance is primarily due to solution resistance. In one embodiment of the invention, the solution resistance is measured by applying a voltage waveform having a frequency greater than 2000 Hz, more preferably between 2,000 and 100,000 Hz, most preferably around 20,000 Hz.

Sample matrix identification can be very important since certain biochemical assays may have varied steps or different post-processing requirements (e.g., the blood samples may be treated different than plasma samples). Tables 3 and 4 list resistance and capacitance values acquired for five different matrices by applying low voltage AC excitation to electrodes within an experimental cartridge. The electrode array comprised screen printed carbon ink electrodes, the exposed surface of which were defined by a patterned dielectric layer printed over the carbon ink. The impedance measurements were taken at 25 degrees C. using an excitation voltage equal to 0.010 V rms at the frequencies indicated in the tables. For capacitance measurements, since it is desirable to use a frequency where all (or nearly all) of the voltage drop occurs across the capacitive element, a frequency of 200 Hz was utilized as this was found to result in greater than 95% of the voltage drop to occur across the double layer capacitance; i.e., the solution losses were almost negligible. Resistance and capacitance were calculated using a series RC model.

As can be seen in Tables 3 and 4, the capacitance varied little between the different sample matrices, however, the resistances showed much greater variation among the matrices.

TABLE 3

Sample Discrimination Using Capacitance Measurements (phase angles 76 to 82 degrees).

| Matrix | Capacitance, uF at 200 Hz |
|---|---|
| assay buffer | 0.023 |
| saline | 0.021 |
| serum | 0.019 |
| plasma | 0.018 |
| blood | 0.020 |

TABLE 4

Sample Discrimination Using Resistance Measurements (includes 700 ohms of lead resistance; phase angles 12 to 16 degrees)

| Matrix | Resistance, ohms at 20,000 Hz |
|---|---|
| assay buffer | 2516 |
| saline | 3722 |
| serum | 3996 |
| plasma | 4158 |
| blood | 7039 |

Figure 5:
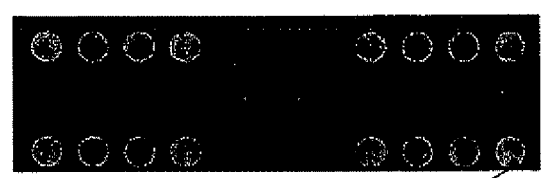
FIG. 5 is an image of electrochemiluminescence emitted from an electrode array where one of the electrodes has an air bubble on the electrode surface.

In certain preferred embodiments the electrochemical current measured during the induction of ECL, may be used to detect the presence of trapped air over an electrode since trapped air may cause a significant decrease in the electrochemical current (e.g., current from TPA oxidation during ECL). FIG. 5 depicts an image of ECL emitted from an electrode array. One of the electrodes has a small dark spot 500 due the presence of a small air bubble on the electrode surface. Even such a small bubble gave a detectable change in the electrochemical current measured at that electrode during the ECL experiment; the current in the presence of the air bubble (178 uA) was significantly different (by 5%) than the average of the current at the other electrodes (187 uA). Other factors besides trapped air, e.g., errors in the printing of the electrodes, may change the effective area of an electrode and thus the measured current. The measurement of current during ECL can be used to check for these factors as well as for bubbles and can be used to trigger error flags if the current values fall out of an acceptable range or, alternatively, to allow for normalization of the reported ECL signal to compensate for the actual electrode area.

The bubble detection methods described above can also be employed to detect the presence of fluids, the presence of bubbles in fluids and/or identify classes of samples in compartments in an assay cartridge outside the detection flow cells. For example, certain preferred embodiments of assay cartridges comprise fluid inlet and/or outlet lines for introducing and removing fluids from the cartridge flow cells, wherein these inlet and/or outlet lines comprise fluid detection electrodes for detecting the presence of fluid, the presence of air bubbles in fluids and/or for identifying samples. These fluid detection electrodes may have independent electrode leads and contacts. So as to reduce the number of electrical contacts to the cartridge, these fluid detection electrodes, preferably, comprise exposed surfaces of the leads to assay electrodes (e.g., assay electrodes in the assay cartridge flow cells). In this arrangement, it is further preferred that the exposed leads in a given fluid volume (e.g., an inlet line or outlet line) do not comprise leads from two electrodes that will be fired together in an assay measurement (e.g., used as a working electrode counter electrode pair in an ECL measurement). In this fashion it is ensured that the assay measurements are not affected by low resistance current paths between exposed leads.

With reference to the simplified embodiment depicted in FIG. 4, use of the impedance sensors 425 for detection of fluid presence and/or discrimination within the fluid input line 450 will now be discussed. Impedance sensors 425 are regions of electrically conductive surfaces on the electrode leads between electrodes 401-407 and electrode contacts 420. The electrically conductive surfaces are, preferably, exposed via apertures in a patterned dielectric layer that is patterned over the electrode leads. As fluid is directed into and through the fluid input line 450 (e.g., by use of pumps, valves, capillary flow, and the like), the impedance sensors 425 may be activated by a controller (not shown) that applies interrogation potentials between sensor pairs to detect and/or discriminate the fluid (the interrogation potentials being preferably lower than those required to induce ECL at the assay electrodes). The position of bubbles or fluids in the input line can be determined by sequentially measuring the impedance between different sensor pairs and comparing the values. The sensors are on alternating electrode leads so that when adjacent electrodes are fired during, e.g., an ECL measurement, the potential across the assay electrodes is not short circuited by current between sensors.

According to another aspect of the present invention, the electrode surfaces are coated with assay reagents such as antibodies or other specific binding reagents by dispensing solutions comprising the reagents to one or more appropriate locations on the electrode array, i.e., the capture surfaces. Preferably, the assay reagents collect on the surface (e.g., via the formation of covalent bonds, non-specific adsorption or specific binding interactions) to form an immobilized layer on the electrode. In a preferred embodiment, accurate volume delivery to a specified location results in complete coverage of only the desired electrode surface and/or a desired portion thereof. Accurate volume delivery to a specified location can be readily accomplished with commercially available dispensing equipment; e.g., commercially available equipment from BioDot.

Attaining complete coverage of a pre-defined region on a surface (e.g., an assay electrode) via localized deposition of a liquid (e.g., an assay reagent or a liquid comprising an assay reagent) can be difficult to achieve if the advancing contact angle of the liquid on the surface is high, thereby inhibiting spreading of the liquid on the surface (as has been observed for surfactant-free aqueous solutions on untreated carbon ink electrodes). Spreading can be accelerated by chemically modifying the surface to make it more wettable or by adding surfactants to the liquid, however, in many circumstances it is undesirable to change the physical properties of the surface or liquid. Alternatively, we have found that excellent and well controlled spreading of liquids can be achieved on surfaces, such as carbon ink electrodes, having high contact angle hysteresis (i.e., large differences in the advancing and retreating contact angle of the liquid on the surface, preferably differences greater than 10 degrees, more preferably greater than 30 degrees, more preferably greater than 50 degrees, most preferably greater than 70 degrees) by using impact-driven fluid spreading. Such results can be achieved without surface modification or the use of surfactants. Fluid is deposited (preferably, using a fluid micro-dispenser such as a micro-pipette, micro-syringe, solenoid valve controlled micro-dispenser, piezo-driven dispenser, ink-jet printer, bubble jet printer, etc.) on the surface at high velocity (preferably greater than 200 cm/s, more preferably greater than 500 cm/s, most preferably greater than 800 cm/s) so as to drive spreading of the liquid over the surface, despite the high advancing contact angle, to a size dictated by the volume and velocity of the dispensed fluid. The low retreating contact angle prevents significant retraction of the fluid once it has spread. Using the impact-driven spreading technique, it is possible to coat, with a predetermined volume of liquid, regions of a surface that are considerably larger (preferably, by at least a factor of 1.2, more preferably by at least a factor of two, even more preferably by at least a factor of 5) than the steady state spreading area of the predetermined volume of liquid on the surface (i.e., the area over which a drop having that volume spreads when touched to the surface at a velocity approaching zero).

Preferably, the region to be coated is defined by a physical boundary that acts as a barrier to confine the deposited fluid to the pre-defined region (e.g., a surrounding ledge or depression, a boundary formed of patterned materials deposited or printed on the surface, and/or a boundary formed via an interface with a surrounding region that varies in a physical property such as wettability). More preferably, the liquid has a higher receding contact angle on the surrounding region than on the pre-defined region (preferably, the difference is greater than 10 degree, more preferably greater than 30 degrees, most preferably greater than 50 degrees). Even more preferably, the surrounding region also exhibits a low contact angle hysteresis for the liquid (preferably, less than 20 degrees, most preferably, less than 10 degrees). By using a surrounding region having high receding contact angle and/or low hysteresis, the tolerance for imprecision in deposition velocity or spreading rate becomes much improved. In a preferred deposition method, a small volume of reagent is dispensed onto the pre-defined region with sufficient velocity to spread across the pre-defined region and slightly onto the surrounding region, the liquid then retracts off the surrounding region (due to its high receding contact angle) but does not retract smaller than the size of the pre-defined area (due to its low receding contact angle). In especially preferred embodiments of the invention the pre-defined area is an exposed area of an electrode (preferably, a carbon ink electrode) and the surrounding region is provided by a dielectric ink patterned on the electrode.

Figure 8:
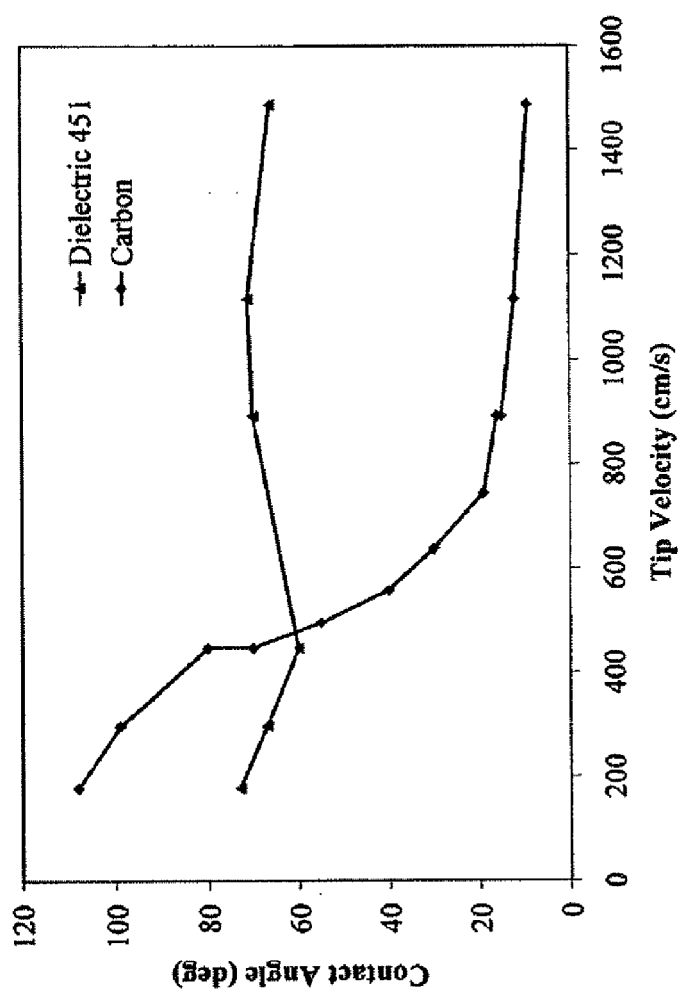
FIG. 8 plots the contact angle of drops of fluid on carbon ink and dielectric ink surfaces as a function of the dispensing velocity.

FIG. 8 illustrates typical observed contacts angles of 250 nL drops of water deposited using a solenoid valve-controlled micro-dispenser (Bio-Dot Microdispensor, Bio-Dot Inc.) on a preferred dielectric ink and a preferred carbon ink. The figure plots the contact angle as a function of the velocity of fluid as it leaves the tip of the dispenser. At low velocity, the observed contact angle is close to the advancing contact angle of water on the surface. As the velocity increases, impact-driven spreading causes the liquid to spread over a greater area and the observed contact angle decreases. At the high velocities, the observed contact angle becomes relatively independent of velocity as it approaches the receding contact angle of the liquid on the surface, the receding contact angle being the lowest contact angle the liquid can have on the surface (a lower contact angle would cause the drop to recede till it achieves the receding contact angle).

As described above, assay reagents such as antibodies or other specific binding reagents may be patterned by depositing (e.g., via impact driven spreading) solutions comprising the reagents on pre-defined locations on a surface (e.g., an electrode surface, preferably a carbon ink electrode surface) and allowing the reagents to become immobilized on the surface (e.g., via covalent bonds, non-specific interactions and/or specific binding interactions). Preferably, the region to be coated is defined by a physical boundary that acts as a barrier to confine the deposited fluid to the pre-defined region (e.g., a surrounding ledge or depression, a boundary formed of patterned materials deposited or printed on the surface, and/or a boundary formed via an interface with a surrounding region that varies in a physical property such as wettability) so as to form a fluid containment region.

In certain preferred embodiments, antibodies or other binding reagents (preferably proteinaceous binding reagents) are immobilized on carbon ink electrodes by non-specific adsorption. It may be advantageous to allow the assay reagent solution to dry on the electrode during the immobilization procedure. Preferably, the immobilization procedure further comprises blocking un-coated sites on the surface with a blocking agent such as a protein solution (e.g., solutions of BSA or casein), washing the surface with a wash solution (preferably a buffered solution comprising surfactants, blocking agents, and/or protein stabilizers such as sugars) and/or drying the surface.

In a preferred immobilization procedure of the invention, imprecision due to variations in the ability of different assay reagents to adsorb on a surface such as a carbon ink electrode are reduced by immobilizing via a specific binding interaction involving a first and second binding partner. Such an immobilization technique is less likely to be affected by small variations in the properties of the surface. By way of example, antibodies may be patterned by patterned deposition of antibody solutions (the first binding partner) on a surface coated with an antibody binding reagent (the second binding partner, e.g., an anti-species antibody, protein A, protein G, protein L, etc.). Alternatively, assay reagents labeled with the first binding partner (preferably, biotin) may be patterned by patterned deposition of the assay reagents on a surface coated with the second binding partner (preferably, anti-biotin, streptavidin, or, more preferably, avidin). Most preferably, the second binding partner is deposited in the same pattern as the assay reagents. By analogy, the method can be adapted to use any of a variety of known first binding partner—second binding partner pairs including, but not limited to, hapten-antibody, nucleic acid—complementary nucleic acid, receptor-ligand, metal-metal ligand, sugar-lectin, boronic acid—diol, etc.

Accordingly, one embodiment of an immobilization method of the invention comprises forming an assay domain comprising an assay reagent by: i) treating a predefined region of a surface (preferably, a carbon ink electrode surface) with a solution comprising a second binding partner so as to form an adsorbed capture layer (or, alternatively, a covalently bound layer) of said second binding partner (preferably, avidin) within the predefined region of said surface; (ii) treating the capture layer in the pre-defined region with a solution comprising the assay reagent, wherein the assay reagent is linked to or comprises a first binding partner (preferably, an assay reagent that is labeled with biotin) that binds the second binding partner. Preferably, a micro-dispensing technique is used to pattern the second binding partner and/or the assay reagent into the pre-defined region (more preferably both are patterned). More preferably, the pre-defined region is defined by a boundary (preferably defined by a dielectric layer patterned on the surface) adapted to confine small volumes of fluid to the pre-defined region.

The treating steps may comprise allowing the solutions to dry on the pre-determined regions. Between binding the second binding partner and binding the assay reagent, it may be advantageous to wash the surface with one or more wash solutions to remove excess unbound second binding partner. The wash solutions, preferably, comprise surfactant and/or blocking agents. After immobilizing the assay reagent, it may be advantageous to wash the surface with one or more wash solutions to remove unbound assay reagent. The wash solutions, preferably, comprise surfactants, blocking agents and/or protein stabilizers such as sugars. Useful blocking agents include standard blocking agents of the art (BSA, casein, etc.) but also include blocking reagents comprising the first binding partner (for example, free biotin) so as to block free binding sites on the immobilized layer of the second binding reagent. The wash steps may employ the wash techniques of the invention that employ concentric tubes for adding and removing wash solution. The surfaces are optionally dried after preparation for long term storage.

Preferably, the amounts of the second binding reagent and assay reagent applied to the pre-defined region are equal to or less than that required to saturate the surface. By choosing amounts roughly equal to the amounts required to saturate the surface, it may be possible to minimize both the amount of excess unbound reagent and the amount of unbound sites and thus avoid the need for washing or blocking steps. In an alternative embodiment, the amount of the assay reagent is kept below the amount of available binding sites in the capture layer to ensure that the binding capacity is determined by the amount of assay reagent added and not by amount of immobilized second binding partner (thus reducing the effect of variability in the efficiency of, e.g., the adsorption of the second binding partner).

The method may be applied to forming a plurality of assay domains comprising assay reagents immobilized in a plurality of pre-defined regions. In this case, the method is simply repeated for each of the pre-defined regions. Preferably, at least two of the assay domains comprise assay reagents that differ in selectivity for analytes of interest. When forming a plurality of assay domains, it is particularly advantageous to block the final product with a blocking reagent comprising the first binding partner (but not the analyte specific components of the assay reagent) to block excess binding sites on immobilized second binding partners; this procedure prevents assay cross-talk due to excess assay reagent on one pre-defined region diffusing and binding, via first binding partner-second binding partner interactions, to a different assay domain. For example, after using the two step procedure of binding avidin and then a biotin-labeled antibody, the surface may be blocked with free biotin. Alternatively, after using a two step procedure of binding Protein A (or other Fc binding receptor) and then an antibody against an analyte of interest, the surface may be blocked by using a different antibody or, more preferably, an Fc fragment of an antibody.

It has been observed that in some cases assay reagents adsorbed on a surface such as a carbon ink may, over time, slowly dissociate from the surface. This dissociation leads to the presence of free assay reagents that may interfere with assays that employ the adsorbed assay reagents. This dissociation may be greatly slowed by cross-linking the adsorbed assay reagents so that the immobilized species are greater in molecular weight and have more points of contact with the surface. Accordingly, in the immobilization methods described above, the second binding partner is, preferably, cross-linked to minimize dissociation of the reagent during surface preparation and/or storage. The cross-linking may be carried out via covalent cross-linking using standard chemical cross-linking agents. Alternatively, the cross-linking is carried out using specific binding interactions. In a preferred embodiment of the invention, the second binding partner is polyvalent (i.e., has multiple binding sites for the first binding partner) and is cross-linked by combining it with a cross-linking reagent that is either a polyvalent first binding partner or a molecule which comprises multiple first binding partners. In this embodiment, the amount of the cross-linking agent is selected so as to provide a beneficial amount of cross-links without saturating all the available binding sites on the second binding partners. The cross-links may be formed after the second binding partner is immobilized but are, preferably, formed in solution prior to immobilization. Advantageously, we have found that this cross-linking procedure not only acts to form a more stable surface but also increases the number of available binding sites on the surface (i.e., the binding capacity of the surface) by allowing the immobilization of more than a packed monolayer of the second binding partner (e.g., by extension of the polymerized second binding partner into solution).

By way of example, avidin (a tetrameric binding protein having four binding sites for biotin) is cross-linked to form poly-avidin by the addition of a small quantity of biotin-labeled cross-linking agent (for example, a protein such as BSA) having multiple biotin labels per protein molecule. Poly-avidin is then immobilized and used as a capture surface for immobilizing a biotin-labeled assay reagent, e.g., using the immobilization methods described above. The amount of biotin-protein is selected to allow cross-linking while leaving sufficient biotin binding sites available so that the immobilized poly-avidin can be used to capture a biotin-labeled first binding reagent (e.g., a biotin-labeled antibody). Preferably, the biotin-labeled cross-linking agent comprises at least two, more preferably, at least four, or more preferably, at least eight biotins per molecule. Preferably, the number of molar equivalents of cross-linking agent per mole of avidin is between 0.01 and 4, more preferably, between 0.01 and 1, even more preferably between 0.01 and 0.25, even more preferably between 0.05 and 0.25 and most preferably between 0.05 and 0.10. The concentration of avidin used for immobilization was preferably between 50-1000 ug/mL, more preferably between 100-800 ug/mL and most preferably around 400 ug/mL. By analogy, avidin may be replaced in these methods by other poly-valent biotin-specific receptors such as streptavidin.

Experiments were conducted to demonstrate the benefit of using poly-avidin capture layers on carbon ink electrodes and/or the two-step immobilization procedures of the invention. These experiments used screen printed carbon ink electrodes that were patterned on a plastic substrate. The working electrodes had an exposed circular area of about 3 mm$^2$ that was defined by a patterned dielectric layer that was screen printed over the carbon ink electrodes. The substrate also comprised at least one additional carbon ink electrode for use as a counter electrode. Reagents were immobilized by depositing (using a Bio-Dot dispenser) small volumes (200-300 nL) of a solution comprising the reagent onto the exposed electrode area (the solution being confined to the exposed electrode area by the dielectric layer) and allowing the solution to dry on the electrode. Poly-avidin was prepared by combining the appropriate amounts of avidin and biotin-BSA and incubating for 15 minutes. After the immobilization and/or washing steps (as described below), the substrate was either mated with a multi-well plate top so as to form the bottom surface of a well of multi-well plate or it was mated using a gasket made of double stick tape to a plastic sheet so as to form the bottom surface of a flow cell of an assay cartridge. The electrode surfaces were contacted with a buffered solution comprising tripropylamine (MSD Assay Buffer, MSD) by adding the buffer to a well of a multi-well plate or by introducing the buffer into the flow cell. ECL was induced by applying a voltage between the working and counter electrode (a ramp of 2-5 V over 3 seconds). ECL was measured by taking an image of the substrate using a cooled CCD camera.

Electrodes were coated with either avidin (by treating with 200 nL of a 75 ug/mL solution of avidin) or with poly-avidin (by treating with 200 nL of a solution containing 75 ug/mL avidin and 3.1 ug/mL biotin-labeled BSA and allowing the solutions to dry overnight; the BSA being labeled with a 4-fold excess of biotin-LC-sulfo NHS ester and having an expected ratio of biotins per BSA of roughly 2-3). The substrates were washed with water and the electrodes were then treated with 300 nL of a solution containing 100 ug/mL of an biotin-labeled anti-TSH antibody. The electrodes were washed with water, assembled into a cartridge into which was introduced a solution containing 20 uIU/mL of TSH and 12 ug/mL of an anti-TSH antibody that was labeled with a Sulfo-TAG NHS ester (MSD), an electrochemiluminescent label. The cartridge was incubated for 8 minutes to allow the binding reactions to occur, the substrate was then washed by passing MSD Assay Buffer into the flow cell and ECL was measured. The average emitted electrochemiluminescence intensity from the poly-avidin treated electrode (1652 units) was approximately three times that from the avidin treated electrode (602 units). Without being bound by theory, it is believed that the higher signal on the poly-avidin electrode represents an increased number of binding sites on the poly-avidin treated electrode and/or a reduction in the amount of avidin that washes off the poly-avidin electrode and adsorbs on other surfaces of the cartridge (thus competing with binding sites on the electrode).

In a similar experiment, the direct adsorption of anti-TSH antibody (by treatment of the electrode with a 100 ug/mL solution of an anti-TSH antibody) was compared to immobilization via a poly-avidin layer (as described above except that the poly-avidin solution contained 400 ug/mL avidin and 25 ug/mL biotin-BSA and the biotin-labeled anti-TSH was at a concentration of 100 ug/mL). The results showed that signal obtained using immobilization via poly-avidin (2207) was roughly twice that obtained using direct adsorption (1264). In addition, two step immobilization protocol was found to provide more precise results; the coefficients of variation (CVs) were three times lower when the two step method was employed.

The poly-avidin layers were further characterized by using avidin that was labeled with an electrochemiluminescent label (on average 0.3 Sulfo-TAG NHS labels per protein). The electrodes were treated with one of three solutions: (i) 75 ug/mL avidin, (ii) 75 ug/mL avidin and 25 ug/mL BSA or (iii) 75 ug/mL avidin and 25 ug/mL biotin-BSA. All the solutions contained 0.0035% Triton X-100. The electrodes were washed with water, immersed in MSD Assay Buffer and ECL was measured. The electrode treated with all the components of poly-avidin (avidin and biotin-BSA) gave an ECL signal (150981) that was roughly twice that observed for avidin alone (85235) or avidin with unlabeled BSA (65570), demonstrating that cross-linking was required for the improved performance of poly-avidin. It was also observed that the intensity of ECL was much more evenly distributed across the electrode for the poly-avidin electrodes than for the other electrodes.

In a different experiment the labeled and immobilized avidin or poly-avidin layers were i) not washed or ii) exposed to a solution containing BSA for 2 hours and then extensively washed with phosphate buffered saline. In this experiment, the avidin concentration was 0.5 mg/mL, the ratio of avidin to biotin-BSA was 16:1 and the labeled avidin was mixed with unlabeled avidin (at a 1:1100 ratio) to reduce the overall signals. The experiment was carried out on both non-treated electrodes and electrodes that were treated with an oxygen plasma. The table below shows that the use of poly-avidin substantially reduced the loss of avidin from the surface after extensive washes and exposure to protein-containing solutions.

After immobilizing assay reagents on surfaces for use in solid phase assays (e.g., by applying solutions comprising the assay reagents to the surfaces, most preferably, by patterned depositions of these solutions to form an array of assay domains comprising the assay reagents), assay performance is often improved by washing the assay electrodes to remove unbound assay reagents. This washing step is particularly important when unbound assay reagent may interfere with an assay (e.g., unbound antibodies may interfere by competing with the capture of analytes to antibodies on the surface). Preferably, this washing step is carried out using a procedure that minimizes the ability of unbound reagents to adsorb in other undesirable locations. For example, after immobilization of an antibody on an assay domain on an electrode in an assay module, the washing step will preferably minimize the adsorption of unbound antibody to non-electrode surface (antibody adsorbed on non-electrode surfaces interfering with binding assays by competing for the binding of analyte with antibody immobilized on the electrode). Even more importantly, in array type measurements involving a plurality of assay domains specific for different analytes of interest, the washing step should minimize the diffusion of an unbound assay reagent from one assay domain and its adsorption on a different assay domain (this process leading to assay cross-talk).

Figure 7A:
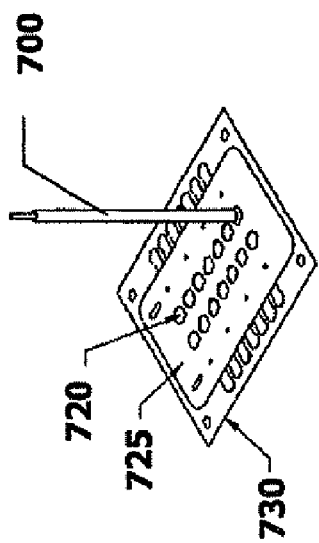
FIG. 7a illustrates the use of a localized washing apparatus having concentric tubes.
Figure 7B:
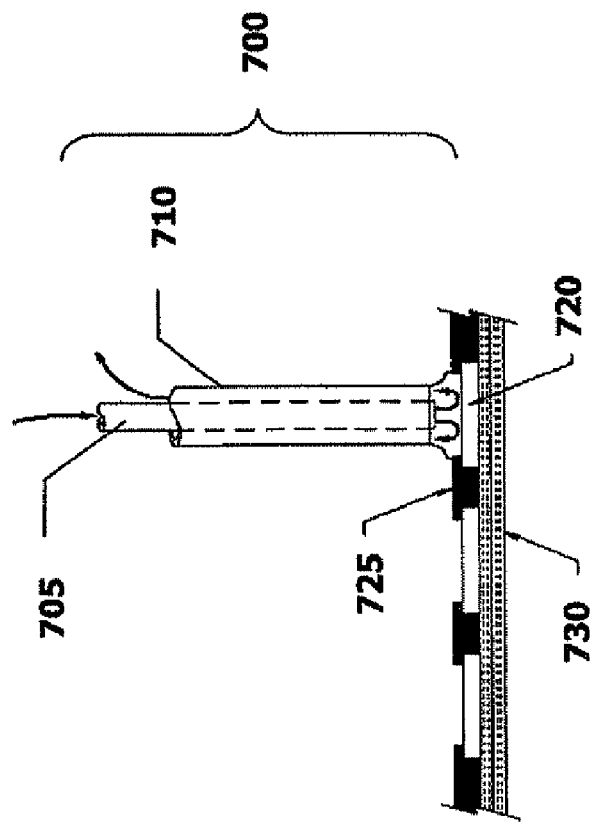

We have found that we can prevent the undesired adsorption of assay reagents outside pre-defined locations by localized washing of assay domains using a concentric tube dispense/aspirate fixture. FIGS. 7a and 7b depict one embodiment wherein a washing fixture was constructed that consists of a single concentric tube structure which may be used to wash a single assay domain in an assay module or to sequentially wash multiple assays domains in an assay module by positioned the concentric tube structure over each assay electrode. It should be understood, however that the invention is not limited to a single concentric tube device but can, preferably, employ an array of concentric tubes, preferably, arranged in the same pattern and spacing as the assay domains. Preferably, wash fluid is dispensed through inner tube 705 and aspirated through outer tube 710. In operation, as the fluid transitions from the inner tube to the outer, it preferably passes over the assay domain surface, washing the assay domain in an area confined by the diameter of the outer tube. The figure shows the concentric tube being used to wash a carbon ink electrode 720 patterned on substrate 730, the exposed surface of electrode 720 being defined by patterned dielectric layer 725 which acts as a boundary to form a fluid containment region on electrode 720. By analogy, the concentric tubes may be used to wash assay domains on a variety of other surfaces, the assay domains being preferably but not necessarily defined by a fluid boundary. The tubes are preferably configured so that the outer tube removes fluid with a high enough efficiency so as to prevent the spread of fluid to regions outside the domain being washed. In alternate embodiments, the functions of the inner and outer tubes may

|  | Unmodified Electrodes | | | | Plasma-Treated Electrodes | | | |
| --- | --- | --- | --- | --- | --- | --- | --- | --- |
|  | Avidin | | Poly-Avidin | | Avidin | | Poly-Avidin | |
|  | Signal | % Left | Signal | % Left | Signal | % Left | Signal | % Left |
| No Wash | 21,107 |  | 26,618 |  | 10,871 |  | 18,512 |  |
| Wash | 9,545 | 45 | 18,845 | 71 | 3,332 | 31 | 14,024 | 76 | also be reversed such that the wash fluid is dispensed through the outer tube, and aspirated up the center via the inner tube. These arrangements of tubes prevent unbound assay reagents on the assay domains from contacting other surfaces of the assay module.

In another alternate embodiment, a tube structure having three concentric tubes is used to pattern and wash assay reagents on assay domains. A first tube (preferably the inner tube) is used to microdispense assay reagents on an assay domain. This tube is preferably linked to a low volume fluid dispensing controller such as a microsyringe (optionally, having a solenoid valve flow controller) or piezoelectric dispenser. The second tube (preferably the middle tube) is used to dispense bulk washing reagents on the assay domain. The third tube (preferably the outer tube) is used to aspirate excess assay reagent and/or to wash reagents from the assay domain. Using this arrangement, a single device may be used to dispense assay reagents onto an assay domain (e.g., so as to cause localized immobilization of the assay reagent on the assay domain) and to wash excess assay reagent from the assay domain, these operations occurring without contamination of adjacent surfaces with the assay reagent. Optionally, an array of these devices is used to pattern and wash an array of assay domains.

The invention relates in part to assay cartridges. An assay cartridge of the invention incorporates one or more fluidic components such as compartments, wells, chambers, fluidic conduits, fluid ports/vents, valves, and the like and/or one or more detection components such as electrodes, electrode contacts, sensors (e.g., electrochemical sensors, fluid sensors, mass sensors, optical sensors, capacitive sensors, impedance sensors, optical waveguides, etc.), detection windows (e.g., windows configured to allow optical measurements on samples in the cartridge such as measurements of absorbance, light scattering, light refraction, light reflection, fluorescence, phosphorescence, chemiluminescence, electrochemiluminescence, etc), and the like. A cartridge may also comprise reagents for carrying out an assay such as binding reagents, detectable labels, sample processing reagents, wash solutions, buffers, etc. The reagents may be present in liquid form, solid form and/or immobilized on the surface of solid phase supports present in the cartridge. Certain preferred embodiments of the invention, comprise detection chambers having the electrode arrays and/or binding domains as described above (e.g., the electrode arrays described in FIGS. 1-4).

The fluidic components are preferably designed and incorporated into the cartridge body to form the fluidic network using certain predefined design guidelines. The design guidelines for each component can be dependent upon one or more factors such as, e.g., cartridge body design (i.e., single-piece body, multiple piece body, modular body, single read chamber, multiple read chamber, and the like), manufacturing process (e.g., injection molding, blow molding, hot stamping, casting, machining, etc.), materials (e.g., acrylic, PVDF, PET, polystyrene, polypropylene and the like), assay requirements (e.g., binding assay, competitive binding assay, single step assay, two-step assay, etc.), functional requirements (e.g., sample size, assay reagent volumes, detection technology, time-to-result, incubation, heating, mixing/agitating), safety/handling requirements (e.g., self-containment, regulatory approval, ease of use, etc.), and/or the like.

The skilled practitioner will be able to readily select materials suitable for the fabrication of the cartridges of the invention. Suitable materials include glass, ceramics, metals and/or plastics such as acrylic polymers (such as Lucite), acetal resins (such as Delrin), polyvinylidene fluoride (PVDF), polyethylene terephthalate (PET), polytetrafluoroethylene (e.g., Teflon), polystyrene, polypropylene, ABS, PEEK and the like. Preferably, the materials are inert to any solutions/reagents that will contact them during use or storage of the cartridge. In certain preferred embodiments, at least some portion of the cartridge is fabricated from transparent and/or translucent materials such as glass or acrylic polymer to provide windows that allow optical interrogation of fluids or surfaces inside the cartridge, e.g., for analysis of compositions within detection chambers of the cartridge or for monitoring and controlling the movement of liquids through the fluidic networks defined within the cartridge.

One preferred embodiment of the invention is a cartridge that includes one or more sample chambers, one or more detection chambers (preferably, detection chambers adapted for use in ECL measurements as described above) and one or more waste chambers. The chambers are connected in series by fluid conduits so that a sample introduced into a sample chamber can be delivered into one or more detection chambers for analysis and then passed into one or more waste chambers for disposal. Preferably, this cartridge also includes one or more reagent chambers for storing liquid reagents, the reagent chambers connected via conduits to the other components so as to allow the introduction of the liquid reagents into specified sample or detection chambers. The cartridge may also include vent ports in fluidic communication with the sample, detection and/or waste chambers (directly or through vent conduits) so as to allow the equilibration of fluid in the chambers with the atmosphere or to allow for the directed movement of fluid into or out of a specified chamber by the application of positive or negative pressure.

In an alternative embodiment, a sample chamber and a waste chamber are both arranged upstream from a detection chamber having first and second inlet/outlet conduits (preferably, a detection chamber having an elongated shape, the inlet/outlet conduits being arranged at or near the opposite ends of the elongated dimension). The cartridge is configured to allow the introduction of sample into the detection chamber via the first inlet/outlet conduit and then the reversal of flow to direct the sample fluid back out the first inlet/outlet conduit and to the waste chamber. Preferably, a reagent chamber is located downstream of the detection chamber and the cartridge is configured to allow introduction of the reagent to the detection chamber via the second inlet/outlet conduit (i.e., in "reverse flow" relative to the introduction of sample). This arrangement is particularly well suited to measurements that suffer from strong sample interference, the reverse flow being especially efficient at washing residual sample from the detection chamber. This embodiment is especially useful in ECL-based assays for markers (e.g., cell wall markers of gram positive bacteria) in samples containing a nitrous acid-containing extraction buffer (see, e.g., the extraction methods and reagents disclosed in U.S. Provisional Patent Application 60/436,591, filed Dec. 26, 2002, entitled Methods Compositions and Kits for Biomarker Extraction, hereby incorporated by reference). One preferred embodiment of the invention uses a cartridge configured with a reverse flow wash to conduct an ECL binding assay for a panel of upper respiratory pathogens including streptococcal species and optionally other pathogens such as influenza A and B and RSV (preferably by employing an array of antibodies against markers of the pathogens, the array preferably being formed on one or more electrodes, most preferably an electrode array as described above and in FIGS. 1-4).

The reverse flow wash significantly reduces the detrimental effects of nitrous acid on ECL measurements. In preferred embodiments, the washing efficiency is such that the fraction of sample (or reagent) left in a detection chamber after a wash is less than 1/1000; more preferably less than 1/10,000, even more preferably less than 1/100,000

The sample chamber is a chamber defined within a cartridge that is adapted for receiving a sample to be analyzed in the cartridge. The sample chamber includes a sample introduction port for introducing sample into the chamber. The port is preferably an opening in the cartridge that provides access to the sample chamber. Alternatively, the port may be a membrane or septa through which a sample may be injected into the sample chamber, e.g., through the use of a needle or cannula. Preferably, the cartridge also includes a sealable closure for sealing the sample introduction port and preventing leakage of the sample and possible exposure of the user and/or associated instruments to biohazards. Preferably the sealing/capping mechanism utilizes a hinged configuration so that the sample chamber is easily accessed and sealed. In particularly preferred embodiments the sealing/capping mechanism incorporates a flexible hinge, e.g., rubber, plastic or the like. Most preferably, the sample chamber is adapted and configured to receive a modular detachable insert that includes a cap for sealing the sample chamber. Use of a modular detachable insert within the sample chamber also allows for independent selection of materials for the main cartridge body. In an alternative embodiment, sealing of the sample introduction port is achieved by applying an adhesive tape to the port. The sample chamber may contain dry reagents used in carrying out the assay that reconstitute on addition of a liquid sample. Optionally, the sample chamber contains an anti-foam agent to prevent foaming of the sample in the cartridge.

Figure 9:
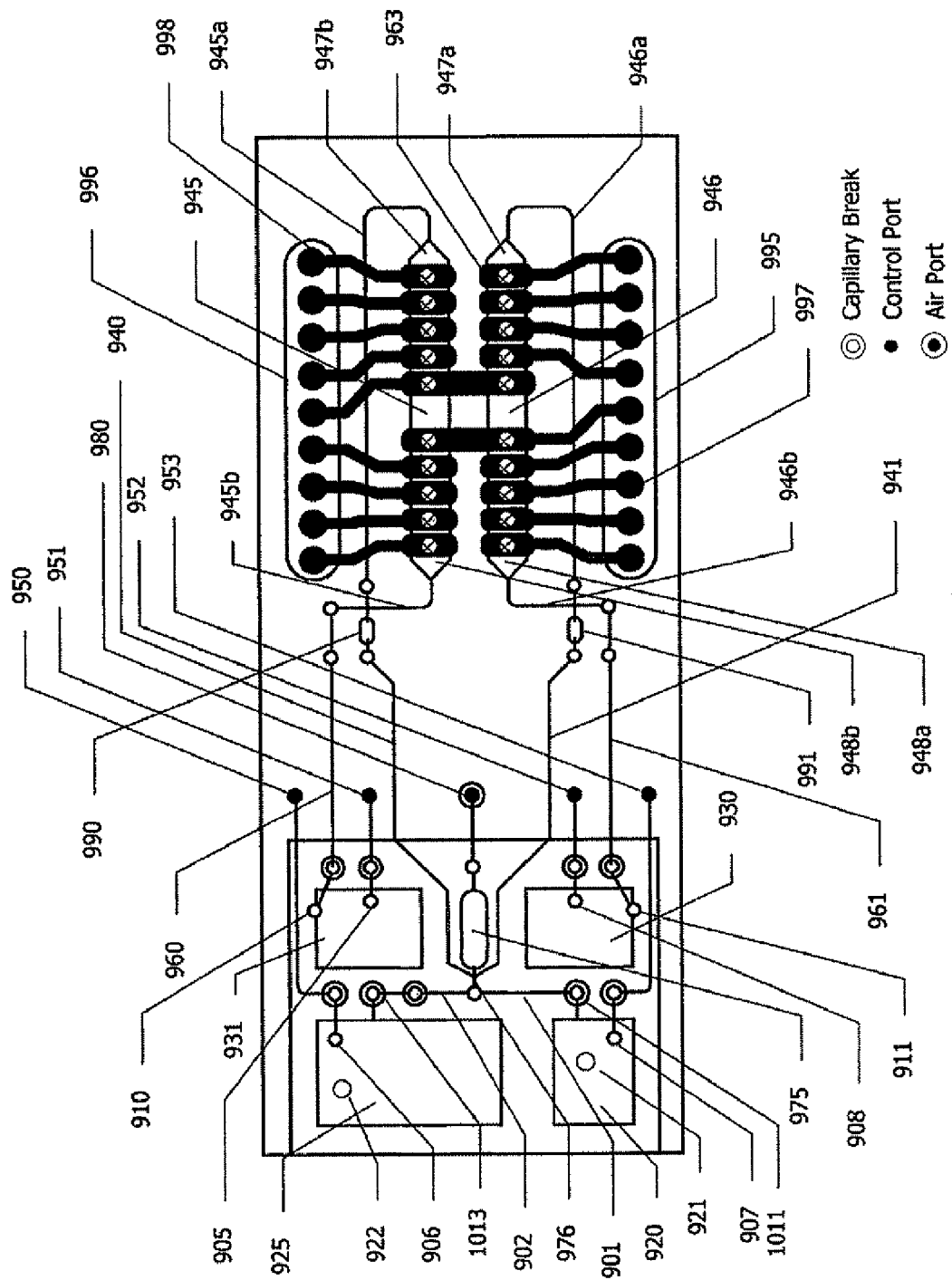
FIG. 9 is a schematic representation of one embodiment of an assay cartridge illustrating various fluidic components.
Figure 20:
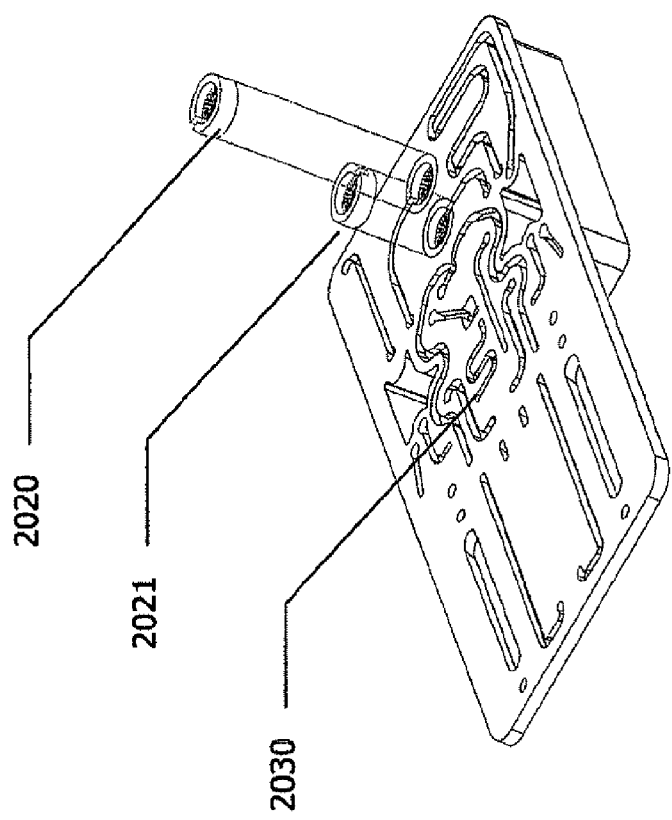
FIG. 20 is a bottom isometric view of an alternative assay cartridge embodiment illustrating filter inserts.
Figure 27:
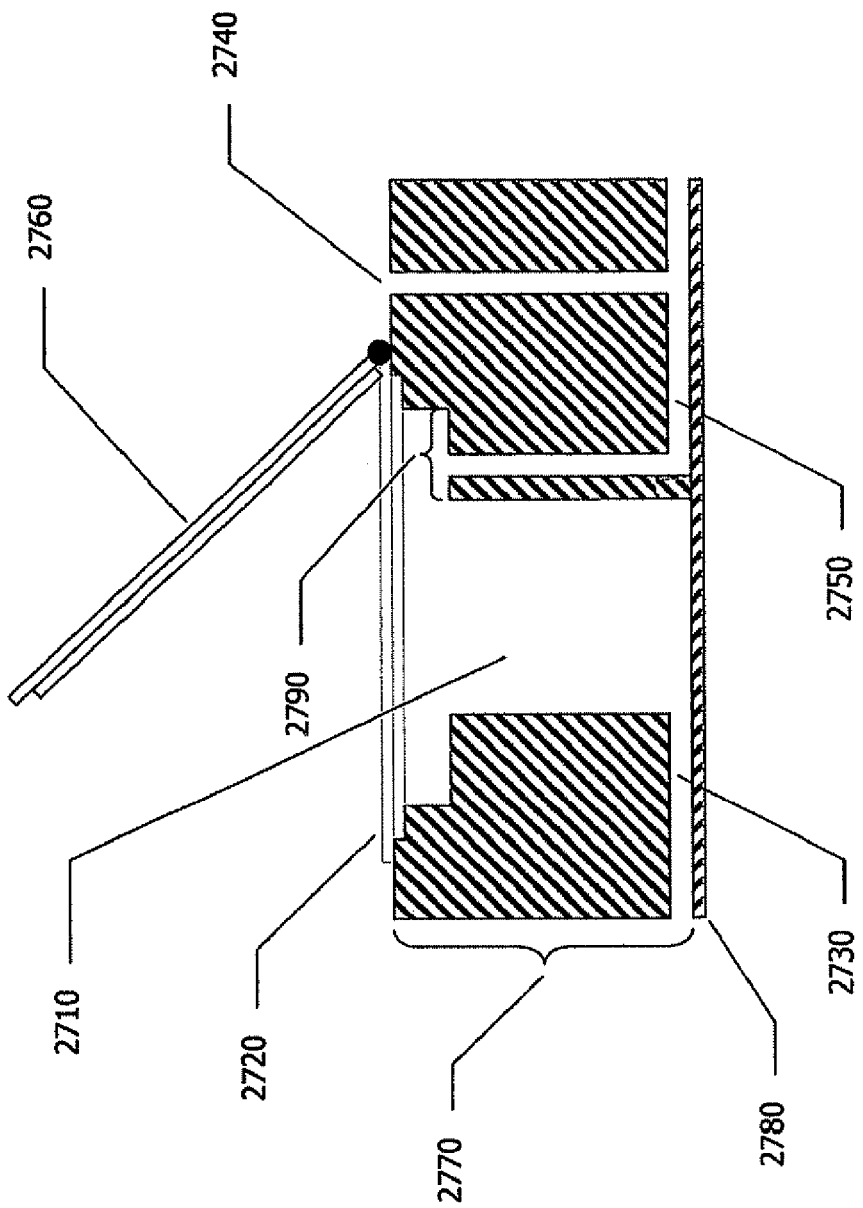
FIG. 27 is a cross-sectional view of a sample chamber having an integral vent port within the chamber itself.

The sample chamber is connected to a sample conduit for transferring fluids from the sample chamber to other fluidic components in the cartridge. The sample chamber may also be connected to a vent port and/or a reagent chamber (e.g., through fluidic conduits). In a preferred configuration for receiving liquid samples, the sample chamber is connected to a sample conduit and a vent port. A cross-sectional view of a preferred embodiment is shown in FIG. 27. Sample chamber 2710 has sample introduction port 2720 and is linked to sample conduit 2730 and sample vent port 2740 (through vent conduit 2750). Sample conduit 2730 is advantageously arranged to intersect sample chamber 2710 at or near the bottom of the chamber (relative to the orientation of the cartridge during operation) so as to allow for efficient transfer of a large fraction of the sample volume without the introduction of bubbles. Vent conduit 2750 is advantageously arranged to intersect sample chamber 2710 above sample conduit 2730 and at a height that is greater than the anticipated sample fill level height to avoid possible contamination of the instrument and/or escape of the sample fluid. Preferably, vent conduit 2750 has sufficient volume in the fluidic conduit so that a small amount of sample fluid, e.g. as may be observed if the sample is foamy or has bubbles, may enter the conduit without being pulled all the way to vent port 2740. In one embodiment, as depicted in FIG. 9, a well/trap 975 may be arranged within the fluidic conduit. In another embodiment, as depicted in FIG. 20, the fluidic conduit may be extended/lengthened, e.g., utilizing a serpentine configuration 2030.

Cap 2760 can be used to seal sample introduction port 2720 without preventing the flow of air through vent conduit 2750. In FIG. 27, the fluidic compartments and conduits are formed by recesses (e.g., channels) or holes in cartridge body 2770 and by cover layer 2780 which is sealed against cartridge body 2770. Sample chamber 2710 has internal ledge 2790. Vent conduit 2750 includes a vertical hole from the bottom of cartridge body 2770 to the top face of ledge 2790. This arrangement provides for a simplified manufacturing process that is amenable to injection molding or machining of the cartridge body; other arrangements of the vent conduit will be readily apparent to the skilled artisan.

In one embodiment of the sample chamber, a separate vent port and vent conduit are omitted and the sample introduction port also provides a vent port, e.g., the sample introduction port aperture also acts as a vent port. The vent port may also be provided through the top of the sealing/capping mechanism by, e.g., incorporating a vent hole in the top surface of the sealing/capping mechanism. An alternative embodiment may employ a scheme whereby the cartridge reader itself can include a piercing/venting mechanism that is adapted and configured to pierce through the top surface of the flexible sealing/capping mechanism. In a particularly preferred embodiment, the sealing/capping mechanism is adapted and configured to be self-sealing upon withdrawal/removal of the piercing/venting mechanism, e.g., via the use of a septum preferably comprising an elastomeric material. The advantage of a self-sealing cap mechanism is that the sample cannot escape from the sample chamber once the piercing/venting mechanism has been removed.

The sample chamber may also include a filter for, e.g., removing particulate matter that may be present within the sample itself or that may be present as a result of using a swab or the like to introduce sample into the sample chamber. A preferable embodiment may employ a filter that not only removes any particulate matter but that is also designed to separate red blood cells (RBC) from blood plasma; e.g., where the particular assay/assay format requires blood plasma as the sample. Such a filter can be an integral cross-flow filter, in-line filter or the like. Preferably, the filter is arranged at or near the entrance of the sample conduit.

In a preferred embodiment for extracting analytes from a solid matrix or a matrix that comprises solids (e.g., for extracting analytes from an absorbent material (e.g., a cotton ball, piece of filter paper, etc.), an applicator stick, dirt, food, sludge, feces, tissue, etc.) the sample chamber is connected to a reagent chamber (e.g., via a reagent conduit) comprising an extraction reagent, e.g., an extraction reagent disclosed in U.S. Provisional Patent Application 60/436,591, filed Dec. 26, 2002, entitled Methods Compositions and Kits for Biomarker Extraction, hereby incorporated by reference. Applicator stick is used herein to refer to a sample collection device comprising an elongated handle (preferably a rod or rectangular prism) and a sample collection head (preferably comprising an absorbant material or, alternatively, a scraping blade) configured to collect sample from a surface or biological tissue) and includes sample collection swabs and tissue scrapers. The reagent conduit and sample conduit are, preferably, arranged to intersect the sample chamber at or near opposing ends of the chamber so that reagent introduced through the reagent conduit is drawn through the sample before passing into the sample conduit. More preferably, the sample chamber has an elongated shape with the two conduits being arranged to intersect at or near the opposing ends of the length. The sample chamber may also include a filter, as described above, for removing solid material. Extraction of analytes from solid materials and, in particular, porous meshes such as may be found in swab heads may lead to the introduction of bubbles and air gaps into the resulting fluid stream. Preferably, the sample chamber or the downstream fluidic components (e.g., the sample conduit) include a bubble trap to remove air introduced during an extraction step.

Figure 28:
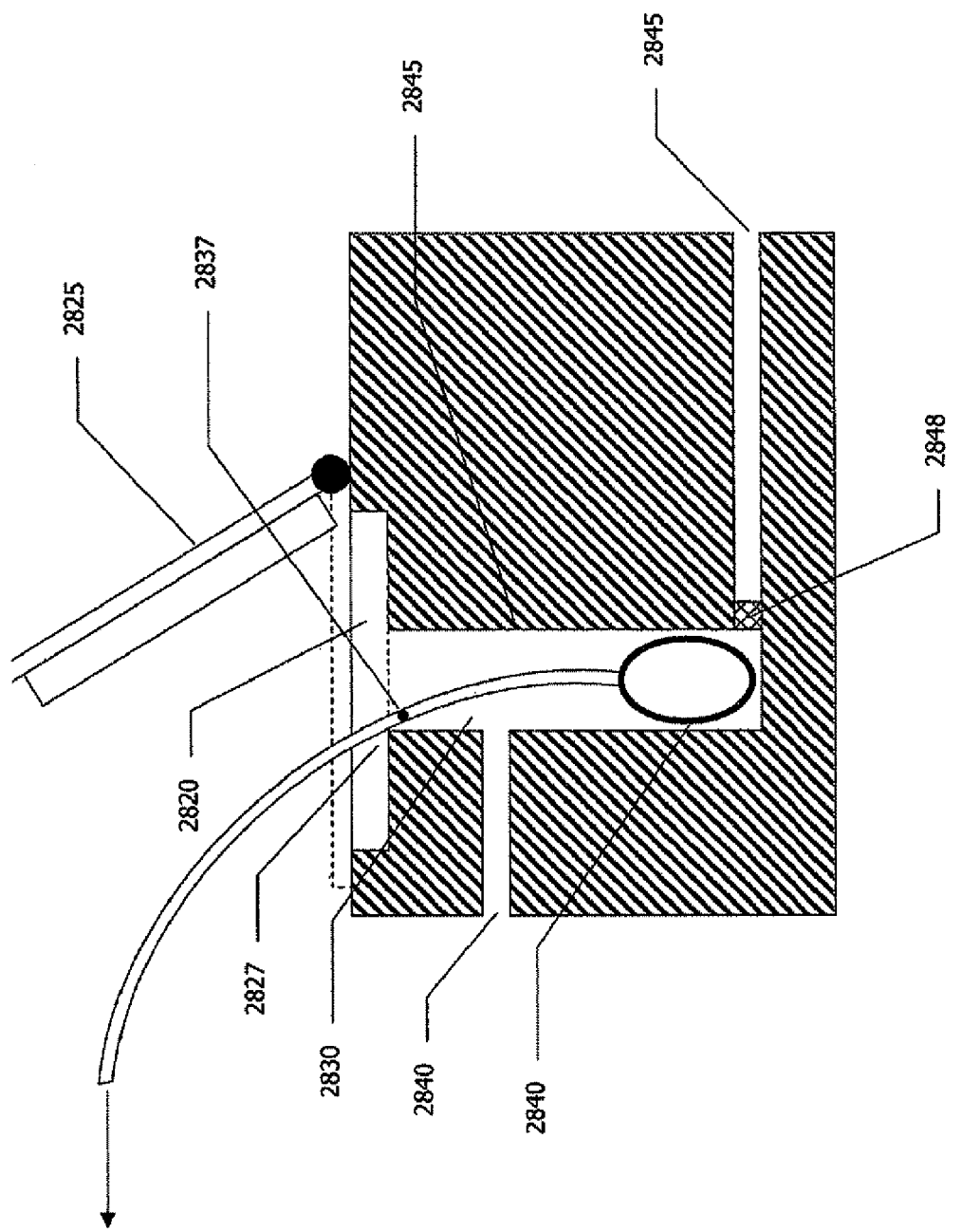
FIG. 28 is a cross-sectional view of one embodiment of a sample chamber for extracting analyte from a solid or solid-containing matrix.

FIG. 28 shows a cross-sectional view of one exemplary embodiment of a sample chamber for extracting analyte from a solid or solid-containing matrix. Elongated sample chamber 2810 has a sample introduction port 2820 equipped with a sealable closure as described above. The sample chamber is shown holding an applicator stick, specifically swab 2830 having absorbent swab head 2835. Reagent conduit 2840 and sample conduit 2845 are arranged to intersect sample chamber 2810 on opposing sides of swab head 2835 so that extraction reagent introduced through reagent conduit 2840 passes through swab head 2835 before entering sample conduit 2845. Optionally, a filter element 2848, may be included to remove particulates from the extracted sample. Preferably, the width of sample chamber 2810 in the region that surrounds the head of an inserted applicator stick is less than two times (more preferably less than 1.5 times, even more preferably less than 1.2 times, most preferably equal to or less than 1.0 times) the width of the widest region of the applicator stick that needs to pass through that region during insertion of the applicator stick. Alternatively, the cross-sectional area of sample chamber 2810 in the region that surrounds the head of an inserted applicator stick is less than four times (more preferably, less than two time, most preferably less than or equal to 1.0 times the cross-sectional area of the widest region of the applicator stick that needs to pass through that region. When used to extract sample from porous compressible materials (e.g., a swab having a porous compressible head), the width of the sample chamber is selected so that the width is narrow enough around the applicator stick head so that the material fills most or all the width of the chamber (ensuring the most efficient flow of extraction buffer through the material) but wide enough so that material can be easily inserted without the need for excessive force and without causing leakage of fluid in the material onto the outside surfaces of the cartridge (optionally, both properties may be achieved by use of a chamber that, with respect to a seated applicator stick is narrower in the region that surrounds the head than in the region that surrounds the shaft). In certain preferred embodiments, these properties are achieved while. Advantageously, sealing sample port 2820 prevents the release of air from that end of sample chamber 2810 and prevents the wasteful flow of extraction reagent away from sample conduit 2845. Optionally, swab 2830 and/or chamber 2810 are designed so that swab 2830 fits completely into chamber 2810. Alternatively (as shown), an applicator stick is too long to fit in chamber 2810 (e.g., the length of swab necessary to collect a mucous sample from the throat or nasal cavity may be too long to fit within the desired form factor of a cartridge) but is cleaved (e.g., broken, fractured, cut or otherwise detached) prior to or, preferably, after its introduction into chamber 2810 so as to produce a shortened stick fragment comprising the sample collection head. The shortened fragment is short enough to fit in chamber 2810 and allow closure 2825 to be sealed. In certain embodiments, the swab is designed to allow for easy detachment by having, e.g., a reversibly detachable head or by including a weak point in the shaft that allows for facile fracture of the shaft.

One method of introducing an applicator stick such as swab 2830 to sample chamber 2810 comprises i) introducing it into chamber 2810; ii) cleaving the swab shaft to form a head segment (comprising the head) and a shaft segment and iii) sealing the head segment in chamber 2810 by sealing closure 2825. The method may further comprise iv) introducing an extraction reagent through reagent conduit 2840; v) extracting analyte from swab head 2830 by passing extraction reagent through swab head 2835 and vi) removing the extracted analyte through sample conduit 2845. The extracted analyte may then be directed to a detection chamber for analysis. In one preferred embodiment, the shaft is cleaved by applying a force to the exposed end of the shaft of swab 2830 in a direction perpendicular to the length of chamber 2810 so as to break the shaft at an edge 2827 of chamber 2810 and allow removal of the part of the shaft that extends out of the chamber. Preferably, swab head 2830 is seated against the opposing end of chamber 2810 prior to cleaving the shaft.

In an especially preferred embodiment, the shaft of swab 2830 is constructed to have weak point (shown as weak point 2837) so that application of a force causes swab 2830 to reproducibly break at the weak point. Preferably, the swab shaft includes a stress/strain concentration feature (notch, score, or the like), e.g., the weak point is introduced by making the swab shaft narrower at the weak point or by "scoring" the shaft (i.e., cutting or etching one or more notches into the shaft at the weak point). Preferably the notch forms a circuit around the shaft so that the shaft may be broken in any direction. Such a notch may be made by cutting a groove in the shaft (e.g., with a tool or a laser) while turning the applicator stick on a lathe. Most preferably, the weak point is located so that when the shaft is inserted into chamber 2810 it is sufficiently near to edge 2827 so that a sufficient force can be applied to break the shaft, but sufficiently close to head 2835 so that the closure 2825 can be sealed.

The sample chamber may also include additional passive and/or active features to promote a facile and reproducible break of a swab within the sample chamber. Passive features may include one or more of, e.g., geometrical configuration/arrangement of the sample chamber itself (e.g., curvature or angles along the length of the sample chamber), force focusing elements (e.g., protrusions from the internal walls of the sample chamber), and the like. Active features may include one or more actuatable mechanisms arranged and configured within the sample chamber for cleaving the swab, e.g., a "guillotine" device similar to a cigar cutter that can be actuated by a user exerting a force upon the device.

Figure 29:
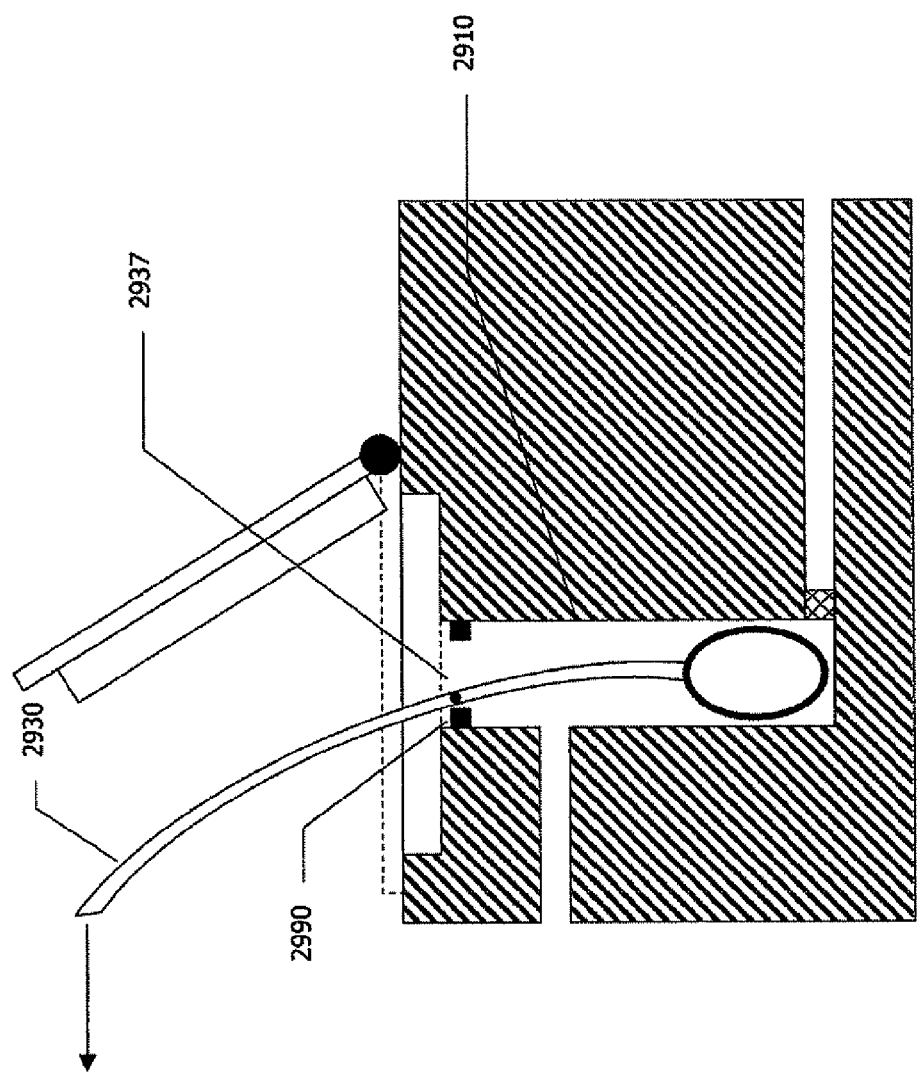
FIG. 29 is a cross-section view of an alternative embodiment of a sample chamber for extracting analyte from a solid or solid-containing matrix incorporating force focusing elements.

FIG. 29 shows sample chamber 2910, an adaptation of sample chamber 2810. Sample chamber 2910 has a constriction defined by protrusions 2990 that project inward from the walls of the chamber to form force focusing elements within the chamber. As illustrated in the figure, applying a lateral force to swab 2930 that is seated in sample chamber 2910 causes the swab shaft to contact one or more protrusions 2990. The lateral force is thereby focused on one location on the swab, promoting breakage of the swab at that location. Preferably, the swab and sample chamber are designed/selected so that the swab has a weak point (shown as weak point 2937) at the same location (preferably, the swab is scored at that location).

Figure 30:
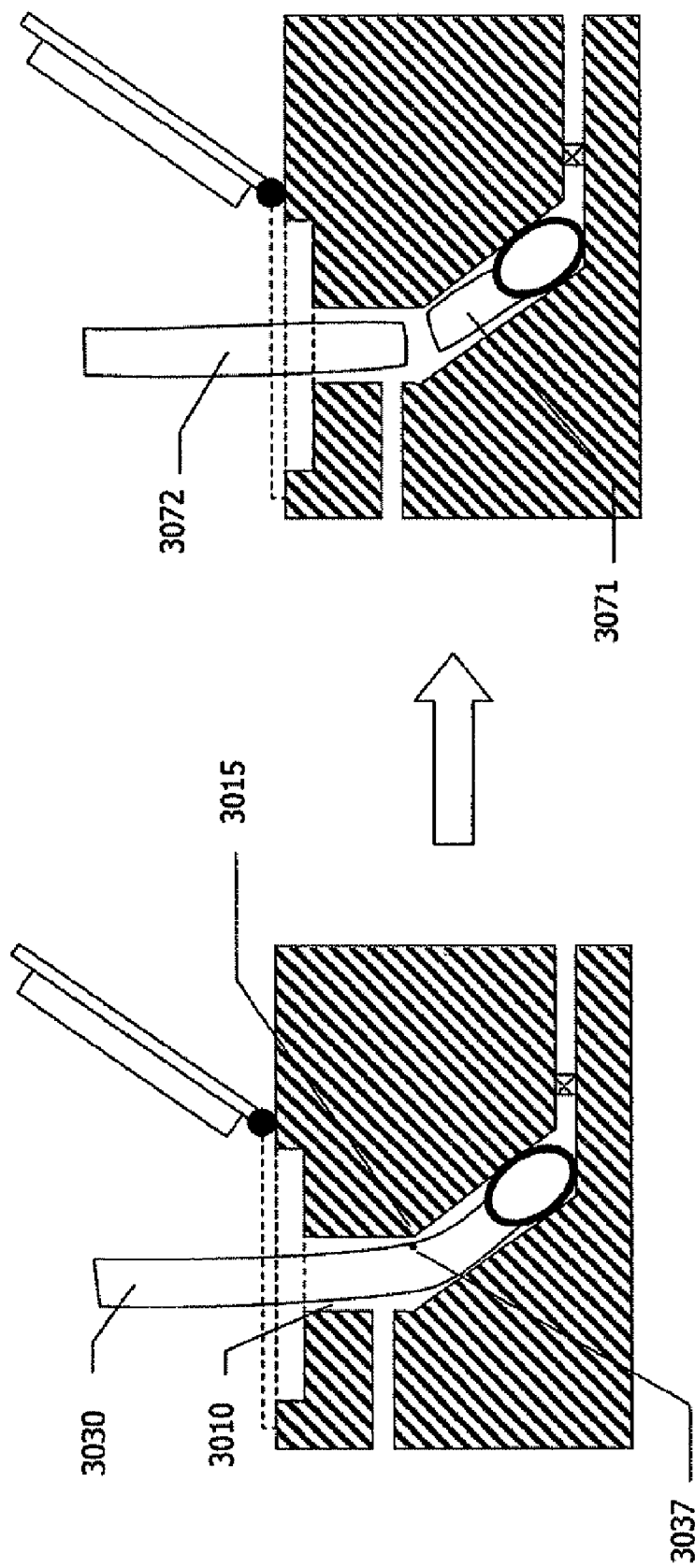
FIG. 30 is a cross-section view of another embodiment of a sample chamber for extracting analyte from a solid or solid-containing matrix incorporating a two-region, or compound, sample chamber.

In an especially preferred embodiment, the sample chamber is configured to cause an applicator stick to bend upon insertion thus promoting fracture of the shaft. FIG. 30 shows sample chamber 3010, an especially preferred adaptation of sample chamber 2810 that has a bend or angle 3015 along its length such that the sample chamber has a first elongated region (on one side of the bend or angle) oriented in one direction and a second elongated region (on the other side of the bend or angle) oriented in second direction, the two regions being oriented at an angle relative to each other. As shown in the FIG. 30, insertion of swab 3030 leads to contact between a location on the shaft of the swab and a site on the inner surface of the angle or bend. This contact focuses force on that location and promotes breakage of the shaft at that location (to form head segment 3071 and shaft segment 3072). Preferably, the width of the sample chamber is designed to fit the swab head snugly but not so tightly that insertion of the swab requires excessive force. Most preferably, the swab and sample chamber are designed/selected so that the swab has a weak point (shown as weak point 3037) at or near the location of contact (preferably, the swab is scored at that location). Applicants have found that this arrangement allows for concurrent insertion and breaking of the swab in one simple operation. Advantageously, the breakage is extremely reproducible and occurs without any violent motion that can lead to expulsion of sample from the cartridge. Preferred angles or degrees of curvature are 20-90 degrees, more preferably 30-70 degrees, even more preferably 40-50 degrees, most preferably 45 degrees. While FIGS. 28, 29 and 30 illustrate embodiments employing swabs, the techniques are applicable to other types of application sticks.

The reagent chambers are chambers adapted to hold liquid reagents used during the course of assays carried out in a cartridge. The reagent chamber design considerations for preferred embodiments of a cartridge depend, in part, upon the particular assay(s) to be performed by the cartridge. For example, a cartridge may have one, two or more reagent chambers depending on the number of reagents required by the assay format. Liquid reagents that may be held in a reagent chamber include buffers, assay diluents, solutions containing binding reagents (e.g., proteins, receptors, ligands, haptens, antibodies, antigens, nucleic acids and the like), solutions containing enzymes and/or enzyme substrates, solutions containing control reagents, ECL read buffers containing ECL coreactants (e.g., tertiary amines such as piperazine-N,N'-bis (2-ethanesulfonic acid) and tripropylamine), wash solutions, anti-foam agents, extraction reagents (e.g., solutions containing detergents, acids, bases, nitrous acid, nitrate salts, etc.) and the like. A cartridge may have one, two or more reagent chambers depending, e.g., on the number of reagents required by the assay format. The reagent chamber design considerations for preferred embodiments of a cartridge depend, in part, upon the particular assay(s) to be performed by the cartridge. The reagent chamber is connected to a reagent conduit for transferring reagent from the chamber to other fluidic components in the cartridge. The reagent chamber is, preferably, also connected to a reagent vent port (optionally, through a reagent vent conduit). The arrangement of the conduit connections to the chamber falls under similar design considerations as those described for the sample chamber, sample conduit and sample port; preferably, the reagent conduit intersects the chamber at or near the bottom and the reagent vent/vent conduit intersects the chamber at or near the top (relative to the orientation of the cartridge during use). Optionally, a filter element is placed before or in the reagent conduit, e.g., if the reagent solution is expected to contain particles that may clog the cartridge fluidics or otherwise negatively affect assay performance.

In one embodiment of the invention, a cartridge has one or more reagent compartments that are empty or contain only dried reagents. Prior to conducting an assay, the user or cartridge reader dispenses liquid reagents into the these chambers (e.g., through reagent vent ports or through reagent introduction ports similar to the sample introduction port described above) which, optionally, reconstitute any dried reagent present in the chambers; the reagents are thus prepared for use in the assay. Sealable closures may be used to prevent leakage of the reagents after their addition.

Preferably, where an assay requires the use of liquid reagents, some or all of these liquid reagents are stored in liquid form in reagent chambers so as to minimize the number and complexity of the operations that must be carried out by a user or cartridge reader. In one preferred embodiment the reagent chamber(s) can be filled with the requisite assay reagent(s) at the time of cartridge manufacture and subsequently sealed. When used to store liquid reagents, the reagent chambers should be designed so as to prevent leakage and or evaporative loss of the reagents from the chambers during storage. In a particularly preferred embodiment the assay reagents are incorporated into assay reagent modules that can be assembled into the cartridge's assay reagent chambers during manufacture. By designing the assay modules to have desired properties such as resistance to leakage and evaporative loss, the design and manufacture of the rest of the cartridge is greatly simplified. In such a preferred embodiment, an assay reagent release mechanism would preferably be incorporated within the cartridge reader for releasing the assay reagent from the reagent module. The assay reagent release mechanism is preferably adapted and configured to engage the reagent module and release/recover its contents.

Figure 19:
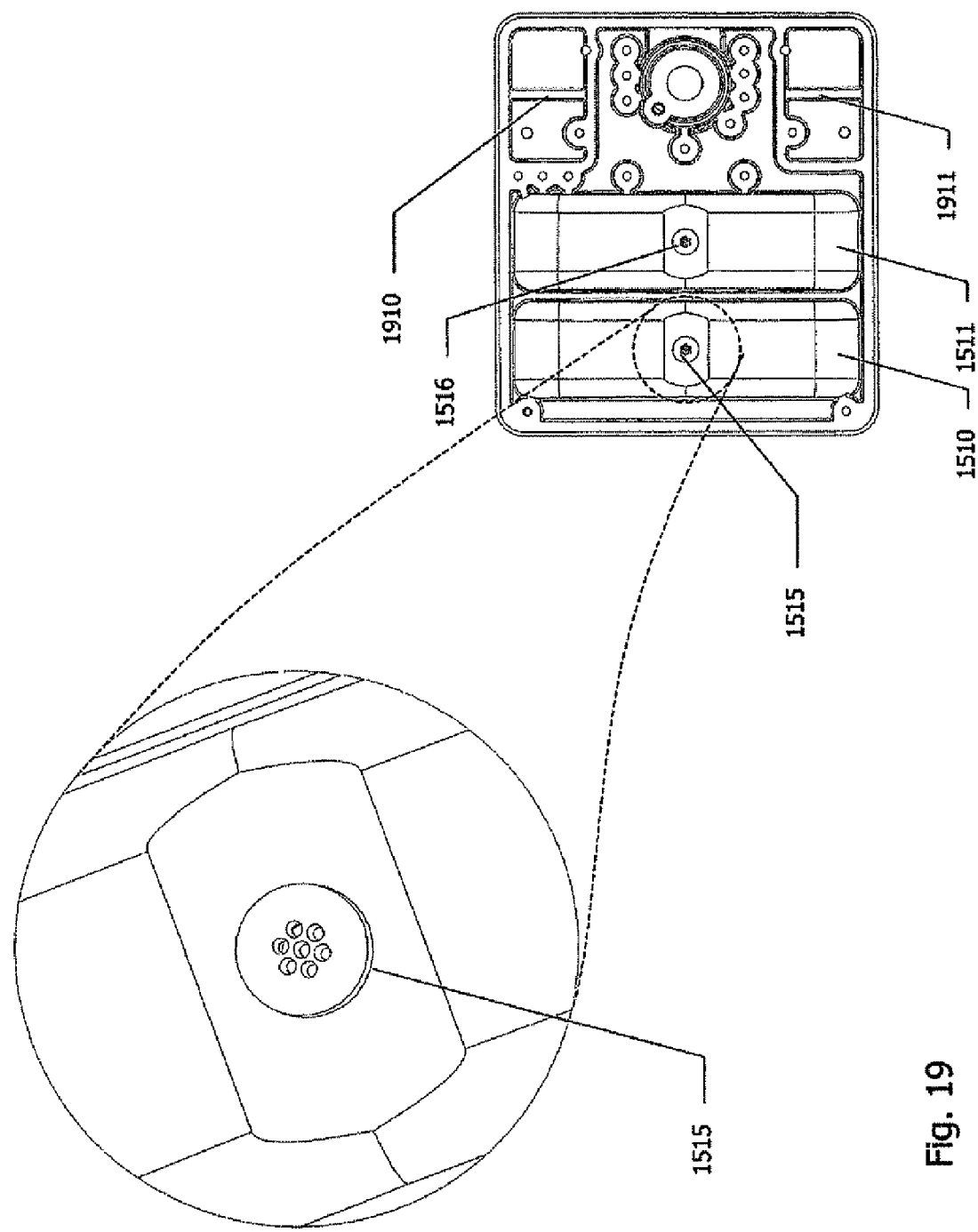
FIG. 19 is a bottom view of the upper cartridge component of the assay cartridge depicted in FIG. 14b illustrating one embodiment of integral filters.

The reagent module is a container such as an ampoule (e.g., glass, plastic, or the like), a pouch (e.g., plastic, metal foil, plastic/metal foil laminates, rubber, or the like), a blister pack, a syringe, or the like, or any other container that can be filled with fluid, sealed and dropped into the cartridge for subsequent fluid delivery. Preferred materials include glass, plastics with good water vapor barrier properties (e.g., cyclic olefin copolymers such as copolymers of ethylene and norbornene, nylon 6, polyethyelene naphthalate, polyvinylidene chloride and polychlorotrifluoroethylene) and metal foil/plastic laminates because of their chemical inertness and their resistance to evaporative losses, other suitable materials will be apparent to the skilled practitioner. Ampoules, preferably, comprise a material that can be made to shatter or break on impact such as glass or hard plastic. Embodiments incorporating breakable ampoules preferably also include filters to ensure that substantially all of the fragments that may result upon rupturing the ampoules are not permitted to enter the fluidic network and possibly obstruct/block fluid flow. FIG. 19 depicts a cutaway top view of a cartridge showing filters 1515, 1516 at the bottom of chambers 1510 and 1511. These filters may be integrally molded/machined, etched/etc. into the corresponding chambers. Alternatively, as illustrated in FIG. 20 depicting a bottom view of a cartridge body, the filters 2020, 2021 may be separate components that are incorporated into the corresponding chambers during the manufacturing/assembly process; e.g., filter inserts that can be inserted/snapped into a receptacle within the chamber that is arranged and configured to engagingly receive the filter insert.

Figure 21:
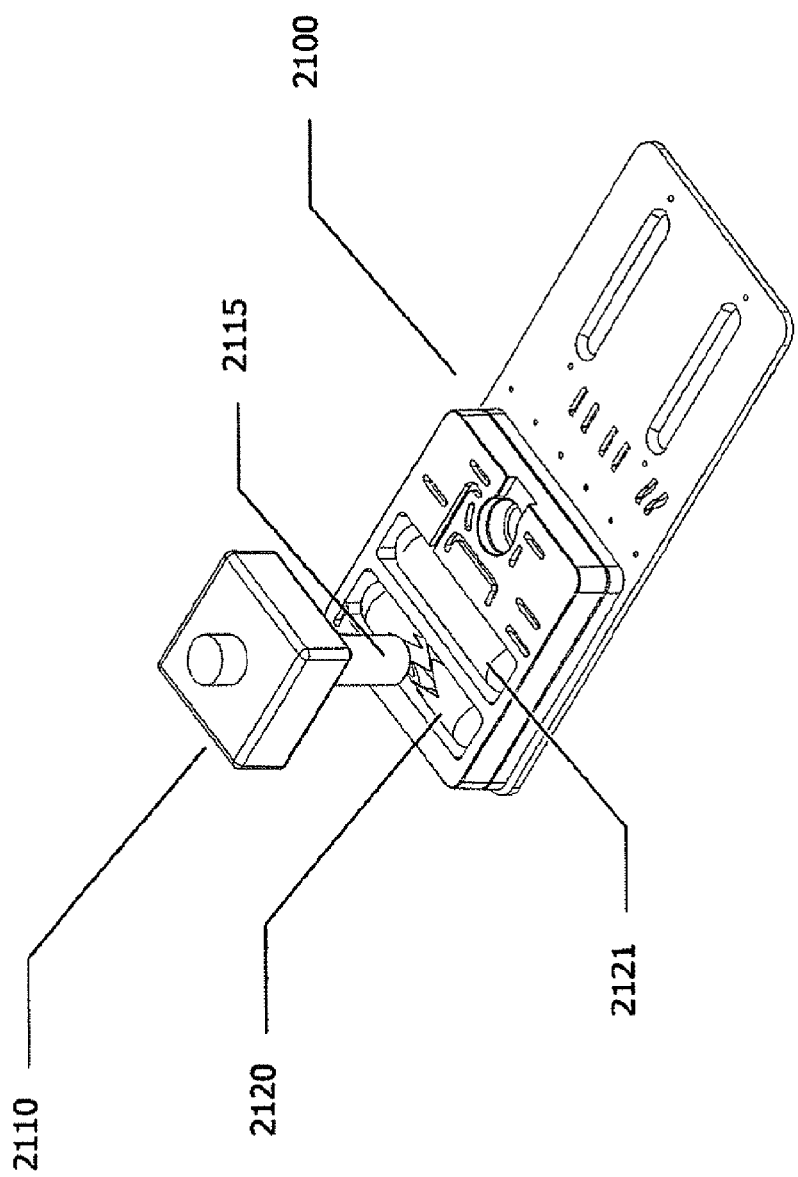
FIG. 21 is an isometric view of the assay cartridge depicted in FIG. 14b having assay reagent ampoules inserted therein, illustrating one embodiment for an assay reagent release mechanism.

The assay reagent release mechanism for releasing the contents of a breakable ampoule may be a simple mechanical device that is actuated to exert a force onto the ampoule; e.g., deliver a sharp blow to the ampoule thereby rupturing it and releasing its contents into the assay reagent chamber. FIG. 21 depicts one preferred embodiment of a reagent chamber employing assay reagent ampoules 2120, 2121. Preferably, a cover layer (not shown), most preferably made from a flexible material, is sealed to the top of the cartridge body so that liquid does not leak from the cartridge after the ampoules are ruptured (see, e.g., cover layer 1401 in FIG. 14). FIG. 21 also shows assay release mechanism 2110 (preferably, a component of a cartridge reader) which can be actuated so that hammer element 2115 strikes an ampoule, preferably by striking a flexible cover layer that then transfers the impact force to the ampoule (while, preferably, remaining intact so that it confines the released liquid to the reagent chamber). It has been observed that striking the ampoule quickly with an adequate impulsive force produces a more complete rupturing of the ampoule and thereby more effectively releasing the assay reagent. Whereas a slowly applied force increasing in magnitude until ultimately the ampoule fractures results in less complete rupture and less effective assay reagent release.

Figure 22:
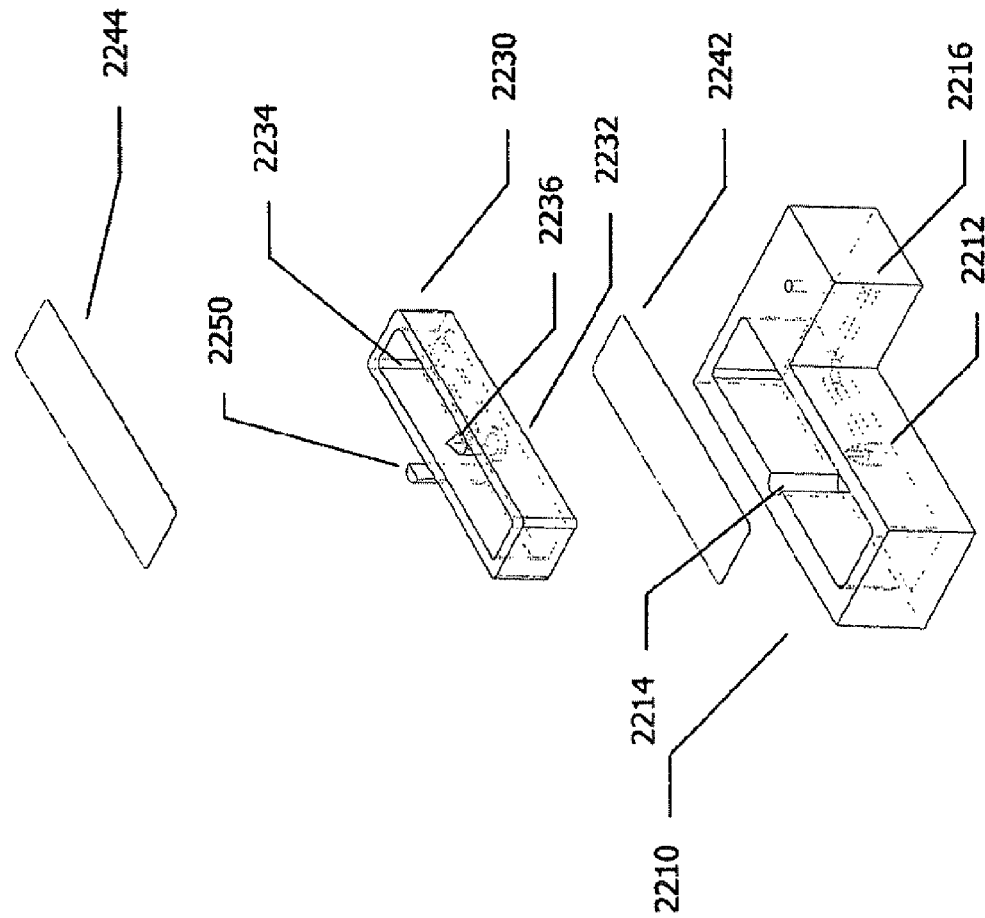
FIG. 22 illustrates one embodiment for a drop-in assay reagent blister pack assembly and integrated assay reagent release (piercing) mechanism.

In an alternative embodiment, a pierceable container such as a pouch or blister pack may be employed. Preferably, the pierceable container has a pierceable wall made from a plastic film, a metal foil, or most preferably, a metal foil/plastic film laminate. In such an embodiment the assay reagent release mechanism could employ a piercing scheme. FIG. 22 shows an exploded view of one preferred embodiment of a reagent chamber for holding a pierceable container. Reagent chamber 2210 has piercing tip 2212 located at the bottom of the chamber. Chamber 2210 is connected to reagent conduit 2216 and, optionally, a vent conduit (not shown). Reagent module 2220 comprises module body 2230, preferably made of injected molded plastic, that defines the walls of a fluid compartment, having a first opening 2232 and a second opening 2234. Fluid is sealed in the compartment by first opening cover 2242 and second opening cover 2244, the covers preferably made of a plastic-metal laminate (most preferably and aluminum coated mylar film). Module 2220 also, preferably, has tongue 2250 that fits in chamber groove 2214 so as to properly align module 2220 in chamber 2210 and hold module in an elevated position above piercing element 2212. Chamber 2210 also, preferably, has a chamber cover layer that prevents leakage of reagent from the chamber after rupture of module 2220. On application of a threshold downward force to module 2220, preferably through a flexible chamber cover layer, module 2220 is pushed against tip 2212, piercing first opening cover 2242 and releasing the reagent into the chamber. Module 2220 also, preferably, comprises a second piercing tip 2236 that is attached to the module walls via a cantilever (the second piercing element and cantilever are preferably integral to the module body; such a component is readily manufacturable, e.g., by injection molding). When piercing tip 2212 pierces first opening cover 2242 in a module with a second tip element 2236, piercing tip 2212 pushes second piercing tip 2236 until it pierces second opening cover 2234 making a second opening in module 2220 and facilitating extraction of the fluid from the pouch; i.e., venting the pouch itself.

In another alternate embodiment, liquid reagents are stored in a syringe comprising a syringe chamber and a plunger. The chamber may be an integral component of the cartridge, a module that is inserted into the cartridge or a separate component that is attached (e.g., via a luer lock connection) to the cartridge prior to use. Actuation of the plunger may be used to release the contents of the syringe into a reagent chamber or, alternately, to transfer the contents directly into other fluidic components of the cartridge.

An important consideration for cartridge based assay systems relates to long term storage of the cartridge prior to use; i.e., "shelf life" of the cartridge. Certain assay reagents (especially biological reagents and/or binding reagents such as enzymes, enzyme substrates, antibodies, proteins, receptors, ligands, haptens, antigens, nucleic acids and the like), when dissolved in a liquid medium require special handling and storage in order to improve their shelf life. In certain instances, even if the assay reagents dissolved in liquid media are handled and stored in strict compliance with the special handling and storage requirements their shelf life is impracticably short. Furthermore, the need to observe special handling and storage requirements adds to the complexity and cost of the cartridge based system employing such reagents. The special handling and storage requirements can be substantially reduced, if not eliminated, and the complexity and cost of the system can be minimized by using more stable dry, or dehydrated, forms of the assay reagents. The use of dry reagents can also simplify mixing operations and reduce the volume and weight of a cartridge. Reagents that may be included in dry form include biological reagents, binding reagents, pH buffers, detergents, anti-foam agents, extraction reagents, blocking agents, and the like. The dry reagent may also include excipients used to stabilize the dry reagents such as sugars (e.g., sucrose or trehalose). For assays may encounter acidic or basic samples (e.g., samples that are inherently acidic/basic and/or samples that are extracted or otherwise treated with an acidic/basic reagent), a dry reagent may include a neutralizing reagent (e.g., an acid, base of a pH buffer). In especially preferred embodiment that involve extraction of samples with nitrous acid, the extracted sample is passed over a dry reagent comprising a base or, more preferably, the base form of a buffering agent (e.g., Tris, Hepes, phosphate, PIPES, etc.). A sufficient amount of the base or buffering agent is included to bring the pH of the extracted sample to a value that is compatible with subsequent assay reactions carried out on the sample (e.g., binding reactions with binding reagents).

Dry reagents may be employed in a cartridge based assay system in a number of ways. As described above, dry reagents may be stored in a reagent chamber that is filled prior to use by a user or by a cartridge reader apparatus. Similarly, dry reagents may be stored in other fluidic components such as within fluidic conduits or chambers, most preferably within a fluidic conduit connecting the sample and detection chambers. Introduction or passage of liquid (e.g., a liquid sample or a liquid reagent) through the conduit or chamber results in dissolution of the dry reagent. Dry reagents may be inserted during the manufacture of a cartridge by depositing the dry reagents in the appropriate fluidic component, e.g., by depositing the reagent in the form of a powder or pellet or by incorporating the dry reagent in a screen printed ink. Alternatively, the reagents may be inserted in solution and then dried to remove the solvent. In one preferred embodiment dried reagents may be formed upon a substrate by depositing solutions containing the reagents in one or more predefined locations and subsequently drying the reagents to form a dried reagent pill under conditions such that on addition of a liquid sample or an appropriate solvent, the dry reagent dissolves into solution. The term "pill" is used herein to refer generally to an amount of a dry, but redissolvable, reagent on a substrate and not to connote any specific three dimensional shape. The location of a pill on a substrate is referred to herein as a "pill zone". The substrate is preferably a component of the cartridge, e.g., cartridge body, chamber, cover layer, electrode array, etc. Suitable locations for the pill zone include the sample chamber, reagent chamber, sample conduits, and reagent conduits so that liquid reagents and samples pick up the dry reagent prior to their introduction to the detection chambers. Alternatively, the reagent pills may be located within the detection chambers themselves. In the preferred embodiment depicted in FIG. 13a, the dried reagent pills are formed upon the cover layer 1322 in two predefined pill zones. In another preferred embodiment, a reagent chamber holds a liquid reagent in an ampoule and a dry reagent pill, so that the dry reagent is reconstituted upon rupture of the ampoule. This arrangement is useful for preparing a reagent containing a reactive component. In one example, the ampoule contains an acid such as acetic acid and the dry reagent is a nitrate salt so that rupture of the ampoule results in the preparation of nitrous acid.

A pill zone in which dried reagents are deposited may be prescribed by a boundary which confines the volume of a deposited solution (and, therefore, the dried reagent left after allowing the solution to dry) to a specific region of a substrate. According to one preferred embodiment of the invention, a cartridge comprises a pill zone that is bounded by a boundary surface, the boundary surface being raised or lowered (preferably, raised) and/or of different hydrophobicity (preferably, more hydrophobic) than the pill zone. Preferably, the boundary surface is higher, relative to the substrate surface within the pill zone, by 0.5-200 micrometers, or more preferably by 2-30 micrometers, or most preferably by 8-12 micrometers. Even more preferably, the boundary surface has a sharply defined edge (i.e., providing a steep boundary wall and/or a sharp angle at the interface between the pill zone and the boundary). Preferably, the pill zone surface has a contact angle for water 10 degrees less than the boundary surface, preferably 15 degrees less, more preferably 20 degrees less, more preferably 30 degrees less, even more preferably 40 degrees less, and most preferred 50 degrees less.

In one preferred embodiment the pill zone is defined by a depression cut or molded into the substrate. In another embodiment, the boundary surface around a pill zone is defined by a boundary material applied on the substrate. In one example, the pill zone is defined by a cutout in a film or gasket applied to the substrate, preferably a cutout in a film of adhesive tape. In another preferred embodiment the boundary can be physically defined by applying a coating in a manner which defines the boundary of the pill zone using, e.g., established techniques for forming patterned coatings such as photolithography, patterned deposition, screen printing, etc. In one example, a patterned dielectric coating can be screen-printed onto the surface of a substrate material, the pattern including apertures, the boundaries of which define the pill zone. The reagent can then be dispensed onto the substrate within the pill zone boundary and thereafter dried to form the dried reagent pill.

The waste chambers are chambers adapted to hold excess or waste liquid. In certain embodiments, the detection chamber may also act as a waste chamber. In certain embodiments, however, it is beneficial to have a separate waste chamber, e.g., when carrying out assay formats that involve passing samples through the detection chamber having a volume greater than the volume of the detection chamber or when carrying out assay formats that involve wash steps to remove sample from the detection chamber. Sizing of the waste chambers is preferably done in accordance to the anticipated volumes of sample and liquid reagents that will be used in the assay. Another sizing related factor for the waste chambers that is preferably taken into account relates to the potential for waste fluids, as they enter the waste chamber to foam or bubble. In such instances, where foaming or bubbling is anticipated, the waste chamber volume could be increased sufficiently to avoid any issues that can arise from such foaming or bubbling.

Figure 10:
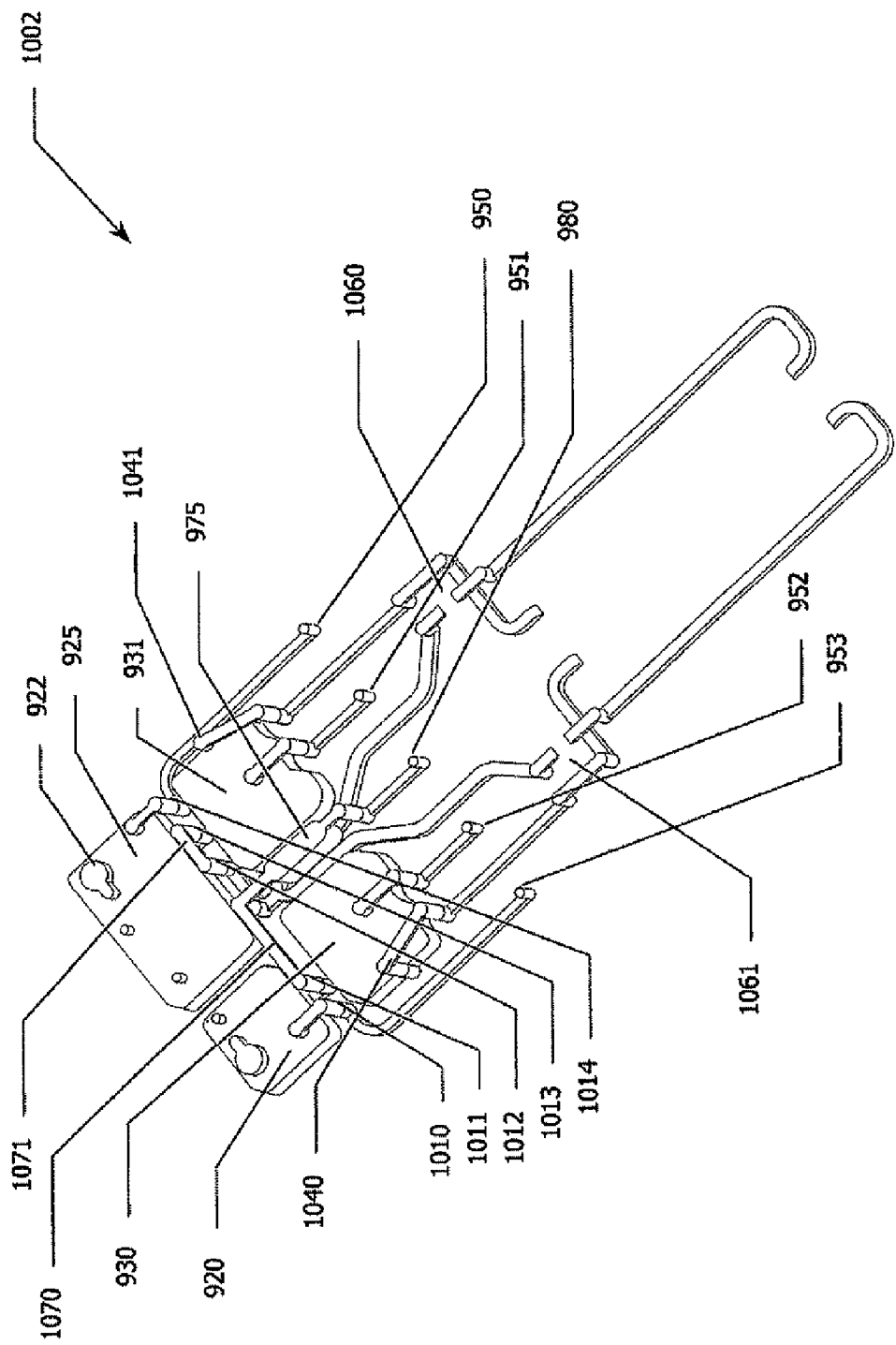
FIG. 10 depicts the fluidic network in accordance with the schematic representation of FIG. 9.

Waste chambers are linked to a waste chamber conduit and, preferably, to a vent port (e.g., through a vent conduit). The waste chamber is configured to allow liquid waste to be delivered to the waste chamber through the waste chamber conduit and, preferably, for air that is included in the waste stream to escape through a waste chamber vent port. Optionally, the waste chambers contain a water absorbing material, such as a sponge, that retains waste fluid and prevents leakage of the waste fluid on disposal of a cartridge. A factor that is preferably considered when designing the configuration and arrangement of the waste chambers relates to eliminating or substantially reducing the possibility that fluid from the waste chamber can flow back ("back-flow") into the cartridge's fluidic network. In particularly preferred embodiments, as illustrated in FIG. 10, the waste chamber conduits are arranged/routed such that they are fluidically connected to the waste chambers at points 1040,1041 that are above the anticipated fill levels/lines (i.e., the fill level/line is defined by the volume of waste fluid that resides within the waste chamber at the conclusion of the assay). This preferred configuration substantially reduces or eliminates the possibility that fluid from the waste chamber can flow back ("back-flow") into the cartridge's fluid network.

The issue of back-flow may also arise in the context of bubbling/foaming of the waste fluids. The vent port is preferably linked via a conduit with a large enough volume to allow a small amount of liquid to enter the conduit (e.g., because of foam in the waste chamber) without this liquid reaching the vent port (as described for above for the sample chamber). Furthermore, aerosol-prevention plugs or gas-selective membranes (i.e., materials that selectively allow the passage of gas but prevent the passage of liquids) may be included into the waste chamber vent conduits or vent ports to prevent release of liquid through these passages. Aerosol-prevention plugs are commonly used in pipette tips to prevent contamination of pipettors and include materials that allow the passage of air when dry but swell and seal up the passage when they come in contact with liquid (e.g., filter materials impregnated or coated with cellulose gum).

An additional measure for eliminating or substantially reducing foaming/bubbling of waste fluids as they are introduced into the waste chamber can be employed in particularly preferred embodiments. Such an additional anti-foaming/bubbling measure may include arranging/routing the waste chamber conduit such that it enters the waste chamber at a position that is located above the fill line and that intersects a vertical wall of the waste chamber, as illustrated by conduit segments 910 and 911 entering waste chambers 930 and 931 in the embodiment depicted in FIGS. 9 and 10. Such a configuration allows the waste fluid to be introduced into the waste chamber in a manner so as to allow the fluid to run along a vertical wall of the waste chamber. Advantageously, this substantially reduces or eliminates foaming/bubbling of the waste fluid as it is routed into the waste chamber.

Yet another anti-foaming/bubbling measure that may be employed in certain preferred embodiments comprises a vertical web, or partial wall, that can be included in the upper portion of the waste chamber. A particularly suitable embodiment for inclusion of such an anti-foaming/bubbling measure is the two-piece cartridge body design depicted in FIG. 16. The anti-foaming web/wall is preferably included in the upper portions of the waste chambers 1610,1611 located in the upper cartridge component 1500. Preferably the anti-foaming web is arranged between the waste chamber vent and the waste chamber input. The height of the anti-foaming web preferably extends the fill depth of the upper portion of the waste chamber but may be less than the full depth as well. Alternatively, the anti-foaming web can extend beyond the depth of the upper portion of the waste chamber so that it protrudes into the lower portion of the waste chamber. Preferably the height of the anti-foaming web is selected to achieve optimum anti-foaming by allowing the flow of liquid under the web/wall but blocking the flow of bubbles above the surface of the liquid in the waste chamber.

Yet another anti-foaming/bubbling measure is to include an anti-foam agent in the waste chamber or in another conduit or chamber of the cartridge so that liquid entering the waste chamber has less propensity to foam and/or form bubbles.

The detection chambers are adapted for carrying out a physical measurement on the sample. The detection chamber is connected to an inlet conduit. Preferably, the detection chamber is also connected to an outlet conduit and is arranged as a flow cell. If the measurement requires illumination or optical observation of the sample (e.g., as in measurements of light absorbance, photoluminescence, reflectance, chemiluminescence, electrochemiluminescence, light scattering and the like) the detection chamber should have at least one transparent wall arranged so as to allow the illumination and/or observation. When employed in solid phase binding assays, the detection chamber preferably comprises a surface (preferably, a wall of the chamber) that has one or more binding reagents (e.g., antibodies, proteins, receptors, ligands, haptens, nucleic acids, etc.) immobilized thereon (preferably, an array of immobilized binding reagents, most preferably an array of immobilized antibodies and/or nucleic acids). In an especially preferred embodiment, the detection chamber is an electrochemiluminescence detection chamber as described above, most preferably having one or binding reagents immobilized on one or more electrodes. In one preferred embodiment, the cartridge comprises a working electrode having an array of binding reagents immobilized thereon. In another preferred embodiment, the cartridge comprises an array of independently controllable working electrodes each having a binding reagent immobilized thereon. Preferably, in cartridges employing arrays of binding reagents, at least two elements of the array comprise binding reagents that differ in specificity for analytes of interest. Suitable detection chambers, electrode arrays and arrays of immobilized binding reagents for use in ECL-based cartridge systems are described in detail above and include the embodiments shown in FIGS. 1-4.

The detection chamber is, preferably, arranged in an elongated flow cell design with inlet and outlets at or near opposing ends of the elongated dimension. Depending on the application, manufacturing approach, sample size, etc., the flow cell dimensions can range from nanometers to tens of centimeters and the volume from picoliters to milliliters. Certain preferred embodiment have widths that can range from 0.05-20 mm, more preferably, 1-5 mm and heights (preferably, less than or equal to the width so as to increase, for a given volume, the surface area of the bottom of the detection chamber, especially when this surface is used to immobilize binding reagents) that range from 0.01-20 mm, more preferably, 0.05-0.2 mm. Preferably, the height is less than or equal to the width. Preferably, the detection chamber is designed to accommodate sample volumes between 0.1-1000 uL, more preferably, 1-200 uL, more preferably, 2-50 uL, most preferably, 5-25 uL. In embodiments that are limited by sample volume (e.g., cartridges measuring blood from finger pricks), especially preferred detection chamber volumes are less than 10 uL, more preferably 0.5-10 uL, even more preferably 2-6 uL. The flow cell preferably has a width greater than or equal to the height.

A cartridge may comprise one or more detection chambers. Cartridges comprising multiple detection chambers may comprise separate fluidic systems for each detection chamber (e.g., multiple sample chambers and/or reagent chambers and associated fluidic conduits) so that assays on multiple samples may be carried out in parallel. In certain preferred embodiments, multiple detection chambers are linked to a single sample chamber and may share the use of other fluidic components such as reagent chambers, waste chambers and the like. In these embodiments, the two detection chambers may be used to carry out different sets of assays, thus increasing the number of measurements that can be carried out on a sample relative to a cartridge with one detection chamber. Advantageously, the use of multiple detection chambers allows for carrying out in a single cartridge multiple incompatible measurements, that is measurements that can not be performed in a single reaction volume or benefit from being carried out in separate reaction volumes, e.g., measurements that have different requirements for pH or assay composition or otherwise negatively interfere with each other.

In an alternate embodiment employing a plurality of detection chambers, one or more of a plurality of detection chambers is used as control/calibration chamber for measuring assay control/calibration samples. In one such embodiment, a first and a second detection chamber are each configured to carry out a panel of one or more assays for one or more analytes. One detection chamber (the test chamber) is used to analyze a sample. The other detection chamber (the control chamber) is used to analyze a spiked sample having a predetermined additional amount of the one or more of the analytes of interest (this predetermined additional amount, preferably, being provided by passing the sample through a reagent pill zone comprising the additional amounts). The change in signal between the two chambers allows for the calculation of the responsivity of the signal to changes in analyte and can be used to calibrate the system and/or to determine if the cartridge is functioning properly. In another embodiment employing a control chamber, the control chamber is not used to analyze the sample or a derivative thereof but is used to measure analyte in a separate control or calibrator matrix. The signal in the control chamber may be used for determining background signals (by using a matrix with no analyte), for calibrating the instrument (by using a calibrator matrix with a predetermined amount of analyte to determine calibration parameters) or to determine if the cartridge is functioning properly (by using a control matrix with a predetermined amount of analyte and determining if the signal falls within a predetermined acceptable range).

Figure 31:
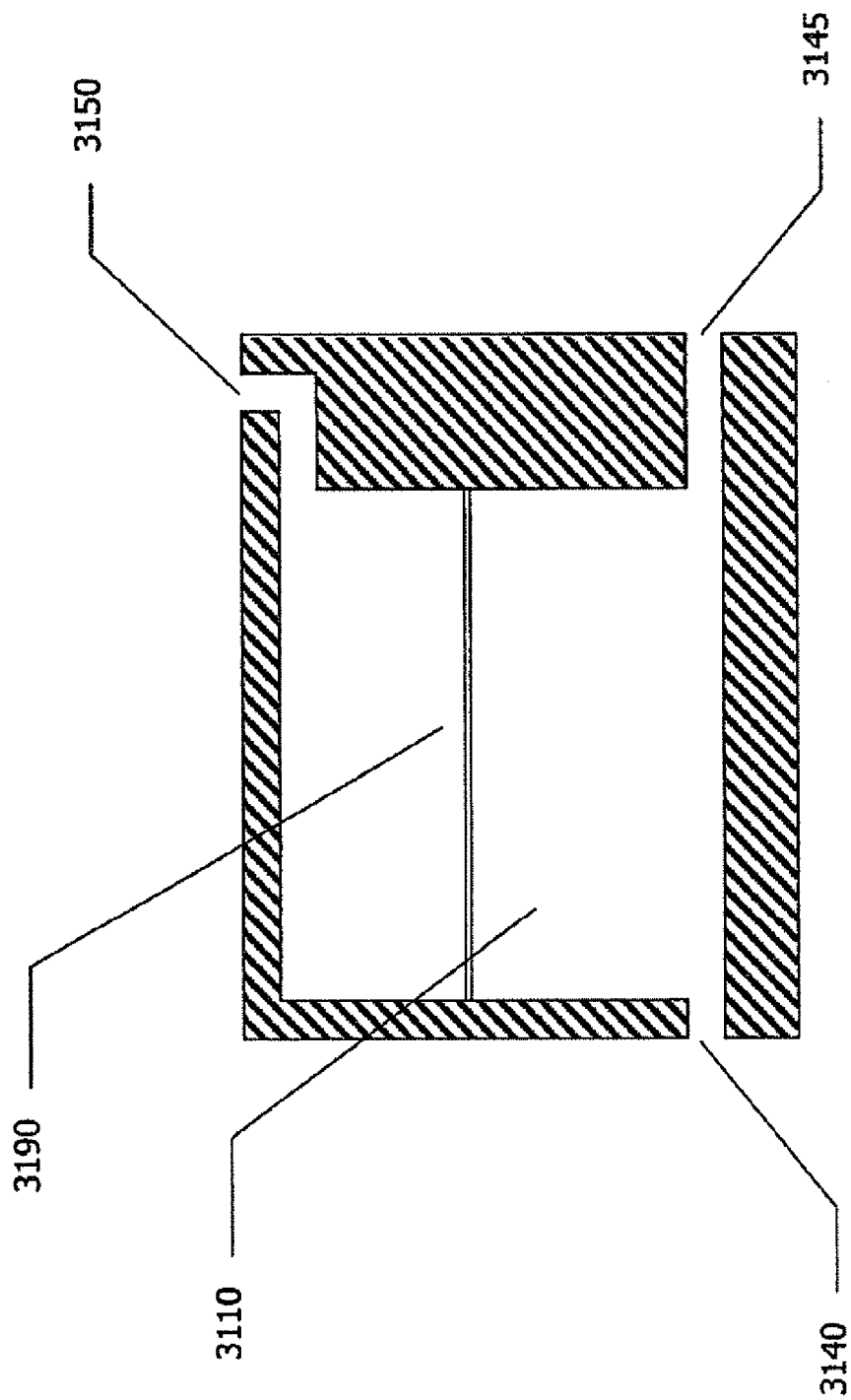
FIG. 31 is a cross-sectional view depicting one embodiment of a bubble trap chamber.

The cartridge fluidics may include bubble traps. The bubble trap is a chamber or conduit adapted for removing bubbles from fluid streams. Preferably, there is a bubble trap between the sample and detection chambers so that bubbles in the sample may be removed prior to introducing the sample into the detection chamber. FIG. 31 shows a cross-sectional view of one exemplary embodiment and shows bubble trap chamber 3110 connected to inlet conduit 3140 and outlet conduit 3145 (the inlet and outlet conduits being, preferably, located near the bottom of chamber 3110) and vent port 3150. Liquid is introduced into chamber 3110 via inlet 3140. Chamber 3110 is, preferably, wide enough so that bubbles in a liquid introduced to the chamber can rise to the top of the chamber and be expelled via vent port 3150. Bubble-free liquid is then expelled via outlet 3145. Optionally, outlet conduit 3145 is omitted; in this case a liquid is admitted via inlet conduit 3140, bubbles are expelled via vent port 3150 and the liquid is then expelled back through inlet conduit 3140. Optionally, an air-permeable but water-impermeable membrane (e.g., a membrane made from Gortex material) is placed between inlet 3140 and vent port 3150. When a liquid passes through the conduit that contains bubbles or is present in a stream that is segmented by slugs of gas, the gas/bubbles will pass through the membrane and exit through vent port 3150 (preferably, the process is aided by applying suction at vent port 3150) to ensure that liquid is not expelled via vent port 3150 (the optional membrane is shown as membrane 3190).

The fluidic conduits can be located at any position within the cartridge and oriented at any angle. Advantageously, the fluidic channels are located, primarily, in planar networks, preferably located proximate to the outside surfaces (e.g., the top 901,902 or bottom 903 surfaces of the cartridge shown in FIGS. 11*a*-*c*) to allow for a multi-layered cartridge design that uses, e.g., machined, die-cut, laser-cut and/or molded cartridge body components. Preferred conduit geometries include conduits with cross-sections that are circular, oval, square or rectangular in cross-section. The width is, preferably, similar to the height so as to minimize the surface area for a particular cross-sectional area. Width and height can vary widely from nm to cm ranges depending on the application, sample volume and cartridge design. Preferred ranges for the width and height are 0.05 to 10 mm, more preferably, 0.5 to 3 mm, most preferably 1 to 2 mm. Cartridges adapted to low volume samples such as blood from finger pricks may have small conduits, preferably having height/widths <1 mm, preferably between 0.4 to 1.0 mm.

The fluidic channels preferably make use of "z-transitions" that route the fluid flow path between planes. A conduit with such a z-transition may comprise first, second, and third conduit segments arranged in sequence, the first and third conduit segments being located in different planar fluidic networks and the second conduit segment connecting the two fluidic networks and arranged at an angle to the other two segments. By way of example, "z-transitions" (denoted in FIG. 9 as capillary breaks) route the fluid flow/path, in the cartridge shown in FIGS. 11a-c, from fluidic conduits near the upper surface 901,902 to fluid conduits near the bottom 903 surface and vice a versa. Z-transitions are advantageous in that they provide capillary breaks (as described below) and allow for more complicated fluidic networks than would be possible if the fluidic conduits were confined to one plane. Selective use/placement of capillary breaks, preferably z-transitions, may be used to control the passive flow of fluids and prevent mixing of fluid streams. Certain preferred embodiments of the invention employ "double z-transitions", that is conduits that comprise a first z-transition that directs fluid flow from a first planar network to a second planar network, a second z-transition that redirects fluid flow back to the first planar network and a connecting segment in the second planar network that connects the two z-transitions. Such a double z-transition may comprise first, second, third, fourth and fifth conduit segments arranged in series, the first and fifth segments located in a first planar fluidic network, the third segment located in a second planar fluidic network, the second and fourth segments located so as to direct flow between the two planar networks.

The fluidic network may be formed within the cartridge in a number of different ways, dependent, in part, upon the materials chosen for the cartridge. Any known fabrication method appropriate to the cartridge body material may be employed including, but not limited to, stereolithography, chemical/laser etching, integral molding, machining, lamination, etc. Such fabrication methods may be used alone or in combination. In certain embodiments of the invention, the cartridge comprises a cartridge body and one or more cover layers mated to surfaces of the cartridge body so as to define one or more fluidic networks preferably, planar fluidic networks) therebetween. Similarly, z-transitions and/or ports can be selectively molded into, or machined out of, the cartridge body at predetermined locations to form the fluidic connections between the channels on the upper and lower surfaces.

One preferred embodiment of the cartridge may be fabricated using a "lamination" process whereby the cartridge body's functional surfaces are sealed using cover layers to form the fluidic network. For example, recesses (e.g., channels, grooves, wells, etc.) one or more surfaces of the cartridge body to provide what is referred to herein as "functional surfaces". Sealing/mating of the functional surfaces to cover layers forms a fluidic network comprising fluidic components (e.g., conduits, chambers, etc.) at least some of which are defined in part by the recesses in the cartridge body and in part by a surface of a cover layer. The cover layers are preferably comprised of plastic film such as mylar film. The cover layer may be coated with an adhesive to seal the cover layer against the cartridge layer. Other methods for mating the cover layer to the cartridge body will be known to the skilled artisan, e.g., the seal may be achieved by heat sealing, ultrasonic welding, RF (radio frequency) welding, by solvent welding (applying a solvent between the components that softens or partially dissolves one or both surfaces), by use of an intervening adhesive layer (e.g., a double sided adhesive tape, etc.). Advantageously, cartridge features that are created by patterned deposition (e.g., patterned deposition of electrode or dielectric layers and/or patterned deposition of reagents to form dry reagent pills or to form binding domains with immobilized binding reagents) are created on cover layers so as to take advantage of automation available to process plastic film in large sheets or rolls.

Recesses may be, e.g., molded in, etched in or machined from the cartridge body. By analogy, fluidic components may also be defined, at least in part, by recesses in a cover layer that is mated to a cartridge body. Fluidic components may also be defined, at least in part, by regions cutout from gasket layers disposed between the cartridge body and cover layers. Apertures in the cartridge body and/or cover layers may be used to provide for access ports to the fluidic network, e.g., sample introduction ports, vent ports, reagent addition ports and the like. Vent ports, preferably, allow the equilibration of fluid in the chambers with the atmosphere or to allow for the directed movement of fluid into or out of a specified chamber by the application of positive or negative pressure. Vent ports, preferably, are designed to prevent the leakage of liquid samples or reagents through the ports and may include aerosol-resistance filters, membrane or filter materials that permit air flow but act as barriers to aqueous solutions (e.g., filter or membranes made from porous hydrophobic materials such as Gortex), and materials that are porous to air but seal when they come in contact with aqueous solutions (e.g., cellulose gum impregnated filters).

Preferred embodiments include a cartridge having a cartridge body with a first side and a second, preferably opposing, side and one or more cover layers mated to the first side to form a first fluidic network therebetween and one or more cover layers mated to the second side to form a second fluidic network therebetween. Through-holes through the cartridge body (which may be formed by molding, etching, machining, etc.) may be used to link the first and second fluidic networks and to provide Z-transitions. Additional fluidic complexity can be built into a cartridge by employing a laminated cartridge body having multiple cartridge body layers and additional fluidic networks between these layers; through-holes through the various cartridge body layers are used to link the different fluidic networks.

A high degree of control over the movement of liquids in the cartridges of the invention may be attained, without the introduction of active valve elements in the cartridge, through the use of fluidic networks comprising capillary breaks. "Capillary break", as used herein, refers to a region in a fluid conduit that acts as a barrier to liquid moving through the conduit under capillary action or under the driving force of a low pressure gradient below a threshold pressure. In preferred examples of capillary breaks, application of a pressure above the threshold pressure acts to push the fluid past the barrier. Capillary breaks may be designed into fluid conduits by introducing, e.g., i) a transition, on a surface of a conduit, from a wettable surface to a less wettable surface (e.g., as indicated by the contact angle for water); ii) a transition in conduit width from a region of narrow width that promotes capillary flow to a region of wider width; iii) a transition, on a surface of a conduit, in roughness; iv) a sharp angle or change in direction and/or v) a change in cross-sectional geometry. In another embodiment, a fluid conduit has a flexible wall/diaphragm that impinges into the conduit and blocks flow driven by a pressure below a threshold pressure. Application of a higher pressure forces the flexible wall/diaphragm out of the flow path and lets fluid flow. Preferably, the diaphragm is made of a material (e.g., Gortex) that allows gas to pass through but prevents the flow of liquid up to a certain pressure. Preferred capillary breaks involve a sharp angle or change in direction in a fluid conduit, most preferably a "Z-transition" as described above.

In one embodiment of the invention, a liquid is introduced into a chamber comprising an outlet conduit that includes a capillary break (preferably a Z-transition). The liquid enters the outlet conduit but stops at the z-transition. A pressure gradient is then applied (e.g., by applying positive pressure to the chamber or negative pressure to the other end of the conduit) which cause the liquid to flow past the z-transition into the rest of the conduit.

The fluidic network may also comprise valves to control the flow of fluid through the cartridge. A variety of suitable valves (including mechanical valves, valves based on electrokinetic flow, valves based on differential heating, etc.) will be known to one of average skill in the art of assay cartridges or microfluidic devices. In preferred embodiments, however, at least one and more preferably all actively controlled valve elements are external to the cartridge. In one embodiment, a fluid conduit has a flexible wall/diaphragm that in the absence of external force allows fluid to pass through the conduit. Application of an external force on the wall/diaphragm (e.g., from a piston or via the application of gas or hydrostatic pressure) causes the diaphragm to impinge on the conduit, thus impeding the flow of fluid.

The fluidic network may include at least one viscosity measuring conduit, preferably linked to a sample chamber or sample conduit, having an inlet and an outlet. The conduit is adapted so that a liquid sample can be introduced into the conduit and the time it takes the liquid to move between two locations in the conduit can be timed (preferably using sensors such as impedance sensors or optical sensors in the cartridge or an associated cartridge reader). Such an arrangement can advantageously be used to measure clotting times of a blood or plasma sample. For measuring clotting times, the conduit or an upstream component preferably comprises a dry reagent necessary for the specific clotting measurement (e.g., activated clotting time, whole blood clotting time, prothrombin time, thrombin time partial thromboplastin time and the like).

Vent ports as described above are, preferably, apertures on the surface of the cartridge that are in fluidic communication with fluidic chambers or conduits within the cartridge. In a laminated cartridge construction, the vent ports may be provided, for example, by apertures in cover layers that seal against a cartridge body to define planar fluidic networks or alternatively, by through-holes exposed on one surface of the cartridge body that communicate with fluidic networks on the opposing side. The vent ports act as control ports that allow a cartridge reader to control the movement of fluid in the cartridge, e.g., by a combination of sealing one or more ports, opening one or more ports to atmospheric pressure, connecting one or more ports to a source of positive pressure and/or connecting one or more ports to a source of negative pressure. The vent ports may also be used to introduce air into liquid streams passing through the fluidic conduits of the invention, for example, to segment the fluid streams with slugs of air. The introduction of air may be used to prevent mixing of two liquid slugs passed sequentially through a conduit, to clear a liquid from a conduit and/or to enhance the efficiency of a wash step. Preferably, the vent ports are arranged in a single row at a common location along the cartridge body's width. Such an arrangement and configuration of the control points advantageously allows the interface between the cartridge reader and the cartridge to be simplified. For example, using such a preferred configuration allows the cartridge reader to make use of a single fluidic mating device for placing the cartridge into fluidic communication with the cartridge reader. Such a configuration also allows the motion control subsystem(s) to be simplified in that a single motor or actuation device may be used to actuate the fluidic mating device and move it into sealing engagement with the cartridge body.

FIG. 9 is a schematic representation of cartridge 900, one preferred embodiment of a cartridge of the invention that incorporates many of the fluidic features described above. This exemplary embodiment depicts a cartridge comprising an electrode array of the invention as described above. The skilled artisan, however, can readily adapt the fluidic components and design to cartridges employing other detection chamber designs and/or detection technologies. The cartridge schematic shown in FIG. 9 comprises various compartments including a sample chamber 920, assay reagent chamber 925, waste chambers 930 and 931 and detection chambers 945 and 946 comprising electrode arrays 949a and 949b and electrode contacts 997 and 998. Also depicted in FIG. 9 are fluid ports/vents 950-953 and 980 that may be utilized as fluidic control points, vents for allowing a chamber to equilibrate with atmospheric pressure, ports for introducing air bubbles or slugs into a fluid stream and/or as fluidic connections to a cartridge reader. FIG. 9 also depicts a number of fluidic conduits (shown as lines connecting the various chambers) that establish a fluidic network that connects the various compartments and/or fluid ports/vents. The fluidic conduits may comprise distribution points (e.g., branch points such as distribution point 976 that are adapted to distribute a fluid to two or more locations/compartments in a cartridge). Other fluidic features that are shown in FIG. 9 include pill chambers/zones 990,991 for each of the read chambers. FIG. 10 depicts a three dimensional representation of the fluidic network formed by the various fluidic components employed in a preferred embodiment of FIG. 9.

Sample chamber 920 is a chamber defined within cartridge 900 that is adapted for receiving a sample, preferably a liquid sample, to be analyzed in the cartridge. Sample chamber 920 includes a sample introduction port 921, and is linked to vent port 953 through a vent conduit and detection chambers 945 and 946 through sample conduit 901 having sample conduit branches 940 and 941. Preferably, cartridge 900 also includes a sealable closure for sealing sample introduction port 921. Reagent chamber 925 is a chamber adapted to hold a liquid reagent and includes a vent conduit linked to vent port 950 and reagent conduit 902 linked to the sample conduit (preferably, between sample chamber 920 and distribution point 976). Also linked to the sample conduit is air chamber/trap 975 linked to vent port 980. This arrangement allows for adding/removing air into/from the fluid stream(s) (e.g., to reagent or sample streams directed from reagent chamber 925 or sample chamber 920 towards detection chambers 945 or 946) in the fluidic pathway by applying positive pressure or suction to vent port 980. Pill chambers/zones 990 and 991 hold dry reagents and are positioned, respectively, in the fludic pathway between sample port 920 and detection chambers 945 and 946 so that liquid passing through the chamber/zones will reconstitute the dried reagents and carry the resulting solutions into the detection chambers. Reagent chamber 925, air chamber trap 975, vent port 980 and/or pill chamber zones 990 and/or 991 may optionally be omitted.

Detection chambers 945 and 946 are adapted for carrying out a physical measurement on a sample, preferably an electrochemiluminescence measurement, most preferably a measurement employing an electrode array that is configured to be fired in a pair-wise fashion (as described above). Optionally, detection chamber 946 is omitted. As depicted in the preferred embodiment of FIG. 9, detection chambers 945 and 946 have different geometrical cross-sections than their respective input and output channels to which they are in fluidic communication. As such, it is preferable to incorporate transitional fluidic segments (947a,b and 948a,b) at the inputs and outputs of the read chambers such that fluid flow may be appropriately transitioned between the dissimilar regions. Preferably, the transition is designed to minimize the transition length; e.g., incorporating a diffusers/nozzles with as wide an angle as possible, while being gradual enough to prevent trapping of air bubbles. Detection chambers 945 and 946 are connected via waste conduits 960,961 to waste chambers 931 and 930. Waste chambers 930 and 931 are chambers configured to hold excess or waste fluids and are also connected, respectively, to vent port 952 via a vent conduit and vent port 951 via a vent conduit. The use of multiple waste chambers advantageously allows fluid flow through the multiple chambers to be controlled independently via the application of vacuum or pressure to the waste chamber vent ports. Alternatively, only one waste chamber is used (e.g., waste chamber 930 is omitted and detection chambers 945 and 946 are both connected to waste chamber 931).

In cartridges for conducting binding assays for analytes of interest, pill zones 990 and 991 preferably comprise labeled binding reagents (e.g., antibodies, nucleic acids, labeled analogs of analytes of interest, etc.), detection chambers 945 and/or 946 comprise one or more immobilized binding reagents (preferably, an array of immobilized binding reagents, most preferably immobilized on electrodes for conducting ECL assays) and reagent chamber 925 comprises a wash reagent for removing sample solution and/or unbound labeled reagents from the detection chambers. In embodiments where one of the detection chambers is used for control assays or for assay calibration, the associated pill zone may comprise control reagents such as an added analyte (for example, to be used in spike recovery, calibration measurements or control assay measurements).

The fluidic network of cartridge 900 comprises z-transitions that may act as capillary breaks and/or allow for the fluidic network to be extended to multiple planes of the cartridge. See, e.g., Z-transitions 1010-1014 in FIG. 10. Z-transition 1011 in the sample conduit and 1013 in the reagent conduit act as capillary breaks which confine sample liquids and reagent liquids to their corresponding chambers. Fluid can be moved from these chambers, in a controlled and reproducible manner, by application of an appropriate pressure gradient. Z-transitions 1060 and 1061 allows the waste conduits to cross sample conduit branches 940 and 941 by arranging them on different layers of the cartridge.

Figure 11:
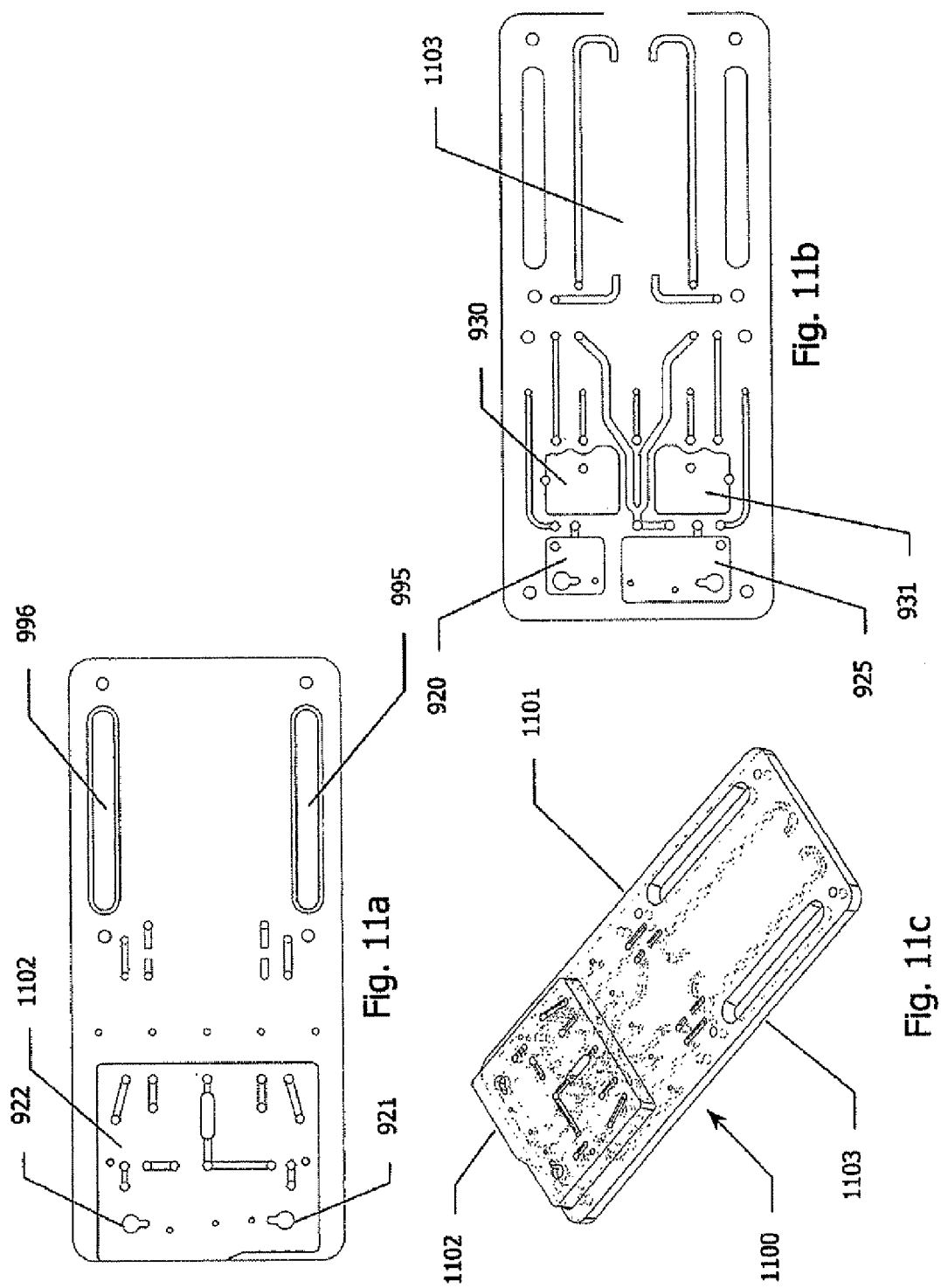
FIGS. 11a-11c are top, bottom and isometric views, respectively, of the assay cartridge of FIG. 9.
Figure 13A:
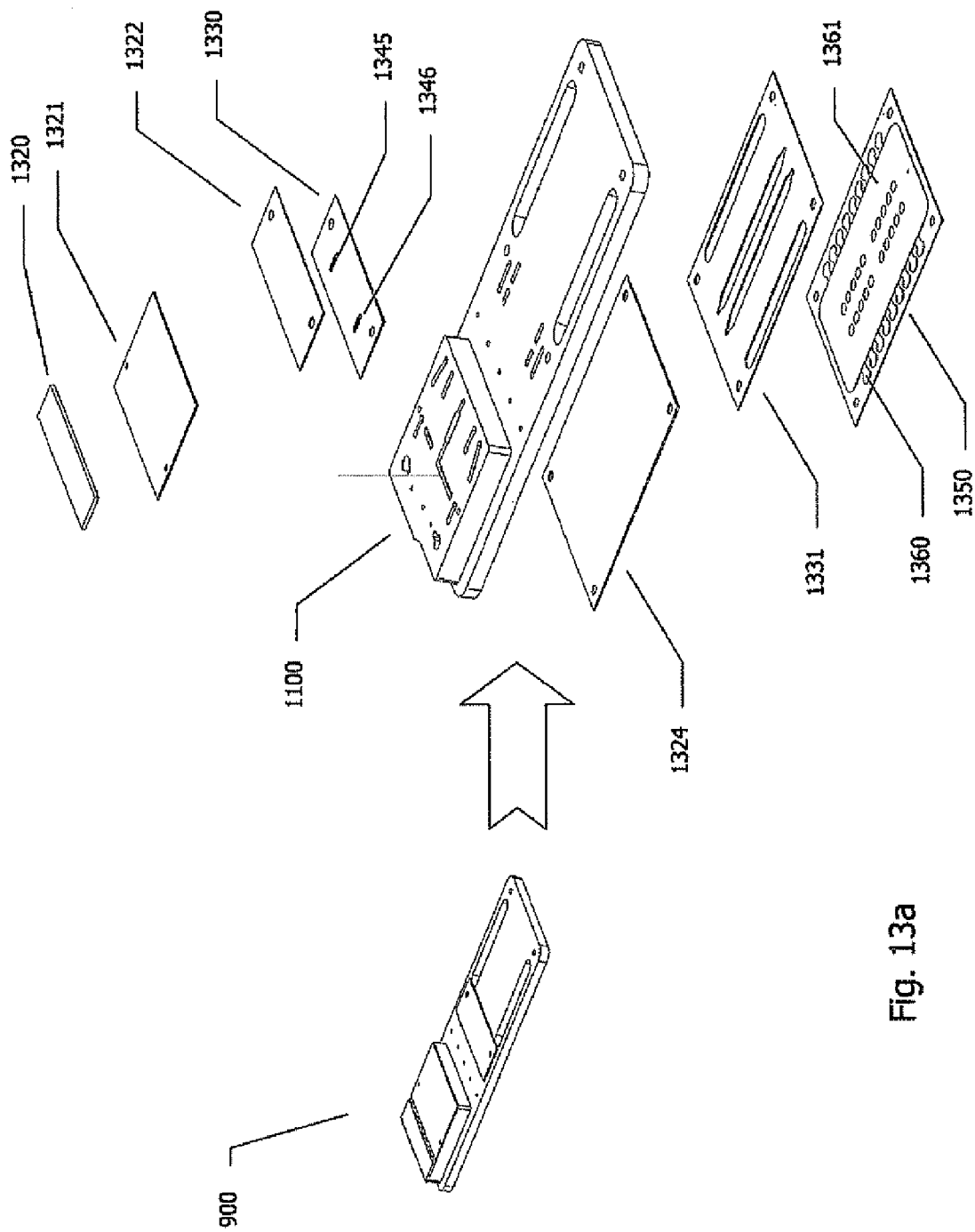
FIG. 13a is an exploded assembly drawing illustrating the laminar assemblage for the assay cartridge depicted in FIG. 9.
Figure 13B:
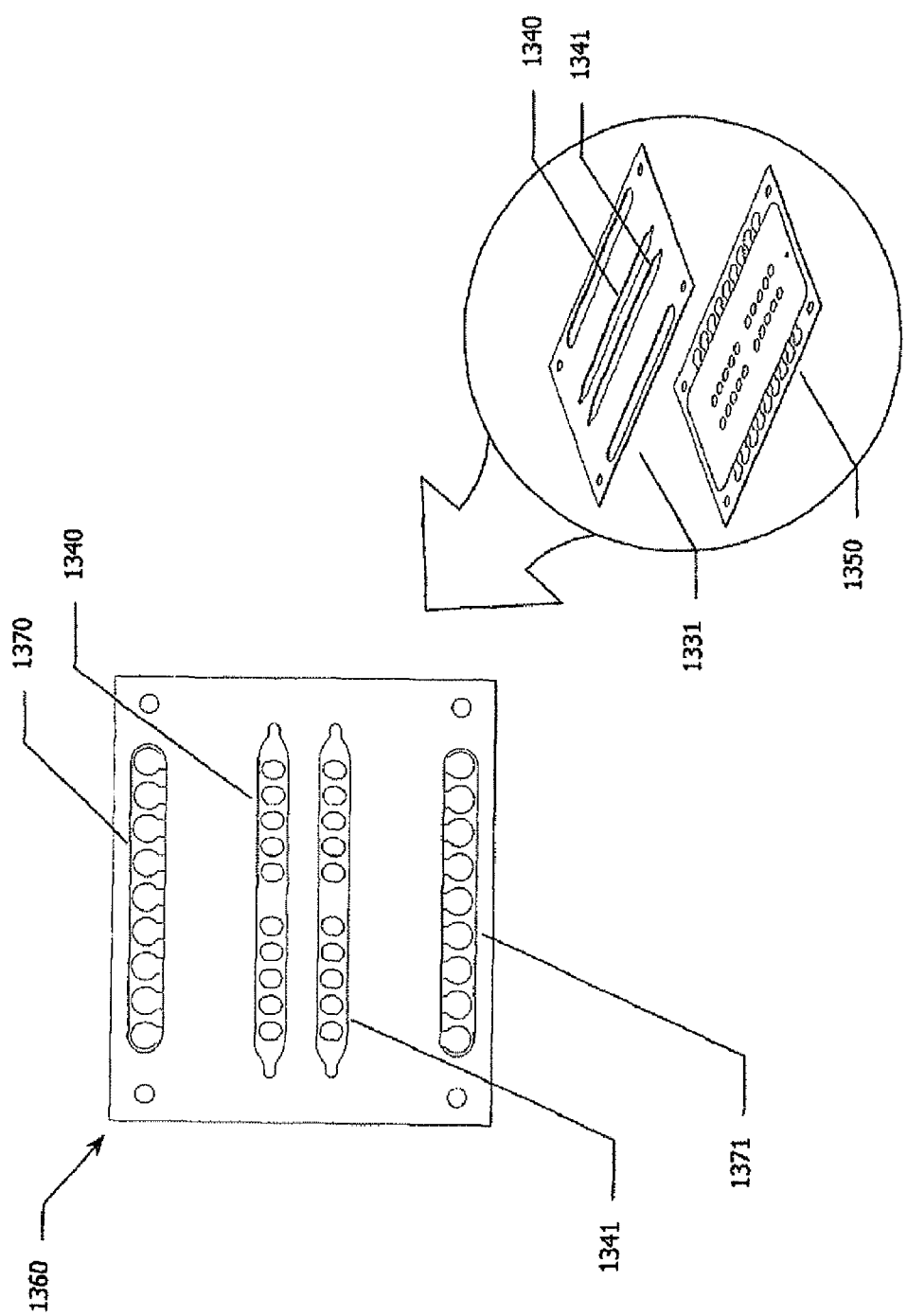

FIGS. 13a and 13b show exploded views of one embodiment of cartridge 900 that comprises cartridge body 1100 and cover layers 1324, 1350, 1320, 1321 and 1322 mated to the surfaces of cartridge body 1100. FIG. 11 shows top (FIG. 11a), bottom (FIG. 11b) and isometric (FIG. 11c) views of cartridge body 1100. The upper 1101,1102 and lower 1103 surfaces of the cartridge body 1100 incorporate (e.g., by molding, machining, etching, etc.) recessed features such as channels, grooves, wells, etc. The features are sealed to provide the chambers and conduits of the cartridge by applying the cover layers to the upper and lower portions of the cartridge body. To allow for adequate sample and/or reagent volumes, the cartridge body has thicker portion 902 which includes features (channels, grooves, wells, compartments, etc.) that define, in part, the sample, reagent and waste chambers. The remainder of the cartridge is, preferably, much thinner so as to minimize cartridge weight, volume and material costs and, in the case, of certain preferred cartridge designs, to allow optical detectors to as close as possible to the top surface of electrodes incorporated on a cover layer on the bottom of a cartridge.

Reagent chamber 925, sample chamber 920, waste chambers 930 and 931 and at least portions of the sample conduit, reagent conduit and waste conduits 960 and 961 are formed by sealing cover 1324 on cartridge body 1100. Detection chambers 945 and 946 are formed by sealing cover layer 1350 (having patterned conductive layer 1360 (which forms the patterned electrode array 963, shown in FIG. 9) and patterned dielectric overlayer 1365) to cartridge body 1100 through intervening gasket layer 1331 (preferably, made from double sided adhesive tape). The detection chamber's depth, length and width are defined by cutouts 1340 and 1341 within the gasket layer. Cover layer 1322 mates to cartridge body 1100 through gasket layer 1330 (preferably a double sided adhesive tape) to define conduit segments, such as 1060 shown in FIG. 10, that (via formation of double z-transitions) act as bridge segments connecting the fluidic networks defined by cover layers 1324 and 1350. Advantageously, the use of a such a "bridge" cover layer allows cover layer 1350 having patterned electrodes (and, optionally, patterned binding reagents on the electrodes) to be only slightly larger than the patterned components. This arrangement decreases the cost of the patterned component. Alternatively, the bridge cover layer and associated double z-transitions can be omitted and cover layers 1324 and 1350 can be combined into a single contiguous cover layer. Optionally, pill zones containing dry reagents pills are located on cover layer 1332 in the regions that are exposed by openings 1345 and 1346 in gasket 1330 so that they the reagents are reconstituted in liquids passing through the pill zones on the way to detection chambers 945 and 946. Cover layer 1321 seals air chamber/trap 976 and the top side conduit segments which include double z-transition connecting segments 1070 and 1071. Cover layer 1320 seals sample introduction port 921 and reagent introduction port 922.

In the preferred embodiment shown in FIGS. 11 and 13, the cartridge body further includes electrical access regions 995 and 996 that, together with cutouts 1370 and 1371 in gasket layer 1331 allow electrical contact to be made with electrode contacts 997,998. Electrical access regions are cut-outs or holes in the cartridge body configured and arranged to be in alignment with the electrode contacts.

Figure 12:
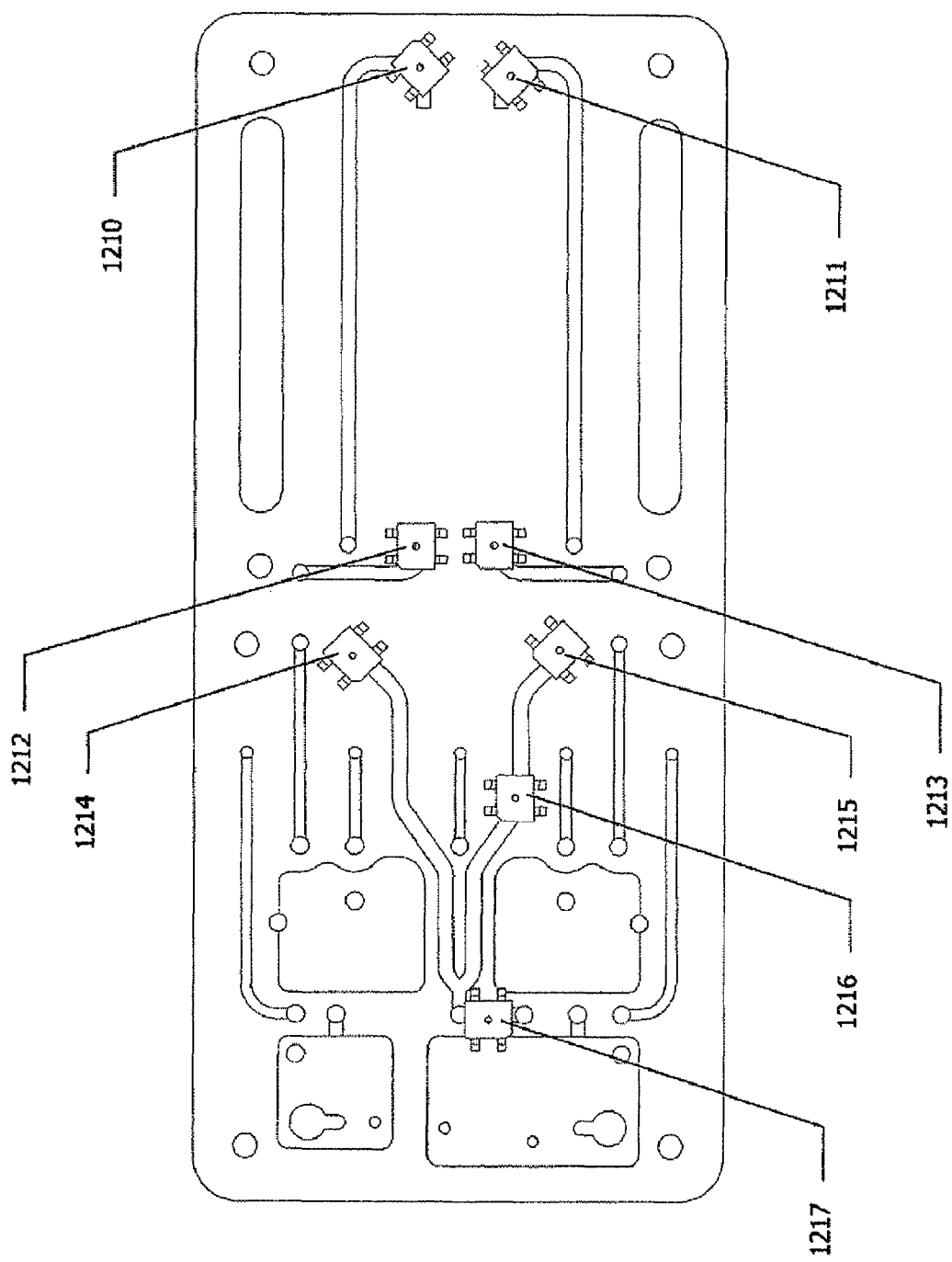
FIG. 12 is a bottom view of the assay cartridge of FIG. 9 illustrating one preferred layout for fluidic detectors to detect/monitor fluid movement.

At least a portion of cartridge body 1100 is adapted and configured to be an optical detection window and is arranged in optical registration with the electrodes to allow optical detection of luminescence generated by the electrode array. In one particularly preferred embodiment, the cartridge body and/or the cover layers are fabricated from a translucent material. The use of optically transparent materials has the further advantage that optical detectors, e.g., detectors arranged within a cartridge reader, can be used to detect the presence of liquids in the conduits. These optical detectors can be used to ensure that the cartridge is functioning properly and to provide feedback to the control systems controlling fluid movement in the cartridge. Alternatively, the cartridge body and/or cover layers may contain optical detection windows that are properly arranged locations that require optical detection of fluid presence and/or composition (e.g., detection of reflectance/transmittance from a light source). FIG. 12 depicts preferred locations for optical detection points 1210-1217 in cartridge 900.

Figure 14A:
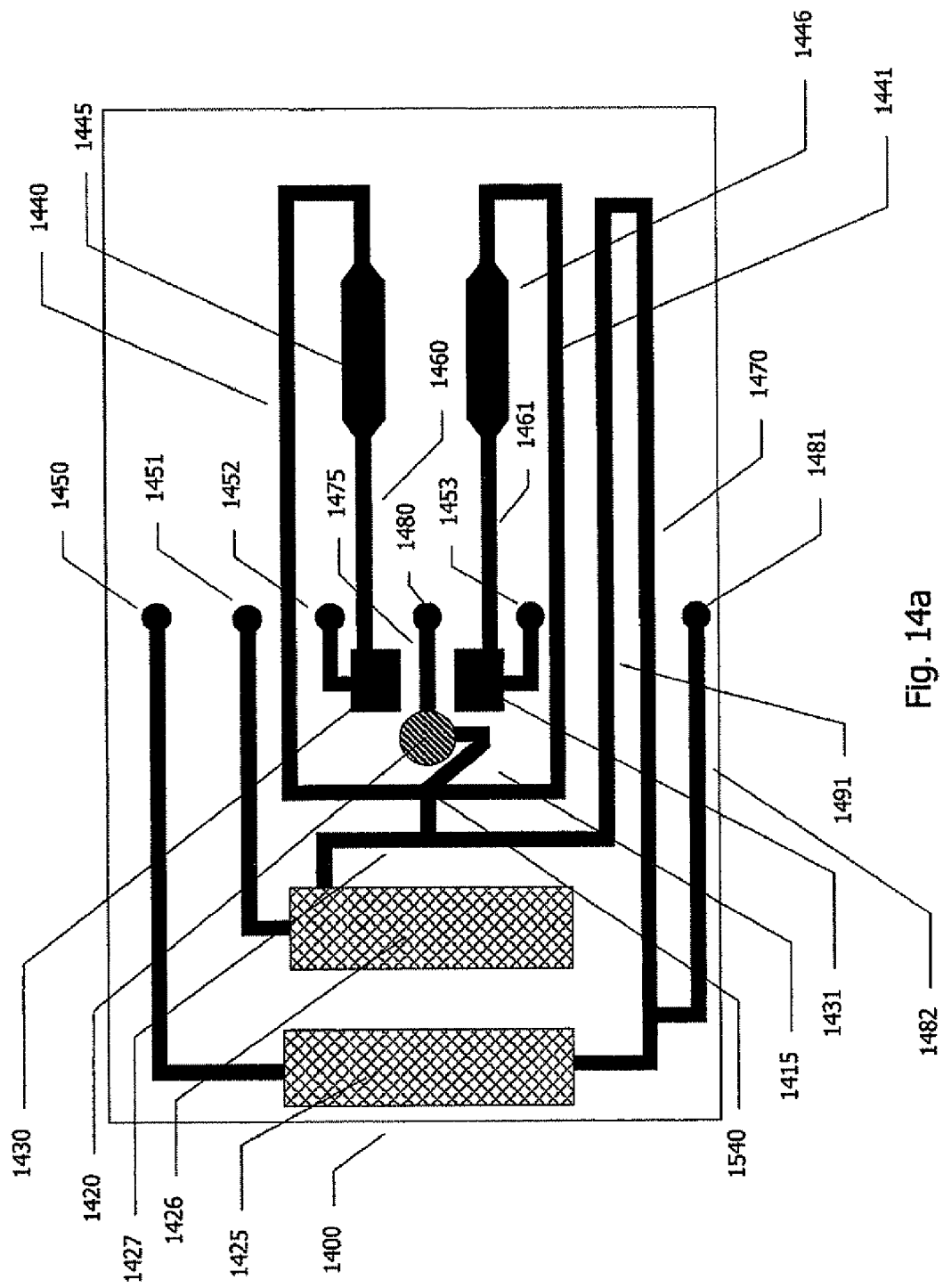
FIG. 14a is a schematic representation of another embodiment of an assay cartridge illustrating various fluidic components.
Figure 14B:
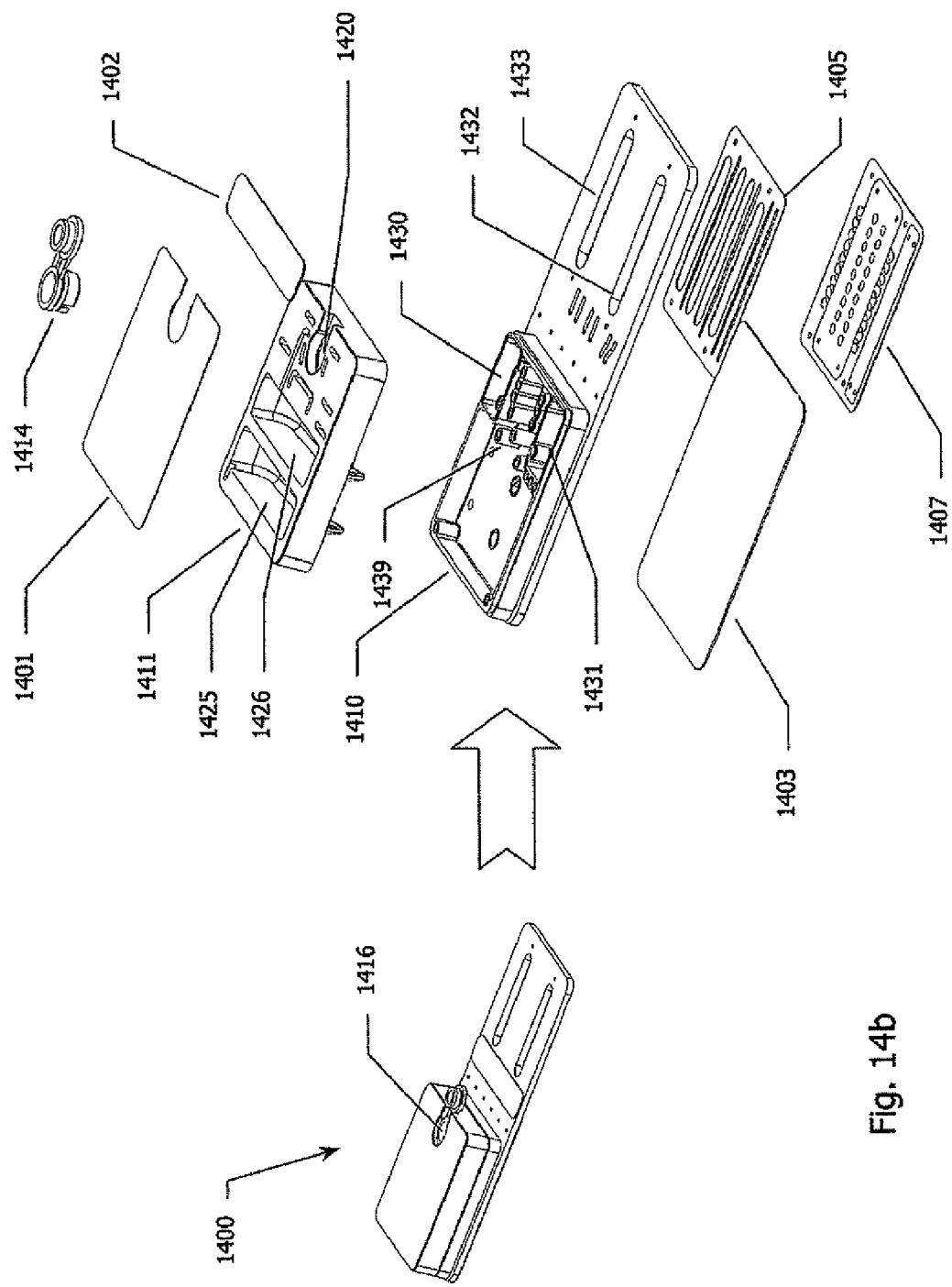
Figure 14C:
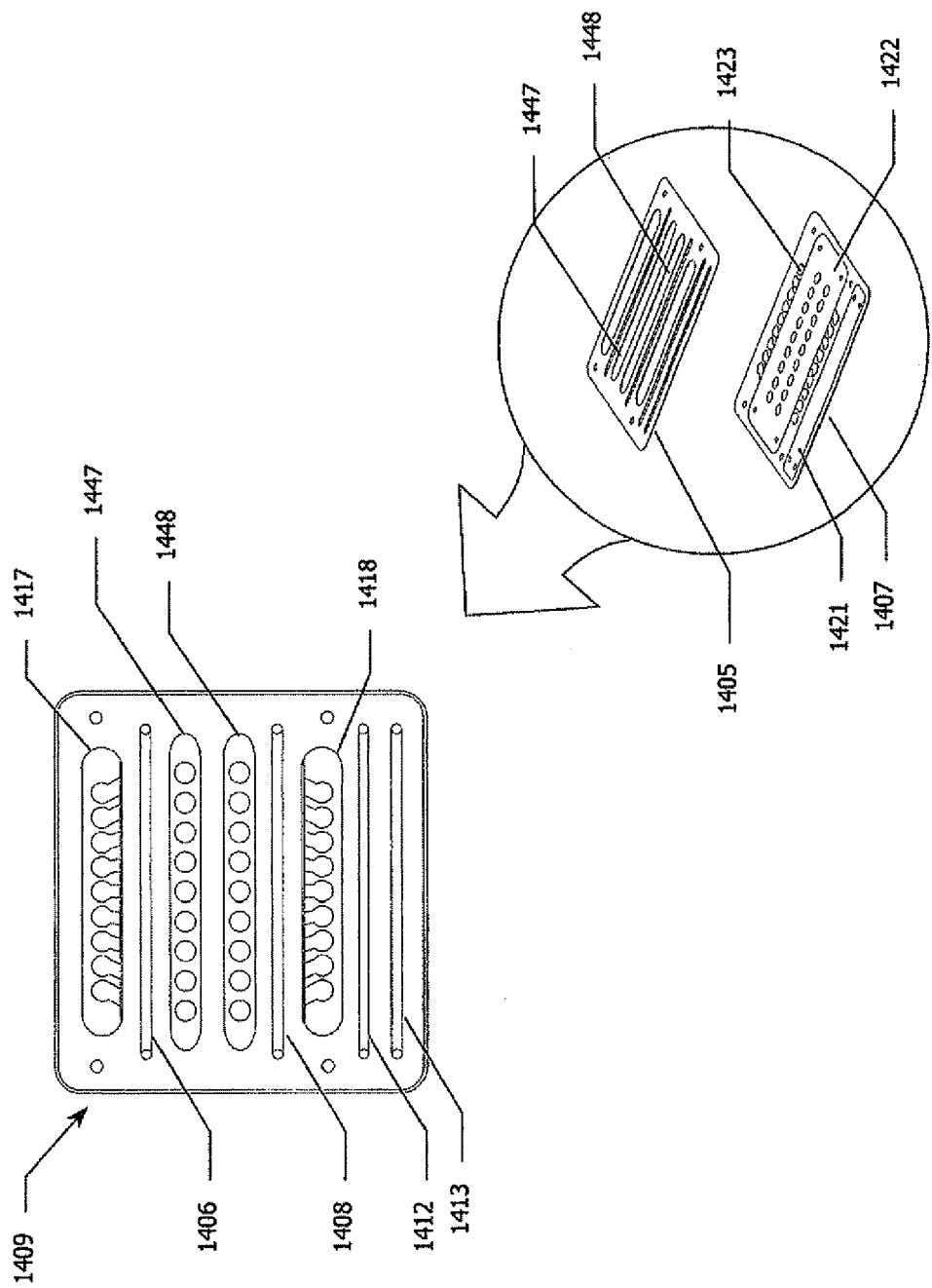
FIG. 14c is a detail drawing of the gasket and electrode array cover layer depicted in FIG. 14b.

FIG. 14a is a schematic representation of the fluidic components of cartridge 1400, another preferred embodiment of the cartridge of the invention. FIGS. 14b and 14c show exploded views of one preferred design of cartridge 1400. FIG. 18 is a three dimensional representation of the fluidic network of this design. Cartridge 1400 comprises a sample chamber 1420, first and second reagent chambers 1425 and 1426, detection chambers 1445 and 1446, waste chambers 1430 and 1431. Sample chamber 1420 is preferably adapted to receive a liquid sample and is linked via vent conduit 1475 to vent port 1480 and via sample conduit 1415 (including sample conduit branches 1440 and 1441 that branch from distribution point 1540) to detection chambers 1445 and 1446. Vent conduit preferably has a serpentine shape to increase its length and prevent fluid from bubbles in sample chamber 1420 from back-flowing into vent port 1480. Sample conduit 1415 preferably comprises a z-transition near the conduit connection to the sample chamber 1420 for preventing premature leakage of sample from sample chamber 1420. Sample chamber 1420 also has sample introduction port 1416 and cap insert 1414 for sealing the port. Optionally, sample conduit branches 1440 and/or 1441 comprise reagent pill zones.

Reagent chambers 1425 and 1426 are, preferably, adapted to hold reagent ampoules. Reagent chamber 1425 is connected via a reagent vent conduit to vent port 1450 and via reagent conduit 1470 to sample conduit 1415. Reagent conduit 1470 is further connected via vent conduit 1482 to vent port 1481 which may be used to introduce air into reagent conduit 1470 and downstream conduits such as sample conduit branches 1440 and 1441. Advantageously, reagent conduit 1470 has an extended segment between vent conduit 1482 and sample conduit 1415 which may be used as a staging area for a defined volume of liquid reagent. Preferably, this extended segment also comprises a reagent pill zone for introducing a dry reagent into the liquid reagent held in reagent chamber 1425. Reagent chamber 1426 is connected via a vent conduit to vent port 1451 and via reagent conduit 1427 to sample conduit 1415 (first intersecting with reagent conduit 1470 just downstream from sample conduit 1415). Reagent conduits 1427 and 1470 preferably comprise Z-transitions near to the connection of the conduits to their corresponding reagent chambers to prevent premature leakage of the reagent from the chambers. Detection chambers 1445 and 1446 preferably, comprise immobilized binding reagents for analytes of interest, preferably an array of binding reagents, preferably an array of binding reagents supported on electrode arrays for conducting ECL measurements, e.g., the electrode arrays of the invention as described above. Detection chambers 1445 and 1446 connect to sample conduit branches 1440 and 1441 and to waste conduits 1460 and 1461. Waste chambers 1430 and 1431 connect to waste conduits 1460 and 1461 and, via vent conduits to vent ports 1452 and 1453. Optionally, one detection chamber (and the associated fluidics and waste chamber) may be omitted.

Cartridge 1400 is adapted to carry out one and two step washed assays (assays that involve treating a detection chamber with one or two samples/reagents prior to conducting a wash step). A preferred embodiment of a one step washed assay comprises: i) introducing sample from sample chamber 1420 into detection chambers 1445 and/or 1446 via sample conduit branches 1440 and/or 1441 (optionally, the sample introduced into the detection chambers including reconstituted reagents such as labeled binding reagents and/or control/calibration reagents picked up in pill zones comprised in sample conduit branches 1440 and/or 1441) ii) washing detection chambers with a wash reagent contained in reagent chamber 1426 (the reagent preferably comprising an electrochemiluminescence coreactant and providing a suitable environment for an ECL measurement) and iii) interrogating the contents of the detection chamber (preferably, by conducting an ECL measurement). For cartridges carrying out such a one step protocol, reagent chamber 1425 may be omitted (in which case, vent port 1481 may be directly connected to reagent conduit 1427 or sample conduit 1415. A preferred embodiment of a two-step washed assay comprises: i) introducing sample from sample chamber 1420 into detection chambers 1445 and/or 1446 via sample conduit branches 1440 an and/or 1441 (optionally, the sample introduced into the detection chambers including reconstituted reagents such as blocking agents, buffers, labeled binding reagents and/or control/calibration reagents picked up in pill zones comprised in sample conduit branches 1440 and/or 1441); ii) introducing a liquid reagent from reagent chamber 1425 into detection chambers 1445 and/or 1446 (optionally, the reagent introduced into the detection chambers including reconstituted reagents such as blocking agents, buffers, labeled binding reagents and/or control/calibration reagents picked up in pill zones comprised in reagent conduit 1470); iii) washing detection chambers with a wash reagent contained in reagent chamber 1426 (the reagent preferably comprising an electrochemiluminescence coreactant and providing a suitable environment for an ECL measurement) and iv) interrogating the contents of the detection chamber (preferably, by conducting an ECL measurement). Optionally, a wash step is included between steps (i) and (ii). Advantageously, the use of a two step format in binding assays allow analyte or other components in a sample to be bound to immobilized binding reagents in the detection chambers and washed out of the detection chamber prior to the introduction of labeled detection reagents (e.g., labeled binding reagents for use in sandwich binding assays or labeled analytes for use in competitive assays); carrying out assays in two steps may be advantageous in competitive assays and assays that suffer from large sample matrix effects or hook effects. Some assays may not require a wash step (e.g., non-washed ECL assays may be carried out by incorporating adding an ECL coreactant to the sample); for cartridges carrying out such non-washed assays (in one or two step formats), reagent chamber 1426 may be omitted.

A shown in FIG. 14b, a preferred embodiment of cartridge 1400 uses a laminar cartridge design employing a two part cartridge body (1410 and 1411) and cover layers 1401, 1402, 1403 and 1407. To allow for adequate sample and/or reagent volumes, the cartridge body has a thicker portion which includes features (channels, grooves, wells, compartments, etc.) that define, in part, the sample, reagent and waste chambers. The remainder of the cartridge is, preferably, much thinner so as to minimize cartridge weight, volume and material costs. The two part cartridge design is not required but is advantageous for producing the cartridge by low cost injection molding techniques by allowing the thicker regions of the cartridge body to be hollowed out thus reducing the amount of material needed to produce a cartridge, reducing the time required to cool the parts before ejection from an injection mold die and reducing the part deformation after release from the mold. In this hollowed out design, through-holes through the cartridge body can be provided for by tubes incorporated into body components 1410 and/or 1411 (see, e.g., tube 1439 in FIG. 14b). These tubes may be mated to tubes or holes in the other body component to form through-holes through the body. This mating can be accomplished by a variety of methods including tube mating methods known in the art. Preferred techniques include plastic welding techniques and/or the use of press fits (preferably, by mating a tapered tube with an outer diameter that decreases from $d_{max}$ to $d_{min}$ at its end with a tube that has an inner diameter between $d_{max}$ and $d_{min}$). In an alternate embodiment, a one part cartridge body is used.

At least portions of the sample, reagent and vent conduits are formed by sealing cover 1403 on lower cartridge body part 1410. Detection chambers 1445 and 1446, portions of sample conduit branches 1440 and 1441, and portions of elongated reagent conduit 1470 are formed by sealing cover layer 1407 (having patterned conductive layer 1423 (which forms a patterned electrode array analogous to the electrode array 963, shown in FIG. 9) and patterned dielectric overlayers 1421, 1422) to lower cartridge body part 1410 through intervening gasket layer 1405 (preferably, made from double sided adhesive tape). The detection chamber's depth, length and width are defined by cutouts 1447 and 1448 within the gasket layer. Cutouts 1406, 1408, 1412, 1413 in the gasket layer expose regions of dielectric layers 1421 and 1422 to sample conduit branches 1440 and 1441 and elongated reagent conduit 1470. Advantageously, dry reagent pills comprised within these reagents are located on these regions. This choice of pill locations allows dry reagent pills and/or immobilized reagents within the detection chambers to be dispensed on a single substrate. Preferably, as shown in FIG. 14, sample conduit branches 1440 and 1441 have segments that are adjacent and/or substantially parallel to detection chambers 1445 and 1446 and a U-turn segment to allow connection to the detection chambers. This arrangement provides for conduit lengths that are long enough to allow for the introduction of a sample to the conduit and mixing of the sample with a pill in the conduit prior to introduction of the sample to the detection chamber. These lengths are achieved without adding to the length of the cartridge. Advantageously, this arrangement also allows the patterned electrode layer to be used to conduct capacitive or conductometric measurements of fluid within the sample conduits as described above. Similarly, elongated reagent conduit 1470 has entrance and return segments, connected via a U-turn segment, that are parallel to detection chambers 1445 and 1446. Lower cartridge body component 1410 further includes electrical access regions 1432 and 1433 that, together with cutouts 1417 and 1418 in gasket layer 1405 allow electrical contact to be made with conductive layer 1423.

Cover layer 1402 mates to lower cartridge body component 1410 to define conduit segments 1805 (readily seen in FIG. 18a) that (by connecting two z-transitions) act as bridge segments connecting the fluidic networks defined by cover layers 1403 and 1407. Optionally, pill zones formed on cover layer 1402 on surfaces of bridge segments comprised within the sample or reagent conduits may be used to introduce dry reagents to the sample or liquid reagents. Cover layer 1401 mates to upper cartridge body component 1411 and seals reagent chambers 1425 and 1426, preventing the release of fluid from ampoules within the chambers. Cover layer 1401 also seals top side conduit segments including double z-transition connecting segments such as segments 1810 and 1815 readily seen in FIG. 18a.

Figure 15A:
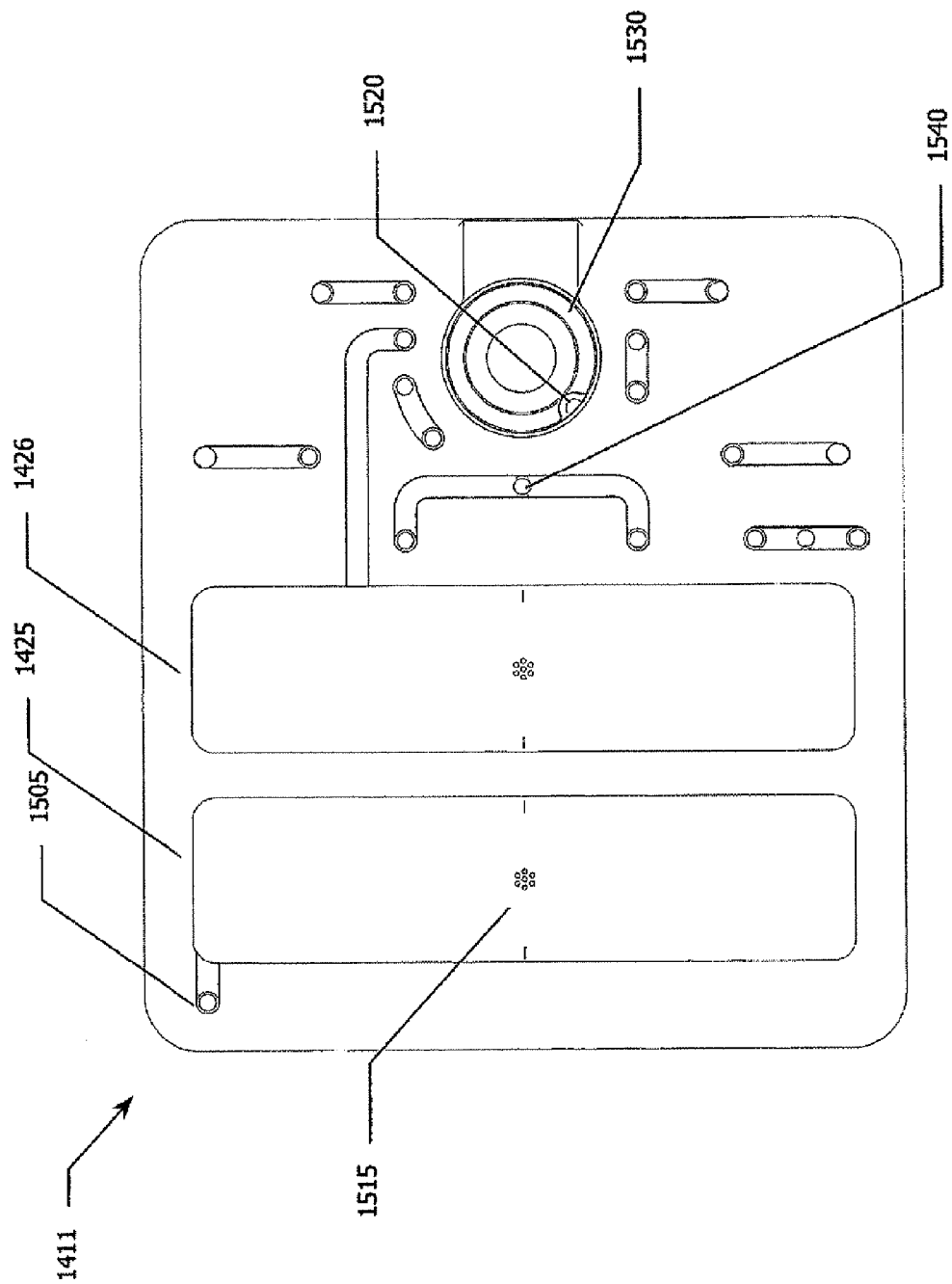
FIG. 15a is a top view of the upper cartridge component of the assay cartridge depicted in FIG. 14b.
Figure 16A:
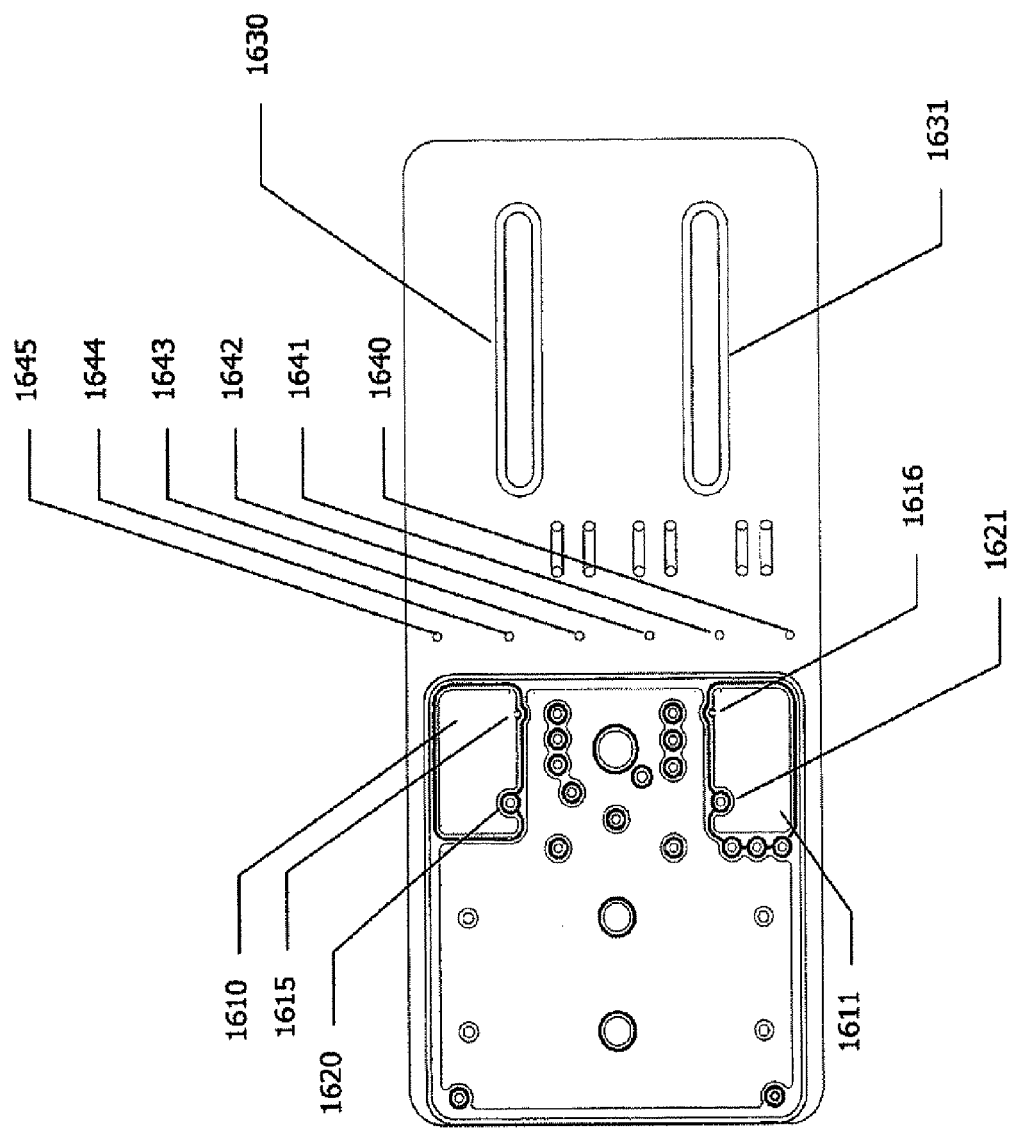
FIGS. 16a and 16b are top and bottom views, respectively, of the lower cartridge component of the assay cartridge depicted in FIG. 14b.
Figure 16B:
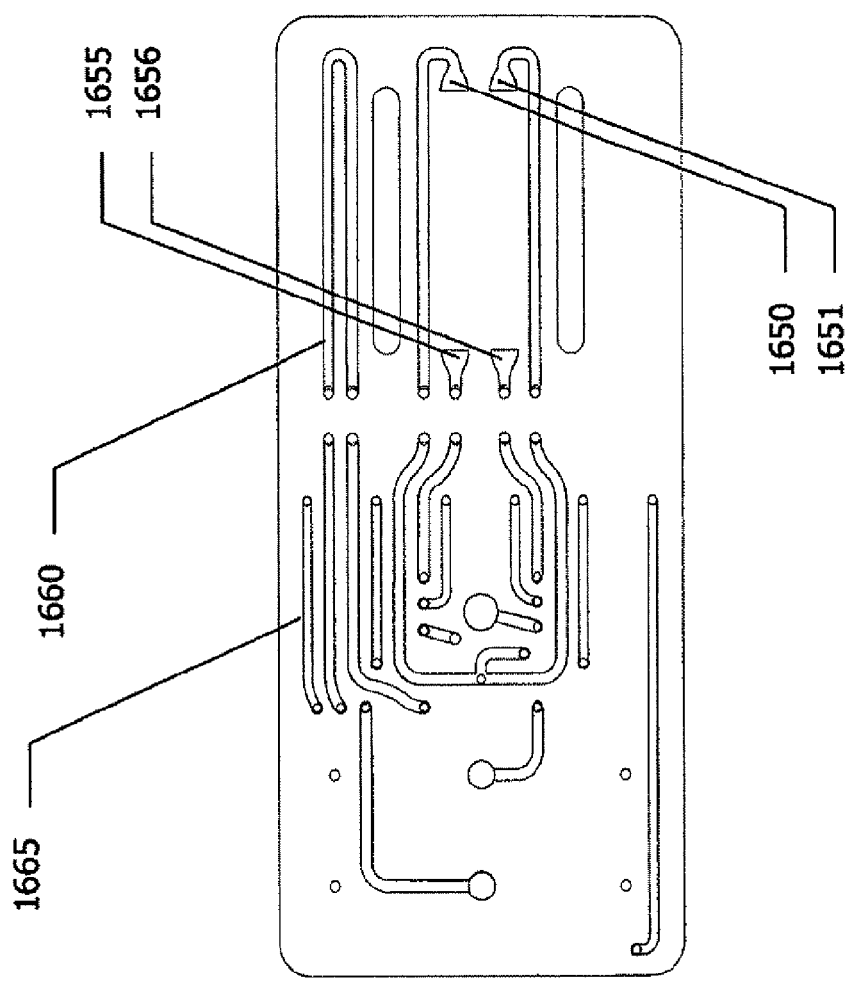

FIG. 15a shows a top view of upper component 1411. FIGS. 16a and 16b show top and bottom views of lower body component 1410. As shown in FIG. 15a, the upper cartridge component 1411 preferably includes reagent chambers 1425, 1426 that are configured to hold reagent ampoules. Filters 1515, 1516 are preferably integrally molded into the upper cartridge component to ensure that substantially all of the glass fragments from the ruptured glass ampoules are not permitted to enter the fluidic network and possibly obstruct/block fluid flow. Alternatively, the filters may be separate components that are incorporated into the sample and/or assay reagent chambers during the manufacturing/assembly process; e.g., inserts that may preferably be snapped into place (see, e.g., inserts 2020 and 2021 in FIG. 20).

The two piece cartridge design also advantageously simplifies the employment of additional anti-foaming measures in the waste chambers. A vertical web, or partial wall, can be included in the upper portions of the waste chambers 1610, 1611 located in the upper cartridge component 1600, another embodiment of upper cartridge component 1411. Preferably the anti-foaming web is arranged between the waste chamber vent and the waste chamber input. The height of the anti-foaming web preferably extends the full depth of the upper portion of the waste chamber but may be less than the full depth as well. Alternatively, the anti-foaming web can extend beyond the depth of the upper portion of the waste chamber so that it protrudes into the lower portion of the waste chamber. Preferably the height of the anti-foaming web is selected to achieve optimum anti-foaming.

As discussed above, the input conduits of the waste chambers are preferably arranged so as to enter the waste chambers in a manner that allows the waste fluid to run down the wall of the waste chamber to minimize or eliminate foaming. As illustrated in FIG. 16a, the input conduits 1615, 1616 intersect one of the walls of the waste chambers. Additionally, the vents are configured and arranged to access the waste chambers at a point that will be above the anticipated fluid level. Locating the waste chamber vents at or near the top of the waste chamber also helps to ensure that any foaming that may occur within the chamber does not result in fluid entering the vent line and possibly contaminating the cartridge reader instrument.

Figure 32:
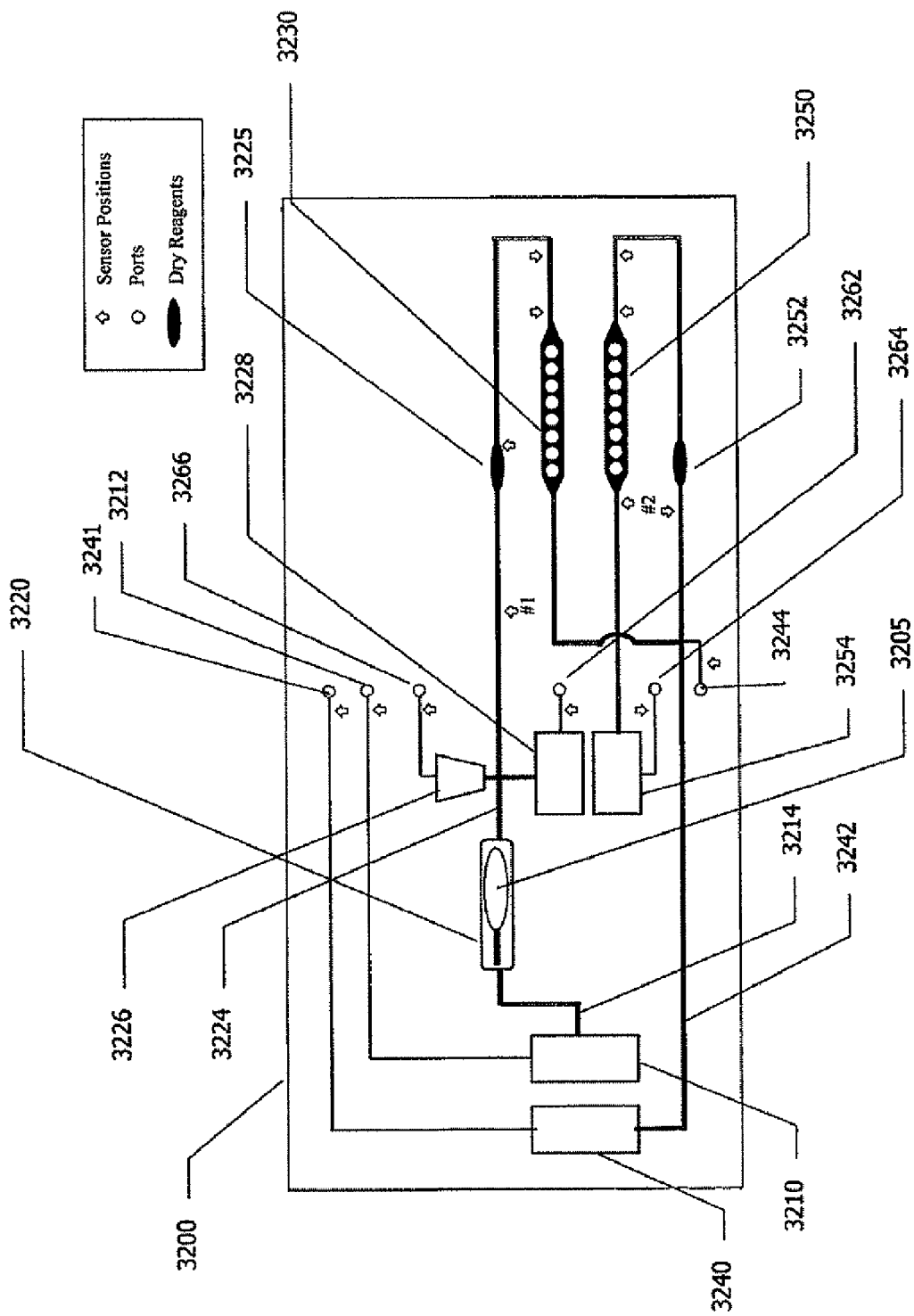
FIG. 32 is a schematic representation of another embodiment of an assay cartridge illustrating various fluidic components.
Figure 33:
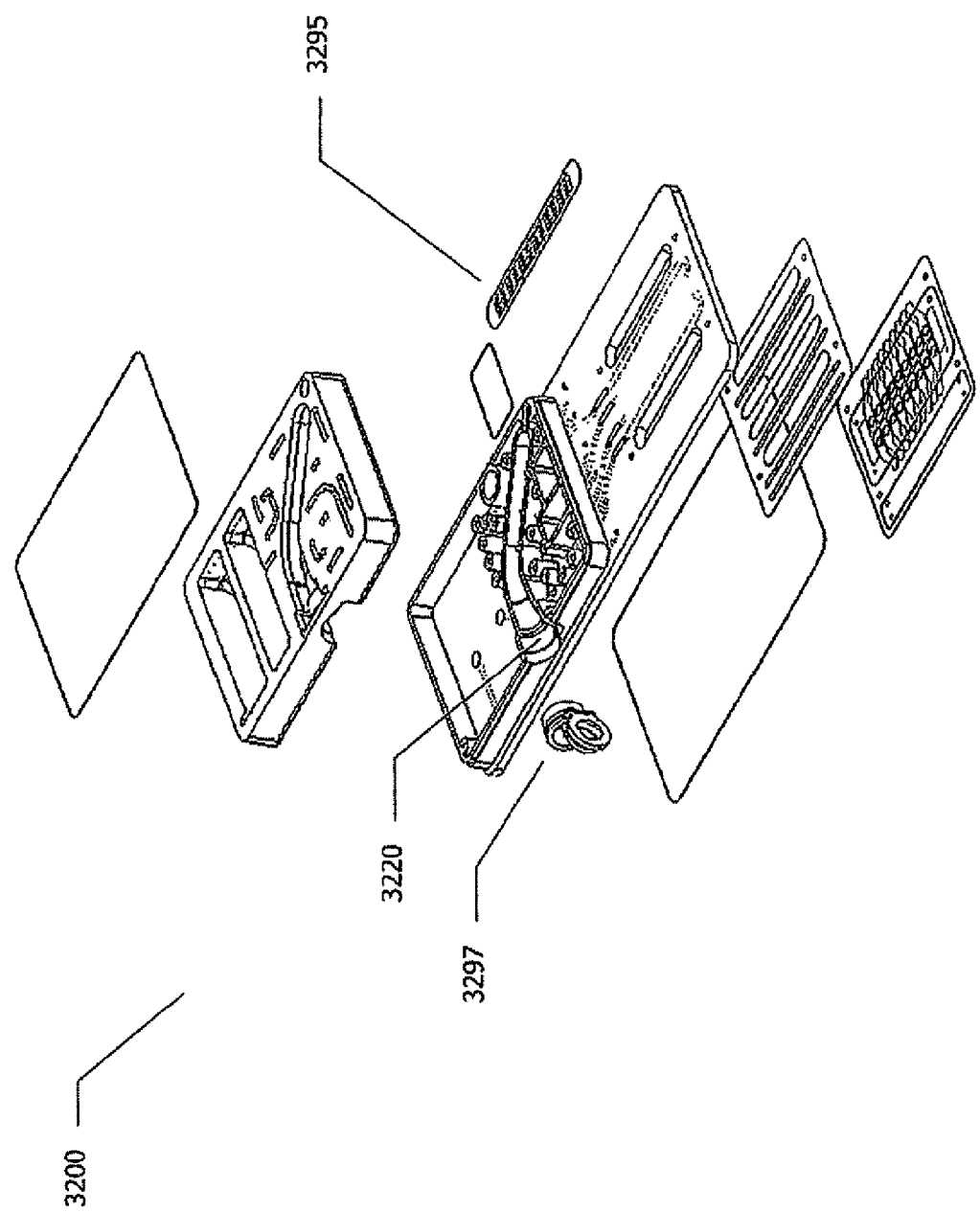
FIG. 33 is an exploded assembly drawing illustrating the laminar assemblage for a two-piece, extraction assay cartridge in accordance with the schematic diagram given in FIG. 32.

FIG. 32 shows a schematic of the fluidic network of cartridge 3200, a preferred embodiment of the invention configured to extract analyte from a matrix, preferably from an applicator stick, most preferably from a swab. FIG. 33 shows an exploded view of a preferred design of cartridge 3200. Cartridge 3200 illustrates two preferred features of cartridges of the invention: a sample chamber for extracting analyte from a matrix and the use of a "reverse flow" wash. Cartridge 3200 has reagent chamber 3210 linked to vent port 3212 and extraction reagent conduit 3214 preferably, comprising a Z-transition). Reagent chamber 3210 holds a liquid reagent suitable for extracting the analyte. Preferably, reagent chamber holds an ampoule of nitrous acid or, more preferably, an ampoule of an acid (preferably, acetic acid) and a dry nitrate salt outside of the ampoule so that rupturing the ampoule leads to the formation of nitrous acid. Nitrous acid is a particularly useful extraction reagent for extracting cell wall antigens from gram positive bacteria and may also be used to extract markers from other organisms in mucus containing samples such as upper respiratory samples (see, e.g., the extraction methods and reagents disclosed in U.S. Provisional Patent Application 60/436,591, filed Dec. 26, 2002, entitled Methods Compositions and Kits for Biomarker Extraction, hereby incorporated by reference).

Cartridge 3200 has elongated sample chamber 3220 (a sample chamber configured for extracting samples such as those described above in connection with FIGS. 28-30) connected to extraction reagent conduit 3214 and sample conduit 3224 so as to allow the flow of extraction reagent through the sample (preferably, through swab head 3205). Preferably, as shown in FIG. 33, sample chamber 3220 is angled or curved along its elongated dimension so as to aid in breaking a scored swab inserted into the sample compartment. Sample conduit 3224 is connected to bubble trap 3226 (preferably connected to bubble trap vent port 3266) for removing air from the extracted sample and waste chamber 3228 (which is preferably connected to waste vent port 3262). Further downstream, sample conduit 3224 is connected to detection chamber 3230. Sample conduit 3224 comprises pill zone 3225 which may hold labeled binding reagents (e.g., labeled antibodies for use as detection reagents in sandwich immunoassays) and/or a neutralization reagent (e.g., a pH buffering component such as Tris, Hepes, phosphate and the like) for neutralizing an acidic extraction reagent in the sample (such as nitrous acid).

Detection chamber 3230, preferably, comprises immobilized binding reagents for analytes of interest, preferably an array of binding reagents, preferably an array of binding reagents supported on electrode arrays for conducting ECL measurements as described for other cartridge embodiments above. In an especially preferred embodiment the binding reagents are antibodies directed against markers of organisms (preferably including at least one gram positive bacteria, most preferably a *Streptococcus* species) that may be found in mucus-containing sample such as upper respiratory samples (see, e.g., the organisms described in U.S. Provisional Patent Application 60/436,591, filed Dec. 26, 2002, entitled Methods Compositions and Kits for Biomarker Extraction, hereby incorporated by reference). Detection chamber 3230 is connected to wash reagent chamber 3240 via wash reagent conduit 3242 (which, preferably, comprises a Z-transition). Vent port 3244 is arranged along wash reagent conduit 3242 between detection chamber 3230 and wash reagent chamber 3240. Wash reagent chamber 3240 is also connected to vent port 3241. Wash reagent chamber 3240 comprises a liquid wash reagent, preferably in an ampoule. The liquid was reagent, preferably, comprises an ECL coreactant and provides an appropriate chemical environment for an ECL measurement.

The fluidic arrangement of cartridge 3200 allows for forward flow of extracted sample through pill zone 3225 into detection chamber 3230 and reverse flow of sample into waste chamber 3228 and wash reagent from wash reagent chamber 3240 into detection chamber 3230.

Cartridge 3200 also has optional control detection chamber 3250 which is preferably configured like detection chamber 3230. The fluidic arrangement of the cartridge allows wash reagent from wash reagent chamber 3240 to pass through pill zone 3252 to detection chamber 3250. Pill zone 3252, preferably, comprises the same binding reagents as pill zone 3225 but also comprises control reagents (preferably, predetermined amount of the analytes measured in detection chamber 3230) so that reconstitution with wash reagent forms a control sample. The fluidic arrangement further allows the forward flow of control sample into waste chamber 3254 (which is preferably connected to waste vent port 3264) and wash reagent from wash reagent chamber 3240 into detection chamber 3250.

As shown in FIGS. 32 and 33, cartridge 3200, preferably, employs many of the same design features as preferred embodiments of cartridge 900 and/or 1400 such as use Z-transitions, laminar construction, electrode arrays, bridge segments, and the like. As shown in FIG. 33, cartridge 3300, preferably, has a two part design. Advantageously, this design allows the sample chamber to be constructed from two sections and simplifies the manufacture of the curved/angled elongated chamber. As shown in FIG. 33, cartridge 3200 may also comprises a bar code 3295 or other identifying feature that can, e.g., identify the assay panel carried out on the cartridge, the cartridge lot, the time of manufacture, the expiration date, cartridge specific calibration data, the sample source, etc.

Figure 23:
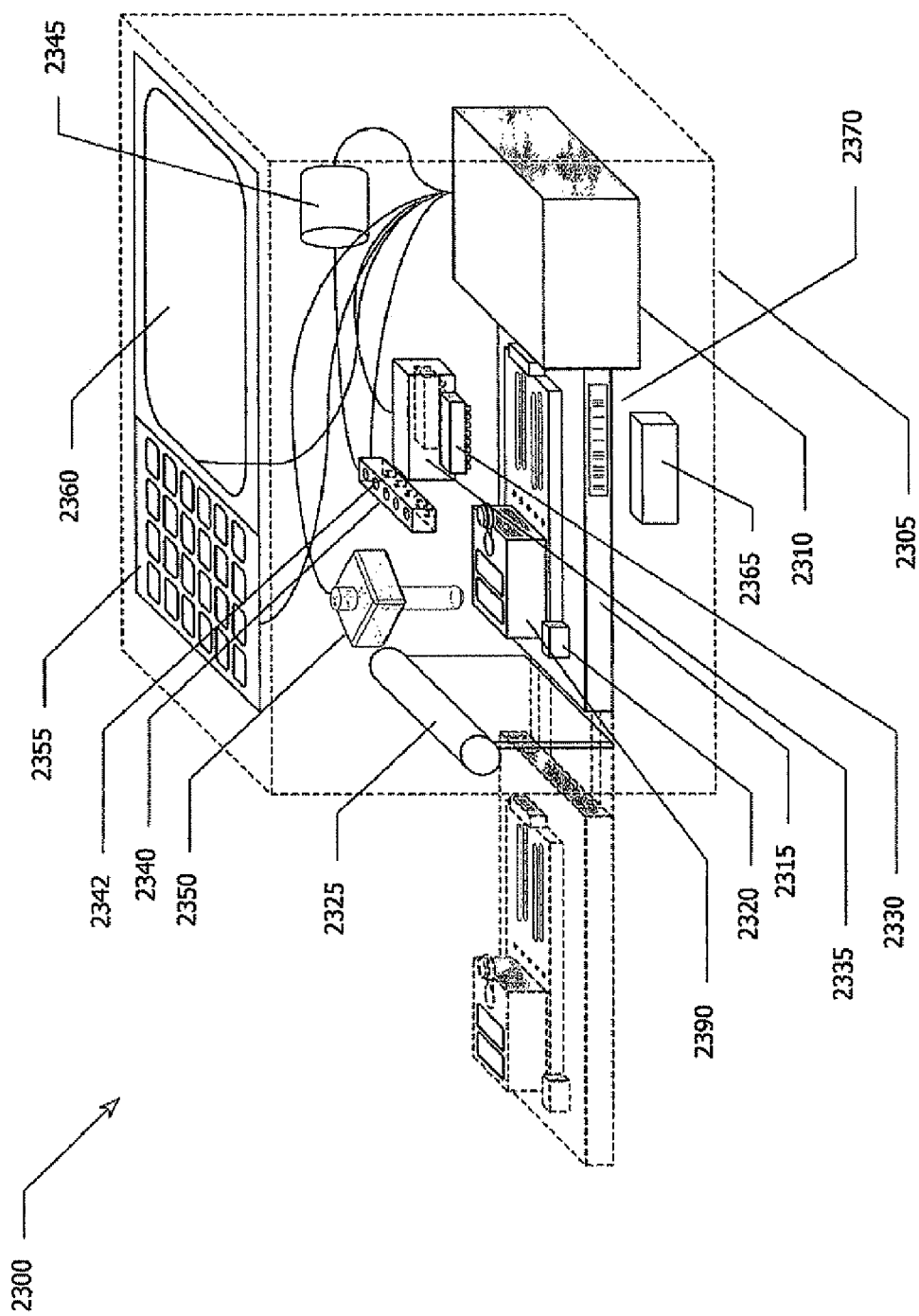
FIG. 23 illustrates one embodiment for a cartridge reader that incorporates various subsystems for performing a predetermined assay. The cartridge reader is depicted holding one embodiment of an assay cartridge.

The fluidic components are preferably adapted and configured to form a fluidic system that can be selectively controlled via a cartridge reader instrument. The cartridge reader 2300 is schematically depicted in FIG. 23 and preferably incorporates various subsystems for performing the predetermined assay. The cartridge reader is shown holding a cartridge 2390 which may be supplied separately. As depicted, the cartridge reader preferably includes the cartridge handler 2315, the fluidic handler 2340 and the assay electronics 2330 subsystems. Together these subsystems are preferably controlled by an electronic control system 2310 responsible, generally, for directing the cartridge handler subsystem to load and position the cartridge within the reader, for controlling/coordinating the introduction/movement of fluids throughout the fluidic network and for directing the assay electronics to perform the assay measurement. The cartridge reader is preferably packaged as a single self-contained unit. In preferred embodiments employing luminescence based assays, a smaller light-tight region is incorporated within the overall cartridge reader housing. This allows the luminescence based assay to be performed within the light tight enclosure to ensure that the readings are not affected by ambient light. Preferably, electronic components and other heat-generating components are located outside of the light tight enclosure.

The cartridge handler subsystem preferably includes a motor to draw the cartridge into the cartridge housing and selectively position the cartridge within the cartridge reader; e.g., position the cartridge under a sensor/detector 2335. In one preferred embodiment, retraction of the cartridge within the cartridge reader housing may be mechanically coupled to one or more mechanisms within the cartridge reader for synchronized/coordinated operation of the linked mechanisms. For example, the retraction of the cartridge may be mechanically coupled to: the mechanism for closing the door 2325 to the light tight enclosure after the cartridge has entered the chamber; the assay electronics subsystem (described in greater detail below) to allow the cartridge reader's electrical contacts 2330 to engage the cartridge's electrical contacts, i.e., be placed into electrical contact with the electrode array's electrode contacts; the fluidic handler subsystem's (described in greater detail below) fluidic manifold 2340 to engage the cartridge's fluid ports, i.e., be placed into fluidic communication with the cartridge's fluidic ports (e.g., establishing a pressure seal between the cartridge's fluidic ports and the fluid manifold); and/or the fluid handler subsystem's reagent module breaking mechanism 2350 to allow the reagent modules such as ampoule(s) to be broken during the cartridge retraction/positioning step.

In certain embodiments the measurement step may comprise reading the signal from each read chamber separately. While this may be accomplished by using a single suitable detector and optimal positioning of the cartridge's read chambers in relation to the single detector, successful measurement/detection may also be carried out by repositioning the desired read chamber in relation to the single detector or repositioning the detector in relation to the desired read chamber. For such an embodiment, the cartridge handler subsystem may include a separate motor to allow for positioning of the cartridge and/or the detector. In a particularly preferred embodiment, the cartridge handler subsystem is adapted and configured to precisely position the cartridge or the detector, or both, such that the detector is in registered alignment with the precise location where the measurement is being performed; e.g., the working electrode presently being stimulated to produce ECL.

In a preferred embodiment a barcode reader 2365 is incorporated on/within the cartridge reader to preferably automatically scan an identifying mark/label 2370 on the cartridge; e.g., as it is drawn into the reader. The label may contain encoded information relating to the specific assays that are to be performed, calibration parameters and/or any other information required to perform the assay. Further, a preferred embodiment may incorporate a heater within the cartridge reader to warm the cartridge to a predetermined temperature, e.g., 37° C., before proceeding.

Preferably, the reader does not come in contact with liquids contained within the cartridge. This feature may be accomplished by using pneumatic pressure applied at the vent ports to drive fluids in the cartridge. The fluidic handler subsystem preferably includes a pump 2345 (preferably a piston pump) to selectively apply positive and/or negative pressure (i.e., apply a vacuum) to one or more of the cartridge's fluidic components in order to selectively control movement of fluids within, and through, the cartridge and its various fluidic components. The fluidic handler subsystem is preferably adapted and configured to fluidically engage the cartridge at one or more fluidic control points; e.g., positive control ports, vent ports, and the like and includes fluidic connectors for providing these fluidic engagements. Selective application of pressure to the cartridge's fluidic components is preferably achieved by incorporating a fluid manifold 2340 housed within the cartridge reader to simplify and enhance the fluidic engagement function and to minimize the number and complexity of fluidic systems. Advantageously, the fluidic manifold 2340 can be adapted and configured to facilitate the use of a single pump; i.e., control valves 2342 can be incorporated within the fluidic manifold 2340 to selectively control fluid movement within and through the various fluidic components of the cartridge. The fluidic handler preferably includes a pressure sensor to facilitate precise/repeatable movement and/or positioning of fluids within the fluid network. The fluidic connectors, preferably, comprise aerosol-prevention plugs or gas-selective membranes (i.e., materials that selectively allow the passage of gas but prevent the passage of liquids) to prevent contamination of the reader fluidics with liquids in a cartridge. The components comprising these plugs or membranes are, preferably, easily removed and replaced if they become contaminated with liquid. Aerosol-prevention plugs are commonly used in pipette tips to prevent contamination of pipettors and include materials that allow the passage of air when dry but swell and seal up the passage when they come in contact with liquid (e.g., filter materials impregnated or coated with cellulose gum).

Figure 17:
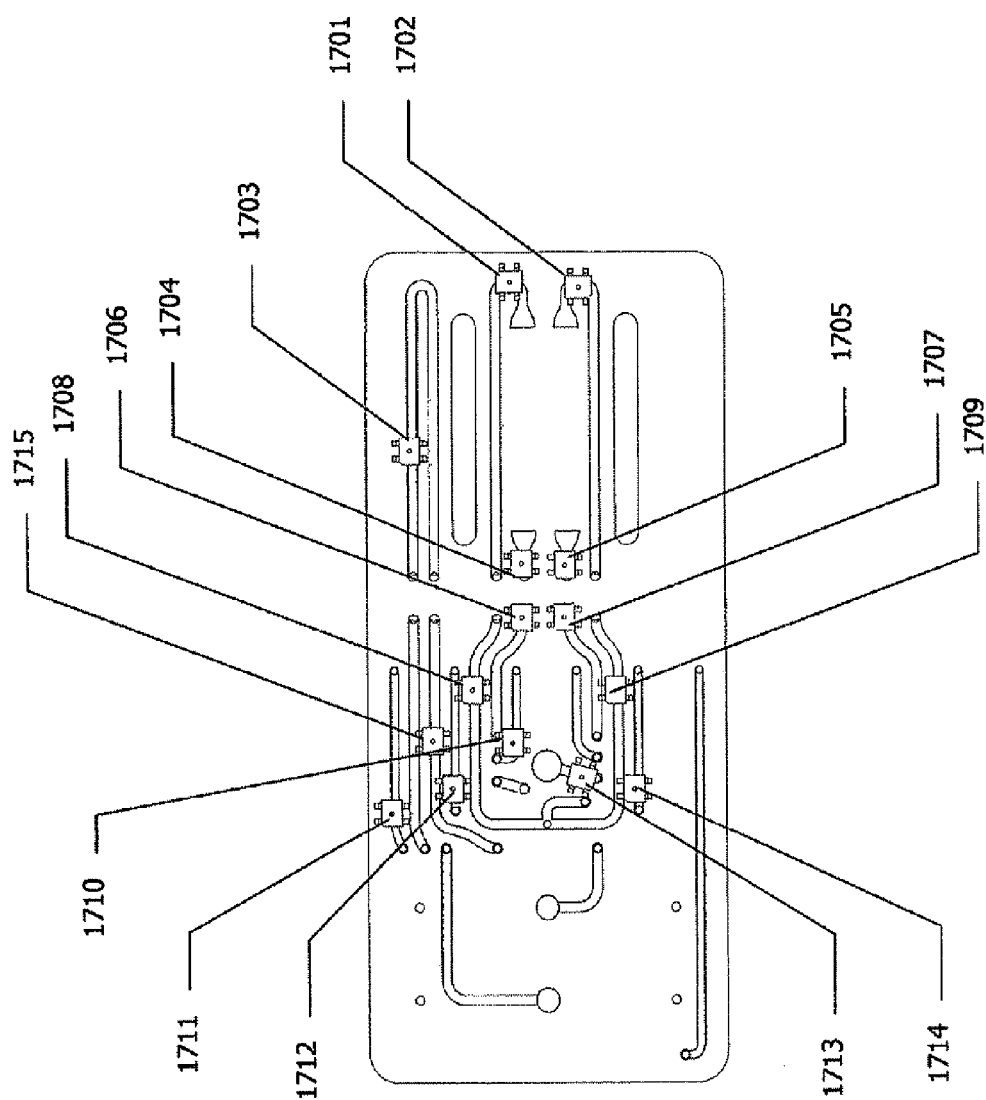
FIG. 17 is a bottom view of the assay cartridge of FIG. 14b illustrating one preferred layout for fluidic detectors to detect/monitor fluid movement.

The fluidic handler subsystem preferably employs fluid sensors (not readily seen in FIG. 23. FIGS. 12 and 17 illustrate alternative fluid sensor layouts in relative arrangement to the cartridge/fluidic network), e.g., reflective photo sensors, positioned at predetermined locations within the fluid network; In accordance with these preferred embodiments, the fluid sensors are positioned in registered alignment with the labeled optical detection points located on the cartridge body. Sensor signal data may be used to provide fluid positional information which may be used to control pump operational parameters such as pump speed, direction and the duration of a specific pump operation. In addition to precise control of fluid movement within and throughout the cartridge, fluid sensors may be used to control mixing of fluids (e.g., during the incubation period, and evacuation of sample from the read chambers during the wash and read cycle) by, e.g., defining the limits of the motion of slug fluid fronts during back and forth mixing motions and/or by measuring an optical property of the fluid such as absorbance or light scattering that is indicative of the state of a mixing operation. The fluid sensors may also be used to conduct viscosity measurements on a sample. In one embodiment, the reader pump is directed to move the fluid front of a sample through a fluidic conduit from one optical sensor position to another by operating the pump at a predefined speed or under conditions designed to achieve a predefined pressure gradient. The time needed to move the fluid between the two positions is indicative of the viscosity. Such a viscosity measurement is optionally used to measure the coagulation time of a blood or plasma sample (e.g., whole blood clotting time, thrombin time, prothrombin time, partial thromboplastin time and/or activated clotting time). Such a method may further comprise introducing one or more coagulation reagents (e.g., by passing the sample over a dry reagent comprising these reagents) prior to conducting the timing step. Suitable reagents for measuring thrombin time may include thrombin. Suitable reagents for measuring prothrombin time may include thromboplastin and/or calcium. Suitable reagents for measuring partial thromboplastin time may include cephalin and a negatively charge substance (preferably, diatomaceous earth, kaolin, glass particles and/or ellagic acid). Suitable reagents for measuring activated clotting time may include negatively charged substances such as diatomaceous earth, kaolin, glass particles and/or ellagic acid.

While the use of optical sensors to monitor fluid flow is advantageous, it is not required. In certain alternate embodiments, fluid movement operations are conducted by operating a pump for a predefined time at predefined speeds, or under conditions which have been determined (e.g., through calibration of the pump) to result in a predetermined movement of a fluid slug.

The assay electronics subsystem preferably includes electrical contacts, sensors and electronic circuitry. The electrical contacts 2330 are preferably adapted and configured to be placed into electrical contact with the electrode array. In one preferred embodiment, the cartridge reader's electronic circuitry may include analog switching and trans-impedance amplification circuits to address a specific pair of electrodes (i.e., pair-wise firing, discussed in greater detail above) and apply a predefined voltage waveform to the circuit formed by that electrode pair. The actual output voltage and current may be optionally measured for diagnostic purposes. Preferably the electronic circuitry is also capable of applying an AC waveform (e.g., 500 Hz or less) for capacitive or conductive measurements (as discussed above). Still further, the electronic circuitry may be configured to generate 20 kHz signals suitable for, e.g., hematocrit measurements of blood samples.

In one particularly preferred embodiment of the cartridge reader configured to perform luminescence based assays, the cartridge reader may employ an optical detector 2335, e.g., a photodiode (most preferably, a cooled photodiode), photomultiplier tube, CCD detector, CMOS detector or the like, to detect and/or measure light/luminescence emanating from the read chambers. If a cooled photodiode is employed, a thermo-electric cooler and temperature sensor can be integrated into the photodiode package itself providing for selective control by the electronic control system.

A computerized control system 2310 is preferably utilized to selectively control operation of the cartridge-based system. The computerized control system may be fully integrated within the cartridge reader, separated from the cartridge reader in an externally housed system and/or partially integrated within and partially separated from, the cartridge reader. For example, the cartridge reader can be configured with external communications ports (e.g., RS-232, parallel, USB, IEEE 1394, and the like) for connection to a general purpose computer system (not shown) that is preferably programmed to control the cartridge reader and/or its sub-systems. In one preferred embodiment, a single embedded microprocessor may be used to control the electronics and to coordinate cartridge operations. Additionally, the microprocessor may also support an embedded operator interface, connectivity and data management operations. The embedded operator interface can preferably utilize an integrated display 2360 and/or integrated data entry device 2355 (e.g., keypad). The computerized control system may also preferably include non-volatile memory storage for storing cartridge results and instrument configuration parameters.

Figure 34:
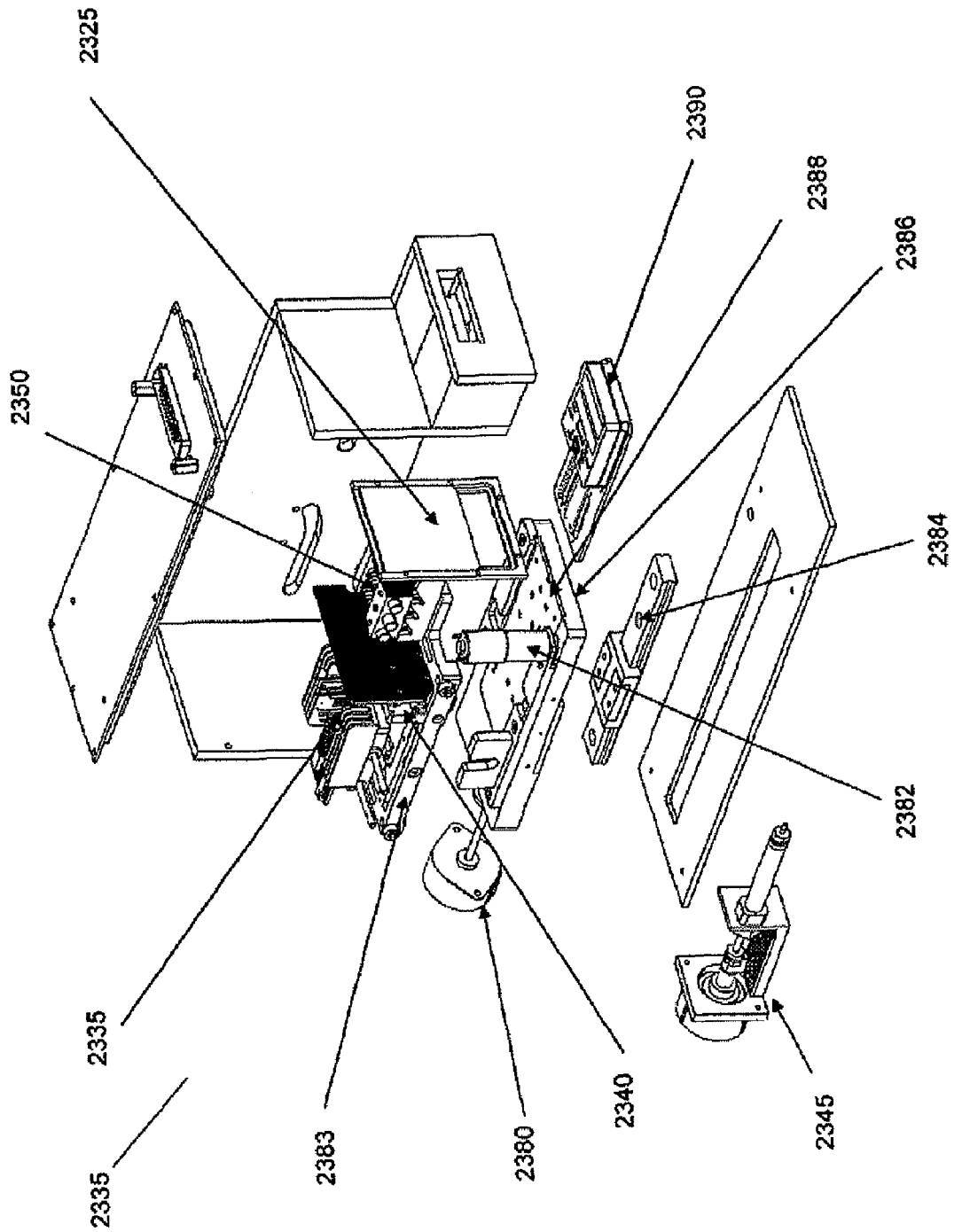
FIG. 34 depicts a cutaway exploded view of one preferred design for a cartridge reader.

FIG. 34 shows a cutaway exploded view of one preferred design for reader 2300 and also shows a cartridge drawer 2386 (preferably comprising an integrated cartridge heater) on linear guide 2384 and driven by motor 2380 for moving the cartridge in and out of the reader. FIG. 34 also shows fluid sensor array 2388 (holding sensors, preferably optical) for detecting fluid at selected positions in the cartridge and a motor 2382 for bringing the cartridge together with frame 2383 which supports the electrical connectors (not shown in this view), fluidic connectors (not shown in this view), ampoule breaking mechanism 2350 and light detector 2335.

Figure 24:
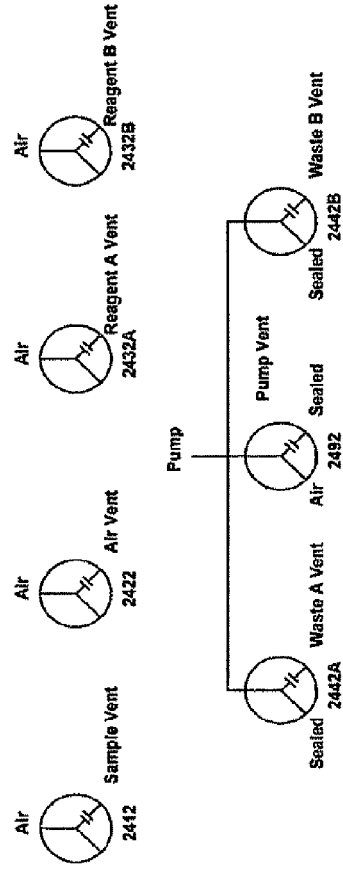
Figure 25:
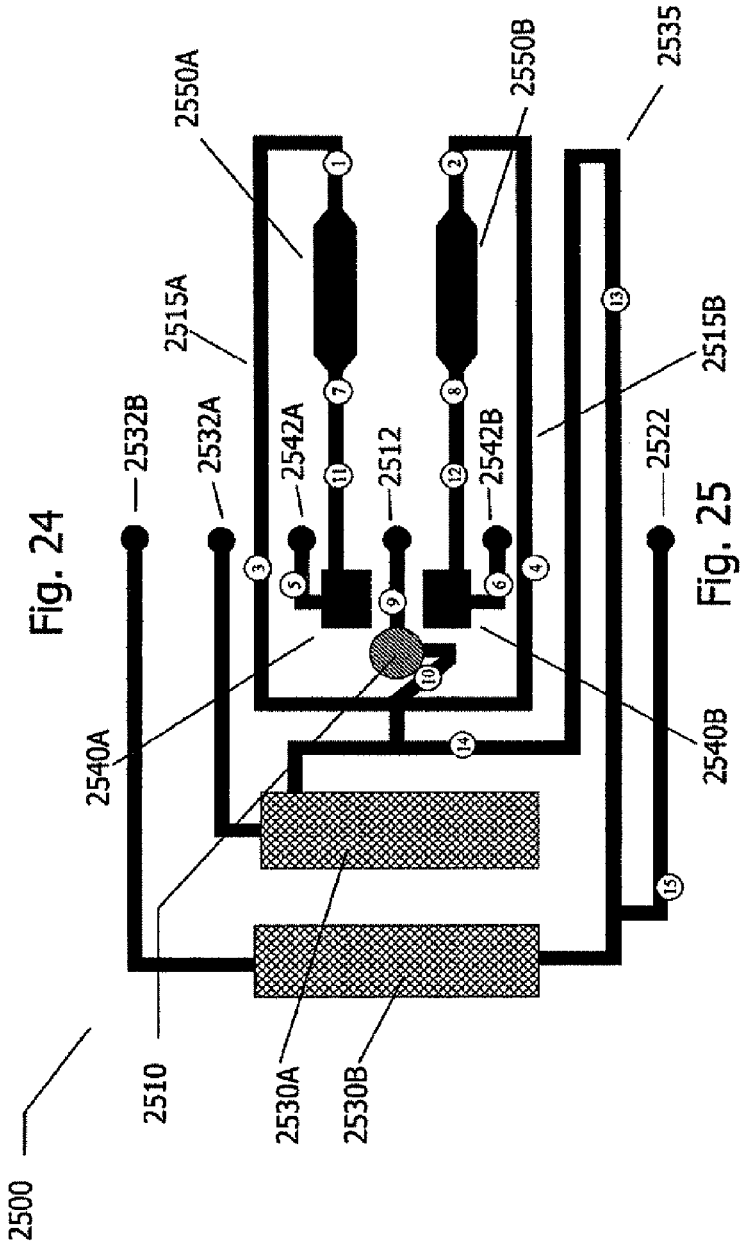
FIG. 25 is the schematic representation shown in FIG. 14a depicting the arrangement of fluidic components and locations of fluid detectors.

FIG. 24 illustrates a preferred configuration of valves in a cartridge reader fluidic handling sub-system configured for use with cartridge 2500 (analogous to cartridge 1400) shown in the fluidic diagram of FIG. 25 (along with preferred locations for cartridge reader fluid detection sensors 1-15). The sub-system comprises a pumping system that comprises a pneumatic pump (preferably, an air piston) linked to a pump manifold. The manifold is connected to control lines (comprising control valves 2412A and 2412B) that connect the pump to selected vent ports (preferably, the waste chamber A vent port 2512A and waste chamber B vent port 2512B) on a cartridge and allow the pump to be used to move fluid in the cartridge away or towards the selected vent ports. The manifold is also connected to a pump vent line (comprising a pump vent line valve 2492) for venting the pump manifold. The control valves have a closed position that seals the control line and the associated cartridge vent port, an open position that connects the pump to the cartridge vent port and, optionally, a vent position that opens the cartridge vent port to ambient pressure. The pump vent line valve has a closed position that seals the pump vent port and an open position that exposes the pump manifold to ambient pressure and releases pressure/vacuum in the pump manifold. The fluidic handling sub-system further comprises vent lines (comprising vent valves 2412, 2422, 2432A and 2432B) that allow venting of vent ports (sample chamber vent port 2512, air port 2522, reagent chamber A vent port 2532A and reagent chamber B vent port 2532B, respectively) on a cartridge (preferably, the cartridge vent ports other than the waste cartridge ports). The vent valves have a closed position that seals the associated cartridge vent port and an open position that exposes the vent port to ambient pressure. The fluidic handling sub-system may also comprise a pressure sensor couple to the pump manifold for detecting pressure in the manifold. During fluidic control of a cartridge, the pressure in the manifold is, preferably, monitored to ensure that it falls within expected pressure ranges for specific operations and confirm that the fluidic handling system is operating properly. The specific preferred valve configuration shown in FIG. 24 is designed to move fluid primarily by aspirating it towards the valve chambers. Other valve configurations, e.g., configurations that drive fluids primarily by positive pressure, will be readily apparent to the skilled artisan and may valves that allow chambers other than the waste chambers to be connected to the pump and/or that allow the waste chambers to be directly vented to the atmosphere.

Figure 26A:
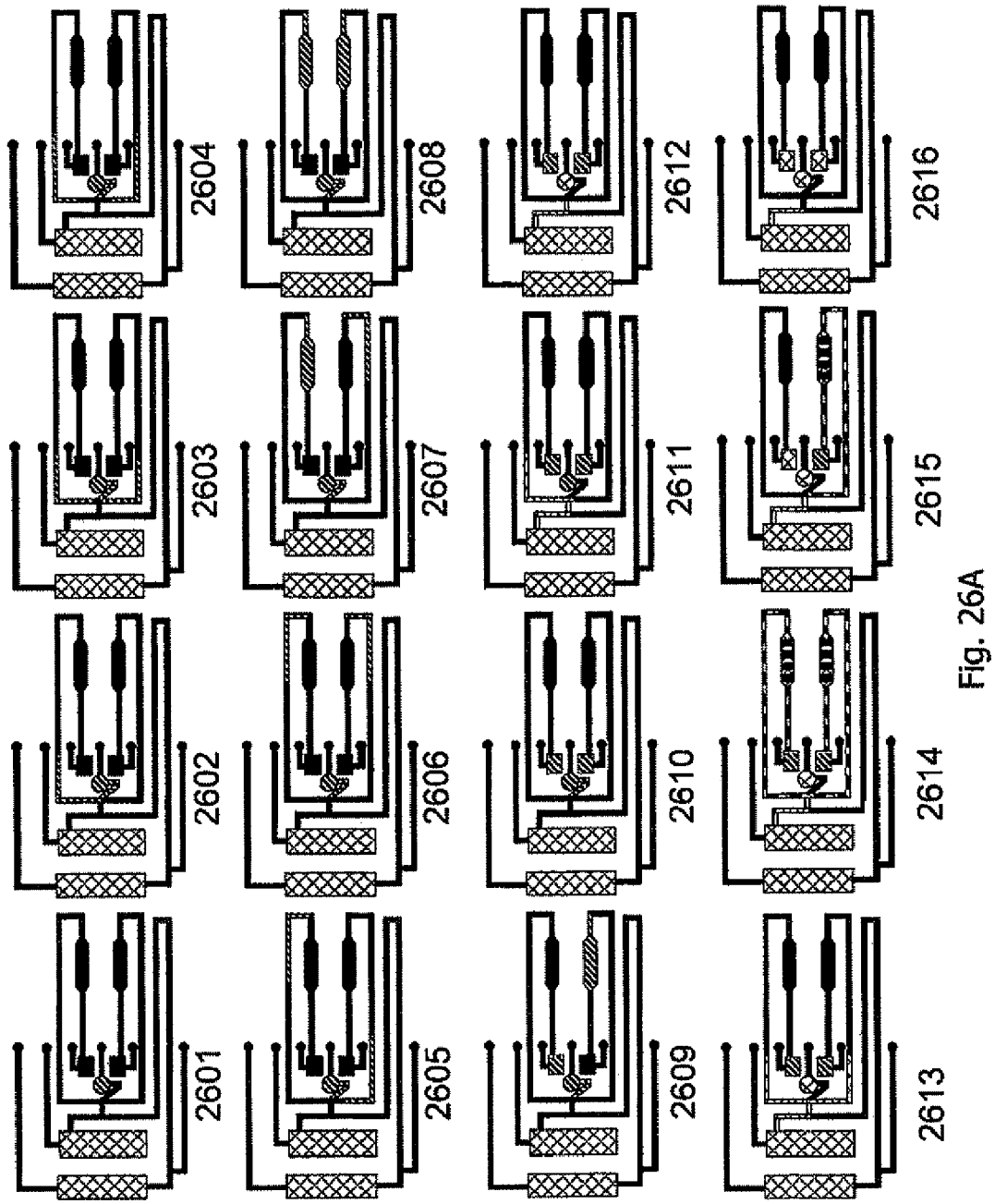
FIGS. 26a through 26c illustrate one preferred manner of operating the assay cartridge depicted in FIG. 25.
Figure 26B:
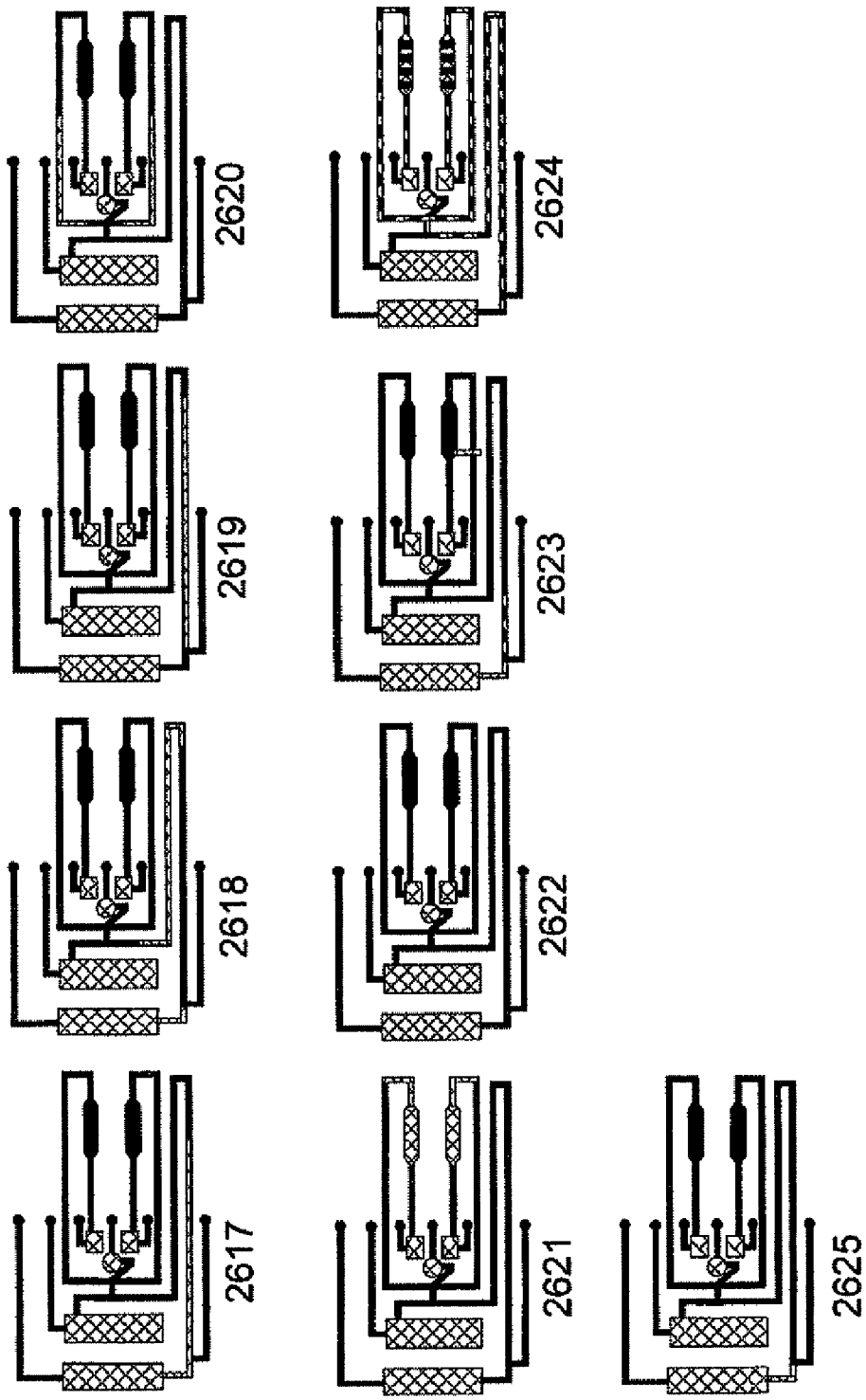
Figure 26C:
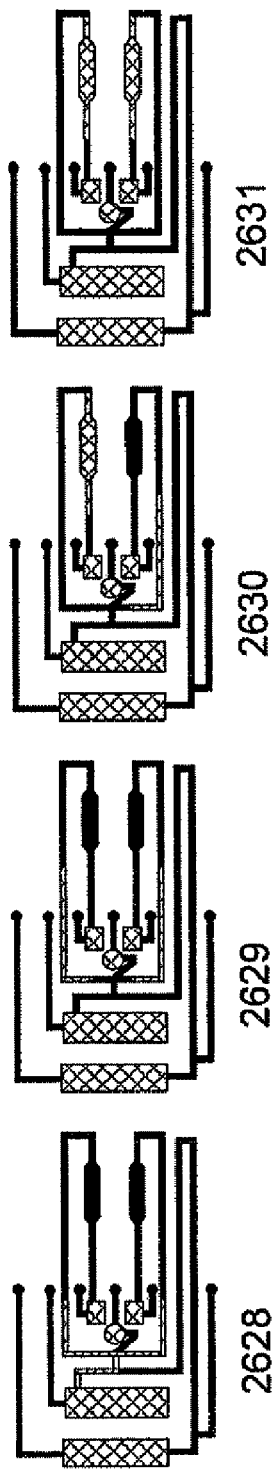

With reference to FIGS. 24 through 26, performance of an assay using a preferred cartridge of the invention will be described. This exemplary method will be described in the context of a two-step multiplexed binding assay using antibodies as binding reagents and ECL as the detection methodology, however, it will be readily apparent to the skilled practitioner that the described fluidic operations can be used in a variety of different assay formats (e.g., binding assays using other classes of binding reagents, enzymatic assays, etc.) and with a variety of different detection technologies. It is also apparent that the sequence of operation discussed below may vary according to differences in the configuration of a particular cartridge as well as differences in the particular assay to be performed.

During operation, the pump vent line valve may be used to enable and disable pressurization of the system for more precise fluid control; when the pump's vent is opened, the system returns to ambient pressure very quickly. Typical fluid draw operations, i.e., routing of fluid within and throughout the fluid network, involve closing the pump vent valve and opening i) one or more (preferably, one) cartridge vent valves, e.g., the sample, air, reagent chamber A and/or reagent chamber B vent valves and ii) one or more (preferably, one) control valves, e.g., waste chamber A or waste chamber B control valves. Therefore, a slug of fluid will move along a path through the fluid network in the cartridge when the fluid channels comprising that path is vented to air at one end and subjected to either pressure or vacuum at the other end.

A user selects the appropriate cartridge for carrying out a desired measurement and introduces sample to the sample introduction port of a cartridge and, preferably, seals a closure on the sample introduction port. The cartridge is inserted into the cartridge reader. Preferably, the cartridge will include features that ensure the cartridge is inserted in the proper orientation; e.g., by incorporating identifying marks to show which direction it should be placed on the tray and/or mechanical features that guide the user to place it in the correct orientation. After the user has successfully prepared and inserted the cartridge, reading/processing of the cartridge is performed by the cartridge reader upon receiving an indication from the user that the read cycle should commence (alternatively, the reader may automatically begin operation upon confirming that a properly prepared cartridge has been properly inserted into the cartridge reader). The subsequent reading of the cartridge is preferably automated; e.g., the cartridge reader's electronic control system (computerized control system or the like) automatically processes and reads the cartridge.

The automated sequence of operations to be performed by the cartridge reader will now be described. Preferably the cartridge includes machine readable indicia, e.g., barcode, that is detected and processed by the cartridge reader. For example, processing of the machine readable indicia may allow the cartridge reader to verify that a valid, readable barcode has been detected and thereafter determine the operational parameters for the present read cycle; i.e., determine the set of assays/tests to be performed, extract any relevant instrument configuration parameters and verify the expiration date. In certain preferred embodiments, the cartridge reader may prompt the user for any data that it requires; e.g., operator ID, sample or patient ID, and the like. Additionally, if the cartridge is capable of running a panel of test, the user may be able to select which test(s) within the panel should want be performed.

Preferably, the reader has a cartridge handling subs-system that mechanically engages the cartridges and moves/aligns it into position. Preferably, this process includes positioning the cartridge within a light-tight enclosure. The reader also makes the appropriate fluidic and/or electronic connections to the cartridge and, optionally, breaks or pierces any reagent modules (e.g., reagent ampoules) present in cartridge reagent chambers. As discussed above, in one preferred embodiment, the cartridge handler's motion would be physically coupled to the fluidic and electronic handlers (and, optionally, the reagent module release mechanism) such that upon positioning the cartridge within the light tight enclosure the electrical contacts and the fluidics manifold engage the cartridge at their respective engagement points (and, optionally, the reagent module release mechanisms releases reagent from any reagent modules). Next, where required or preferred, the electronic control system begins operating a heater in order to bring the cartridge to the appropriate predetermined temperature and maintain the cartridge at such target temperature. In certain preferred embodiments temperature regulation may be controlled by a microprocessor employing a proportional derivative control to control a heater that will maintain the target temperature; preferably a suitable algorithm is employed.

Once the cartridge has been maintained at the target temperature for a predetermined amount of time, the fluid handler may begin processing the cartridge for reading; i.e., assemble the assay. Reference to FIG. 26 will be made to illustrate the intermediary states of the cartridge reader and the position of fluid within the fluid network of cartridge 2500 during a 2-step assay format. As presented in FIG. 26, the starting state of the cartridge 2500 (panel 2601) is illustrated and depicts the location of the constituent fluids within the fluidic network. Assay assembly preferably consists of metering specific volumes of sample fluid, reconstituting dried reagents in the sample fluid and incubating the sample fluid in the detection chambers. Predetermined valves are opened in a prescribed sequence in accordance with the desired fluid flow paths to be assumed by the constituent fluids.

According to the present embodiment in which two read chambers are present and will be utilized for testing the sample, two equal lengths of sample fluid (i.e., slugs) will be drawn; the length of the sample slugs is determined by the volume of the read chambers. The sample slugs are delimited from one another by introducing a slug of air between the two sample slugs. Accordingly, sample chamber vent valve 2412 and a waste chamber vent valve 2442A are opened and the pump vent is closed. The pump is subsequently activated to aspirate/draw the sample from sample chamber 2510 (preferably, overcoming a capillary break provided by a Z-transition that is used to prevent leakage of the sample from the sample chamber) into sample conduit branch 2515A. In this and other pumping steps, a pressure sensor (not shown), preferably, detects the pressure created by the operation and provides confirmation that the pump is aspirating/dispensing fluid properly. When fluid is detected at sensor 3 (see FIG. 26, 2602), the pump vent valve is opened and the pump motor is deactivated. The sample chamber vent valve 2412 and waste chamber vent valve 2442A are then closed. Similarly, sample is drawn into sample conduit branch 2515B by operating the pump with sample chamber vent valve 2412 and waste chamber B vent valve 2442B open (see FIG. 26, panel 2603). Defined slugs of sample fluid are drawn into the sample conduit branches by operating the pump with air vent valve 2422 open as well as the waste chamber A and B vent valves 2442A-B (see FIG. 26, panel 2604). In this and subsequent steps, two slugs may be moved simultaneously through sample conduit branches 2515A and B by holding both waste chamber vent valves open or sequentially through the branches by opening one at a time.

The sample conduit branches, preferably, comprise dry reagent pills (preferably containing one or reagents selected from blocking agents, pH buffers, salts, labeled binding reagents, and the like). One or more of the conduit branches may also comprise spiked analyte for spike recovery controls. In order to reconstitute the dried reagent, the two sample fluid slugs are moved back and forth across the pill zone a predetermined number of times by opening air vent valve 2422 and waste chamber vent valves 2442A and/or B and operating the pump to alternate between applying positive and negative pressure to the waste chamber vents (FIG. 26, panels 2605-2606). The two sample fluid slugs may be moved back and forth simultaneously or mixing of the two slugs may be accomplished in series. The number of repetitions that the sample fluid is cycled across the pill zone may be dependent upon a number of factors, including but not limited to, size/volume of reagent dried reagent pill, composition of reagent pill, drying method employed at the time of reagent deposition/pill formation, and the like. In accordance with preferred embodiments, the number of repetitions that need to be carried out by the fluid handler subsystem can be cartridge specific and can be automatically ascertained by the cartridge reader from the information encoded in the machine-readable indicia affixed/incorporated onto the cartridge. The number of repetitions may be predetermined through empirical results but may also be determined in-situ through the use of one or more sensors adapted and configured to measure the degree of mixing of the reagent(s) and sample fluid; e.g., use of optical sensors (transmittance or reflectance), electrical sensors (impedance, conductance, resistance, and the like).

The sample fluid slugs are now moved into their detection chambers 2550A and 2550B by operating the pump with air vent valve 2422 and waste chamber vent valve 2442A open until the sample slug is detected at sensor 7 and by operating the pump with air vent valve 2422 and waste chamber vent valve 2442B open until the sample slug is detected at sensor 8 (FIG. 26, panels 2607-2608). The sample slugs are incubated in the detection chambers to allow constituents of the sample (e.g., labeled binding reagents, analyte, control analyte, etc.) and immobilized binding reagents within the detection chamber to bind to form binding complexes in the detection chamber. Preferably, a mixing operation is employed to enhance the rate of these binding reactions. Preferably, mixing is achieved by moving the fluid slugs back and forth in the detection chamber by a process analogous to that described for reconstituting the reagent pill (optionally, using sensors 1, 2, 11 and 12 to provide stopping points in each direction). The aspirate and dispense operations are repeated a predetermined number of times, or until the degree of mixing desired has been achieved/detected. After completion of the incubation step, the air and waste chamber vent valves are used to draw the slugs out of the detection chambers and into waste chambers 2540A and B (FIG. 26, panels 2609-2610).

Preferably (as shown), the assay process includes a wash step for removing sample and unbound labeled reagents from the detection chamber. The wash uses a wash reagent (preferably, a buffered solution, more preferably comprising a non-ionic surfactant such as Triton X-100 and most preferably comprising an ECL coreactant such as TPA or PIPES) stored in reagent chamber A 2530A. If the wash reagent is in a reagent module (preferably, ampoule) and the module hasn't been opened, it is opened now. Optionally, the remaining sample fluid is first routed back into the sample chamber to prevent contamination of the wash reagent: first wash reagent is drawn from reagent chamber A 2530A into one of the sample conduit branches by operating the pump to apply negative pressure with reagent chamber A vent valve 2432A and the corresponding waste chamber vent valve 2442A or B open (and, preferably, overcoming a capillary break provided by a z-transition in the reagent conduit); then excess sample is drawn into the sample chamber by operating the pump to apply positive pressure to the waste chamber vent with the sample chamber vent valve open (FIG. 26, panels 2611-26120. Wash reagent is then drawn from reagent chamber A 2530A, through detection chambers 2550A and 2550B and into waste chambers 2540A and 2540B by operating the pump with reagent chamber A vent valve 2432A and waste chamber vent valves 2442A and/or 2442B (simultaneously or sequentially) open (FIG. 26, panels 2613-1616). As shown, in particularly preferred embodiments, the wash fluid may be segmented, i.e., broken up by one or more slugs of air. It has been observed that wash fluid alternating with air within the detection chambers increases the effectiveness of the clean cycle. Segmenting the wash fluid can be accomplished by periodically and temporarily opening the air vent valve 2422 and simultaneously closing the reagent chamber A vent valve 2432A so that air is drawn into the sample conduit. Timing and duration of these operations would dictate the size and frequency of the air slugs introduced into the segmented wash fluid slug.

In the two step format, one or more labeled detection reagents may be incubated in the detection chambers in an additional incubation step. Preferably, the detection reagent solution is prepared by reconstituting a dry reagent pill comprising the detection reagents with an assay diluent contained within reagent chamber B 2530B. If the assay diluent is in a reagent module (preferably an ampoule) and it is not already broken, it is broken now. The assay diluent is drawn into elongated reagent conduit 2535 by aspirating at one of the waste chamber vents while opening reagent chamber B vent valve 2432B until the assay diluent reaches sensor 13 (FIG. 26, panel 2617). A defined volume of assay diluent is prepared by closing reagent chamber B vent valve 2432B and opening air vent valve 2422 and continuing to aspirate at the waste chamber vent; reconstitution of the dry reagent in the elongated reagent conduit is promoted by alternating the pump between positive and negative pressure so as to move the slug back and forth over the dry reagent pill (FIG. 26, panel 2618-2619). In a process analogous to the introduction of sample to the detection chambers, the slug of detection reagent solution is i) distributed between the sample conduit branches 2515 A and B, ii) introduced to the detection chambers (2550 A and B), incubated in the detection chambers while moving the slugs back in forth in the chambers to increase the rate of the binding of the detection reagents to immobilized assay components in the chambers, and iii) expelled from the detection chambers to the waste chambers 2540 A and B (FIG. 26, panels 2620-2622). Optionally, residual detection reagent solution is washed from the detection chambers 2550A and B by aspirating at the waste chamber vents with the reagent chamber B vent valve 2432B open (and, preferably, alternating opening reagent chamber B vent valve 2432B and air vent valve 2422 so as to segment the fluid stream) and then with air vent valve 2422 continuously open to draw the excess assay diluent into the waste chambers (FIG. 26, panels 2623-2625). Alternatively, washing can be accomplished using the wash reagent by repeating the steps in panels 2613-2616.

To provide an appropriate environment for the ECL measurement, detection chambers 2550A and 2550B are filled with the wash reagent (which preferably, is an ECL read buffer comprising an ECL coreactant). Accordingly, wash reagent is introduced into the detection chambers by operating the pump with reagent A chamber vent valve 2432A and waste chamber vent valves 2442A and/or 2442B open so as to aspirate wash reagent into sample conduit branches 2515A and 2515B. Operating the pump with air vent valve 2422 and waste chamber valves 2442A and/or 2442B open introduces slugs wash fluid into the detection chambers (FIG. 16, panels 2628-2631). The above assay is described for a two-step assay that employs two binding steps. An analogous protocol may be used for a one step protocol with one binding step, preferably, by omitting the steps in FIG. 26, panels 2617-2625. In the one step format, all the detection reagents used in the assay are, preferably, stored as dry reagents in sample conduit branches 2515A and 2515B so that they are reconstituted during passage of the sample through the branches. Optionally, reagent chamber B 2530B may be omitted.

Preferably, an ECL measurement is conducted by stimulating/firing working electrodes in the detection chamber. Preferably, the immobilized binding reagents of the detection chambers are immobilized on one or more working electrodes, more preferably on an array of electrodes, most preferably an array of electrodes configured to be fired in a pair-wise fashion (as described above). Electrical potential is applied to the working electrodes to stimulate ECL, preferably in the pair-wise fashion discussed above. The light so generated is detected using an optical detector, e.g., using a photodiode or the like. The cartridge and/or light detector may be moved during the pair-wise firing process so as to align the active electrode with the light detector. Optionally, an array of light detectors or a sufficiently large light detector is used so that movement of the cartridge and/or light detector is not required. Predefined assay-specific conversion parameters may be used to derive concentrations/results from the measured ECL counts; e.g., empirically derived from test data or computed from theoretical predictions/models. In particularly preferred embodiments different types of cartridges may have different electrode patterns but would preferably employ a common cartridge electrode contact pattern/area. Some of the electrode contacts may not be used for lower density cartridge formats.

A preferred sequence of operations that one embodiment of the cartridge reader may employ for firing each read location will now be described. The discussion will reference a photodiode as the optical detector but it should be understood that any suitable optical detector know in the art may be employed. The photodiode assembly (or alternatively, the cartridge) is moved into position; e.g., to the appropriate side of the cartridge's electrode array. The cartridge is then positioned such that the first read location to be processed is brought into a predetermined alignment position with the photodiode (e.g., positioned in registered alignment) and electrical contact is made to the electrode contacts. Once the contact has been made, the reader preferably performs a diagnostic measurement to detect potential anomalies that may interfere with proper operation of the electrode array and/or its components (leads, contacts, electrodes, etc.). Anomalies that are preferably detected include manufacturing defects, surface bubbles, or the like. This diagnostic measurement may be accomplished by preferably applying either a 500 Hz AC voltage or a very low voltage (e.g., less than 100 mV), low current (e.g., less than 1 $\mu$A) DC signal to the electrodes and measuring the surface capacitance. An appropriate predetermined algorithm could then be utilized to determine the presence and/or effect of any such anomalies; e.g., compare measured signal to fixed thresholds, or the like. Preferably, if anomalies are detected, the cartridge reader would record the error and proceed accordingly; e.g., if the anomaly is isolated to a particular electrode/electrode pair, the cartridge reader would skip reading this location and proceed to the next pair and/or next operation. Upon confirming operational status, ECL from the first pair of electrodes is initiated by application of a voltage waveform; data acquisition from the light detector is also begun. After completion of the ECL measurement, the cartridge/light detector are realigned to measure ECL from the second electrode pair and the ECL induction/measurement process is repeated. The cycle is repeated for each electrode pair to be analyzed.

In certain preferred embodiments, once a full set of data points has been acquired, the cartridge reader can either store the acquired data later retrieval/inspection, preferably on machine readable storage medium, and conclude the read cycle by performing the necessary finalization steps (detailed below) or can post-process, preferably performed in real-time, the acquired data and store either the post-processed data alone or in combination with the raw acquired data. Since it is often times important to inspect raw data (e.g., troubleshooting, diagnostics, data cleansing/filtering, and the like), where data is stored only in post-processed format, the corresponding parameters utilized in converting the data may be stored as well so that the raw acquired data can be computed/determined as needed. Alternatively, both the raw acquired data as well as the post-processed data may be stored. Still further, the raw acquired data may only be subjected to a subset of predetermined data conversion/analysis operations in real-time and stored for further post-processing offline, i.e., not in real time; post-processing can be performed by the cartridge reader itself or another device, e.g., a general purpose programmable computer.

In certain preferred embodiments employing ECL detection technology, data conversion/analysis operations may include one or more of: background subtraction; conversion to ECL counts; conversion of ECL counts to concentrations; and/or performance of quality checks on the acquired data. Since it is preferable that the resulting data set represents only the light generated by ECL background subtraction is employed to adjust the measured light to correct for the influence of ambient light or "background" signal. Background subtraction consists of subtracting the background signal from the photodiode signal.

ECL counts are preferably converted to concentrations using predetermined calibration parameters; calibration parameter may be dependent upon one or more factors, e.g., the particular assay/assay format to be performed within the cartridge, the assay reagents employed, the detection technology/techniques employed, cartridge configuration, and the like. Preferably, the calibration parameters are ascertained from machine readable indicia associated with the cartridge, e.g., a barcode affixed to or inscribed on the cartridge body. It should be recognized that conversion to ECL counts can occur in a number of differing ways, including, converting all the acquired data points after acquiring all data, converting each individually acquired data point as it is acquired, converting groups/groupings of acquired data points (e.g., if the cartridge employs a dual read chamber design, converting to ECL counts upon acquiring the data for each read chamber), etc.

In certain preferred embodiments it is preferable to perform quality checks, i.e., assess the quality of the acquired data. Where ECL detection technology is employed, useful quality checks can be performed on the acquired voltage and current data, including: short circuit detection; open circuit detection; voltage following confirmation; and peak current detection. For open and short circuit detection, the output voltage and monitored current are preferably integrated for each acquired data point and the ratio of these two values (current relative to applied voltage) can then be compared against threshold values; these threshold values may be assay-dependent. Results with very low relative current are preferably flagged as probable open circuit conditions while results with very high relative current are preferably flagged as probable short circuits. This information can be stored in relational form for later review/consideration. Alternatively, if either condition is detected, the results can be considered invalid and concentrations for those measurements not reported/computed.

In the case where a voltage following quality assessment is to be employed, each point of the acquired voltage waveform is preferably compared to its corresponding point in a sampled output waveform. Preferably, a predetermined fixed voltage following limit value is defined for the instrument (i.e., cartridge reader/cartridge) and if any pair of points differs by more than that predetermined value (i.e., $|v(t)_{defined} - v(t)_{measured}|$<voltage following limit), the results are preferably flagged or considered invalid. If the results are flagged, this information can be stored in relational form for later review/consideration. If the results are considered invalid, the computed results for those data points are preferably not reported/computed.

Finalization of the cartridge read operation can occur once all of the requisite measurements have been made and all the requisite fluid processing has occurred (e.g., once the final measurements have been made, route all remaining fluid(s) within the channels and/or read chamber(s) into the waste chamber(s)) the cartridge may be ejected from the reader. The cartridge ejection operation preferably occurs in reverse of the operation used to draw the cartridge within the reader. Specifically, the cartridge reader controller ensures that the pump vent is open and that all other valves are closed. Confirmation that the pump is stopped and all electrode contacts are tri-stated is obtained and, if a cartridge heater is present and employed, deactivate the cartridge heater. The cartridge is then preferably moved back onto the reader tray and the reader tray is ejected leaving the cartridge external to the reader and ready for the user, or optionally an automated system, to remove the cartridge from the tray and dispose of it properly.

A preferred embodiment of the performance of an assay using cartridge 3200 is described below, the description focusing on aspects that differ from the operational steps described for cartridge 2500. The operational description includes the use of a preferred valve configuration in the cartridge reader that is similar to that described in FIG. 24 except that it is configured so that air vent port 3244 and air bubble trap vent port 3266 can be connected to the pump, sealed or vented to the atmosphere. In view of the operational description provided for cartridge 2500, the basic operations that are used to move fluid in this preferred embodiment (i.e., opening vent ports on one side of the fluid to be moved to air and applying positive or negative pressure to a vent port on the other side of the liquid) will be apparent and are not always described.

A sample, preferably a sample comprising and/or collected on a solid matrix, is inserted in sample chamber 3220 and cap 3297 is closed. In an especially preferred embodiment, the sample (most preferably an upper respiratory sample and/or a sample suspected of containing a *streptococcus* strain) was collected on an applicator stick (preferably a swab), the applicator stick preferably comprises a pre-defined weak point and the sample chamber is curved as shown in FIG. 33. In this especially preferred embodiment, insertion of the stick into the curved chamber causes the shaft to break. The shaft segment is then, preferably, removed and the head segment is sealed in the chamber by closing cap 3297.

The cartridge is inserted into a reader and mated to the appropriate electrical and fluidic connections as described above for cartridge 2500. The cartridge preferably holds ampoules of extraction and wash buffer in, respectively, reagent chambers 3210 and 3240 which are preferably broken now (or alternatively any time before they are required). The extraction reagent (preferably, nitrous acid, more preferably, nitrous acid made from a liquid acid in a reagent ampoule and a dry nitrate salt present outside the ampoule in chamber 3210) is pulled from its reagent chamber 3210 by opening vent port 3212 to air, vent port 3244 or 3264 to the pump, and operating the pump to draw the extraction reagent through the swab. To eliminate bubbles in the sample, the pump is operated until fluid from the swab is detected at sensor position #1. The fluid is then pushed into bubble trap 3226 by opening vent port 3266 to air and operating the pump to apply positive pressure at vent port 3244 or 3264 (or the reverse, i.e., applying negative pressure at vent port 3266 and opening vent port 3244 or 3264 to air). In bubble trap 3226, the bubbles rise to the top of the trap leaving bubble free liquid at the bottom of the trap. More fluid from the swab is pulled up to sensor #1 and again pushed into the bubble trap. This is repeated as often as necessary to ensure enough bubble-free liquid is collected in the bubble trap to conduct the assay.

Bubble-free sample liquid is then drawn from the bottom of bubble trap 3226 (by aspirating from vent port 3244 or 3264 with vent port 3266 open to air) until the fluid front reaches sensor #1. Vent port 3266 is closed and vent port 3262 is opened to air and the defined slug of sample is drawn forward, pulling air behind it from vent port 3262. This process accurately measures out a defined volume of sample liquid. The sample slug is then drawn across dry assay reagent 3225 to dissolve it—this reagent preferably includes buffers, labeled binding reagents (preferably antibodies) for the assays, stabilizing reagents, and/or other additives such as blocking reagents. For assays employing nitrous acid as an extraction reagent, the dry assay reagent preferably comprises sufficient base (preferably, the base form a pH buffer such as Tris, Hepes, phosphate, PIPES, etc.) to bring the pH of the sample to between 4-10, more preferably between 5-9, more preferably between 6-8. The dissolved reagents may be mixed into the sample by moving the sample back and forth in the fluid line, using sensors to ensure that the liquid remains within a defined region of conduit.

The sample containing the reconstituted assay reagents is then drawn into detection chamber 3230, where immobilized binding agents (preferably antibodies) are present on individual binding zones that are, more preferably, located on electrodes in an electrode array. The sample is incubated for a specific time period over the binding zones, either in a static mode or under mixing, during which time the analyte and labeled binding reagent can bind to each other and/or to the individual binding zones. Mixing is performed by moving the sample back-and-forth between sensors at the end of the read chamber.

Sometime before, during, or after sample incubation, a positive control assay is also performed in the other binding chamber: wash buffer is pulled from the wash buffer storage chamber 3240 to sensor #2 by pulling vacuum on vent port 3264 with vent port 3241 open to air. A fluid slug is metered by closing vent port 3241 and opening vent port 3244 to introduce air behind the metered fluid as it is drawn toward control detection chamber 3250. The metered fluid slug is then drawn over and dissolves dry control reagents 3252. These reagents, preferably, include labeled binding reagents (preferably antibodies), defined amounts of the analytes for the assays (to provide positive controls), stabilizing reagents and/or other assay reagents. The positive control sample, comprising the metered wash buffer slug and rehydrated control reagents, is then incubated in the control detection chamber 3250 either in a static fashion or with mixing by moving the sample between sensors located at the end of the control binding zone.

Following the incubation steps, the positive control sample is drawn into waste chamber 3254 and the extracted swab sample is drawn into the waste chamber 3228. Both detection chambers are washed in a consecutive or simultaneous manner by drawing wash buffer from wash buffer chamber 3240 through the detection chambers and into their corresponding waste chambers (waste chamber 3228 for detection chamber 3230 and waste chamber 3254 for control detection chamber 3250). The wash reagent used during the wash step is preferably segmented by introducing air at vent port 3244. After washing, both the control and sample binding zones are filled with wash buffer to complete the fluid sequence. Advantageously, wash reagent flows through detection chamber 3230 in a direction opposite that in which sample was introduced into chamber 3230. This reverse flow wash ensures the efficient removal of any components in the sample and/or extraction buffer that could interfere with a measurement in the detection chamber.

Preferably, the binding of analyte and/or labeled binding reagents to binding domains in the detection chambers is measured by an ECL measurement as described above for cartridge 2500. ECL is initiated by applying the desired electrical potentials to electrodes supporting the binding zones. The positive control binding zones in detection chamber 3250 will provide a positive signal for each assay and may be used to provide assurance that the assay reagents onboard the cartridge have not degraded. The ECL signal from any of the sample binding zones in detection chamber 3230 indicates the presence of analyte binds to that capture zone or competes with the binding of a labeled reagent to that capture zone.

The assay modules (preferably assay cartridges) of the invention may be used to carry out a variety of different assay formats for measuring analytes interest, preferably formats based on electrode induced luminescence measurements. The assays, preferably, comprise the steps of introducing a sample, and optionally one or more solution phase assay reagents, into an detection chamber (preferably a flow cell) that comprises one or more assay domains (preferably a plurality of assay domains) comprising immobilized assay reagents that bind (with at least some degree of selectivity) with analytes of interest. Preferably, there are at least two assay domains that comprise binding immobilized binding reagents that differ in their selectivity for analytes. Preferably, there is a patterned array of immobilized binding reagents. The detection chamber preferably comprises a plurality of electrodes including one or more assay working electrodes having assay domains. In such a case, electrical energy is applied to the electrodes (e.g., in a pair wise fashion as described above) to induce an assay dependent signal (e.g., an electrochemical signal such as a current or potential or, preferably, an electrode induced luminescence signal, most preferably an electrochemiluminescence signal) at the electrodes which is dependent on the amounts of the analytes of interest present in the sample. The assay dependent signal is measured to determine the amounts of the analytes of interest. The assays may comprise the step of washing the electrodes with a wash solution or they may be carried out in a non-wash format. In washed electrochemiluminescence assays, the assay preferably comprises the steps of washing the electrodes with a solution comprising an electrochemiluminescence coreactant (e.g., a tertiary alkyl amine such as tripropylamine or PIPES; for other examples of suitable coreactants see copending U.S. patent application Ser. No. 10/238,437 filed Sep. 10, 2002) and inducing ECL in the presence of the coreactant. In non-washed ECL assays, a coreactant is preferably introduced into the detection chamber with the sample or is present in the detection chamber prior to the introduction of the sample. Advantageously, assay modules comprising a plurality of assay domains, preferably on a plurality of electrodes, may be used to conduct assays for a plurality of analytes of interest.

In preferred embodiments of the invention, the assay modules (preferably, assay cartridges) of the invention are used to carry out binding assays, most preferably sandwich or competitive binding assays, preferably sandwich or competitive immunoassays. Such assays may, optionally, comprise the step of introducing into the detection chamber labeled binding reagents such as a labeled binding partner of the analyte of interest or a labeled competitor that competes with the analyte of interest for a binding partner of the analyte of interest. Alternatively, these reagents may be stored in dry or wet form in the detection chamber. For more information on the conduct of binding assays, particularly using electrochemiluminescence based detection, see copending U.S. patent application Ser. No. 10/185,274, filed Jun. 28, 2002 and copending U.S. patent application Ser. No. 10/238,391, filed Sep. 10, 2002, these patent applications hereby incorporated by reference.

The assay modules (preferably, assay cartridges) may be used to carry out panels of assays. Suitable panels include panels of assays for analytes or activities associated with a specific biochemical system, biochemical pathway, tissue, organism, cell type, organelle, disease state, class of receptors, class of enzymes, class of pathogen, environmental sample, food sample, etc. Preferred panels include immunoassay for cytokines and/or their receptors (e.g., one or more of TNF-α, TNF-β, IL-1-α, IL1-β, IL2, IL4, IL6, IL10, IL12, IFN-γ, etc.), growth factors and/or their receptors (e.g., one or more of EGF, VGF, TGF, VEGF, etc.), second messengers (e.g., cAMP, cGMP, phosphorylated forms of inositol and phosphatidyl inositol, etc.) drugs of abuse, therapeutic drugs, auto-antibodies (e.g., one or more antibodies directed against the Sm, RNP, SS-A, SS-B Jo-1, and Scl-70 antigens), allergen specific antibodies, tumor markers, cardiac markers (e.g., one or more of Troponin T, Troponin I, myoglobin, CKMB, etc.), markers associated with hemostasis (e.g., one or more of Fibrin monomer, D-dimer, thrombin-antithrombin complex, prothrombin fragments 1 & 2, anti-Factor Xa, etc.), markers of acute viral hepatitis infection (e.g., one or more of IgM antibody to hepatitis A virus, IgM antibody to hepatitis B core antigen, hepatitis B surface antigen, antibody to hepatitis C virus, etc.), markers of Alzheimers Disease (β-amyloid, tau-protein, etc.), markers of osteoporosis (e.g., one or more of cross-linked N or C-telopeptides, total deoxypyridinoline, free deoxypyridinoline, osteocalcin, alkaline phosphatase, C-terminal propeptide of type I collagen, bone-specific alkaline phosphatase, etc.), markers of fertility (e.g., one or more of Estradiol, progesterone, follicle stimulating hormone (FSH), luetenizing hormone (LH), prolactin, β-hCG, testosterone, etc.), markers of congestive heart failure (e.g., one or more of β-natriuretic protein (BNP), a-natriuretic protein (ANP), endothelin, aldosterone, etc.), markers of thyroid disorders (e.g., one or more of thyroid stimulating hormone (TSH), Total T3, Free T3, Total T4, Free T4, and reverse T3), and markers of prostrate cancer (e.g., one or more of total PSA, free PSA, complexed PSA, prostatic acid phosphatase, creatine kinase, etc.), pathogens associated with upper respiratory infection (e.g., influenza A, influenza B, Respiratory Syncytial Virus, Streptococci species), pathogens found in food and water (e.g., *salmonella, listeria, cryptosporidia, campylobacter, E. Coli* 0157, etc.), sexually transmitted diseases (e.g., HIV, syphilis, herpes, gonorrhea, HPV, etc.), blood borne pathogens and potential bioterrorism agents (e.g., pathogens and toxins in the CDC lists of Select A, B and C agents such as *B. anthracis, Y. pestis*, small pox, *F. tularensis*, ricin, botulinum toxins, *staph* enterotoxins, etc.). Preferred panels also include nucleic acid arrays for measuring mRNA levels of mRNA coding for cytokines, growth factors, components of the apoptosis pathway, expression of the P450 enzymes, expression of tumor related genes, pathogens (e.g., the pathogens listed above), etc. Preferred panels also include nucleic acid arrays for genotyping individuals (e.g., SNP analysis), pathogens, tumor cells, etc. Preferred panels also include libraries of enzymes and/or enzyme substrates (e.g., substrates and/or enzymes associated with ubiquitination, protease activity, kinase activity, phosphatase activity, nucleic acid processing activity, GTPase activity, guanine nucleotide exchange activity, GTPase activating activity, etc.). Preferred panels also include libraries of receptors or ligands (e.g., panels of G-protein coupled receptors, tyrosine kinase receptors, nuclear hormone receptors, cell adhesion molecules (integrins, VCAM, CD4, CD8), major bistocompatibility complex proteins, nicotinic receptors, etc.). Preferred panels also include libraries of cells, cell membranes, membrane fragments, reconstituted membranes, organelles, etc. from different sources (e.g., from different cell types, cell lines, tissues, organisms, activation states, etc.).

The present invention also includes kits. The kits may include disassembled components necessary to make an assay module of the invention. Alternatively, the kits may comprise, in one or more containers, an assay module of the invention and at least one additional assay reagent necessary to carry out an assay. The one or more assay reagents may include, but are not limited to, binding reagents (preferably, labeled binding reagents, more preferably binding reagents labeled with electrochemiluminescent labels) specific for an analyte of interest, ECL coreactants, enzymes, enzyme substrates, extraction reagents, assay calibration standards or controls, wash solutions, diluents, buffers, labels (preferably, electrochemiluminescent labels), etc. Preferred kits of the invention include cartridges adapted for extracting samples (as described in detail above), preferably samples collected on applicator sticks. These kits preferably include applicator sticks (more preferably swabs) that have properties that are matched to the specific cartridge. Most preferably, the applicator sticks have weak points that are matched to the geometry of a sample introduction chamber in the cartridge such that i) the sticks may be inserted and cleaved in the cartridge to form a head segment and ii) the head segment can be sealed in the sample chamber. Such kits may also include extraction buffers for extracting the sample on the applicator stick. One embodiment of the invention is a ket for measuring upper respiratory pathogens or pathogens that may be found in mucus-containing samples. The kit includes an applicator stick (preferably, a swab) for collecting the sample (the stick preferably comprising a weak point) and a cartridge for measuring a panel of pathogens (e.g., a panel of upper respiratory pathogens, a panel of sexually transmitted diseases, a panel of pathogens that dwell in mucous membranes, etc.), the cartridge preferably comprising one or more binding domains containing binding reagents that bind markers of these pathogens. The kit may also contain (in the cartridge or as a separate component), one or more labeled binding reagents against markers of these pathogens.

The invention includes assay modules preferably assay cartridges) and module readers preferably cartridge readers) as described above. These may be supplied as separate components. The invention also includes assays systems that comprise an assay module (preferably a cartridge) and a module reader (preferably a cartridge reader).

The present invention is not to be limited in scope by the specific embodiments described herein. Indeed, various modifications of the invention in addition to those described herein will become apparent to those skilled in the art from the foregoing description and accompanying figures. Such modifications are intended to fall within the scope of the claims.

What is claimed is:

1. A method of performing a plurality of biochemical assays using a plurality of electrodes comprising the steps of:
   (a) applying electrical energy between first and second electrodes of said plurality of electrodes;
   (b) measuring an assay dependent signal at said second electrode;
   (c) applying electrical energy between said second electrode and a third electrode of said plurality of electrodes; and
   (d) measuring an assay dependent signal at said third electrode.

2. The method according to claim 1 wherein said assay dependent signal is selected from the group consisting of electrical current, electrical potential and electrode-induced luminescence.

3. The method according to claim 2 wherein said assay dependent signal is electrochemiluminescence.

4. The method according to claim 1, said second electrode having a second electrode assay reagent immobilized thereon and said third electrode having a third electrode assay reagent immobilized thereon.

5. The method according to claim 4 wherein said second electrode assay reagent and said third electrode assay reagent are binding reagents each specific for a different analyte of interest.

6. The method according to claim 1 wherein said plurality of electrodes are arranged within a flow cell, wherein said flow cell comprises a flow cell path.

7. The method according to claim 6 wherein said plurality of electrodes are arranged sequentially.

8. The method according to claim 1 wherein said first electrode is adjacent said second electrode and said second electrode is adjacent said third electrode.

9. The method according to claim 1 wherein said plurality of electrodes are arranged within a single detection chamber.

10. The method according to claim 1 wherein said plurality of electrodes comprise printed carbon ink.

11. The method according to claim 4 wherein said assay reagents are present within an assay domain defined by a dielectric layer on said electrodes.

12. The method according to claim 6 wherein:
said first, second and third electrodes having first, second and third electrical leads for supplying electrical energy to said electrodes; and
said flow cell being in fluid communication with an inlet conduit at least partially defined by exposed surfaces of said first and third electrical leads, wherein fluid in said inlet conduit is in electrical contact with said exposed surfaces,
wherein the method further comprises the step of applying an inlet conduit interrogation potential between said exposed surfaces to determine the presence or composition of fluid in said inlet conduit.

13. The method according to claim 12 wherein said interrogation potential is of insufficient magnitude to induce electrochemiluminescence at said first or third electrodes.

14. The method according to claim 1, further comprising the steps of:
applying electrical energy between said third electrode and a fourth electrode of said plurality of electrodes; and
measuring an assay dependent signal at said fourth electrode.

15. A method of performing a plurality of assays comprising measuring assay dependent signals using a plurality of electrodes, wherein at least one of said plurality of electrodes is used as a working electrode for measuring an assay dependent signal and, subsequently, as a counter electrode for measuring a different assay dependent signal at a different one of said plurality of electrodes.

16. The method of claim 15, wherein each of at least two of said plurality of electrodes is used as a working electrode for measuring an assay dependent signal and, subsequently, as a counter electrode for measuring a different assay dependent signal at a different one of said plurality of electrodes.

17. The method of claim 15, wherein said plurality of electrodes comprises a dedicated counter electrode, a dedicated working electrode and two or more additional electrodes, each of which is used as a working electrode for measuring an assay dependent signal and, subsequently, as a counter electrode for measuring a different assay dependent signal at a different one of said plurality of electrodes.

* * * * *